US011072801B2

(12) United States Patent
Vandendriessche et al.

(10) Patent No.: US 11,072,801 B2
(45) Date of Patent: Jul. 27, 2021

(54) MUSCLE-SPECIFIC NUCLEIC ACID REGULATORY ELEMENTS AND METHODS AND USE THEREOF

(71) Applicants: VRIJE UNIVERSITEIT BRUSSEL, Brussels (BE); VIB VZW, Ghent (BE); UNIVERSITEIT GENT, Ghent (BE)

(72) Inventors: Thierry Vandendriessche, Bierbeek (BE); Marinee Chuah, Bierbeek (BE); Pieter De Bleser, Buggenhout (BE)

(73) Assignees: VRIJE Universiteit Brussel, Brusset (BE); VIB VZW, Ghent (BE); Universiteit Gent, Ghent (BE)

( * ) Notice: Subject to any disclaimer, the term of this patent is extended or adjusted under 35 U.S.C. 154(b) by 521 days.

(21) Appl. No.: 15/112,795

(22) PCT Filed: Jan. 21, 2015

(86) PCT No.: PCT/EP2015/051081

§ 371 (c)(1),
(2) Date: Jul. 20, 2016

(87) PCT Pub. No.: WO2015/110449

PCT Pub. Date: Jul. 30, 2015

(65) Prior Publication Data

US 2016/0340693 A1 Nov. 24, 2016

(30) Foreign Application Priority Data

Jan. 21, 2014 (EP) .................................... 14151960

(51) Int. Cl.

| | |
|---|---|
| ***C12N 15/85*** | (2006.01) |
| ***A61K 48/00*** | (2006.01) |
| ***C12N 15/864*** | (2006.01) |
| ***C12N 15/86*** | (2006.01) |

(52) U.S. Cl.

CPC .......... *C12N 15/85* (2013.01); *A61K 48/0058* (2013.01); *A61K 48/0075* (2013.01); *C12N 15/86* (2013.01); *C12N 15/8645* (2013.01); *C12N 2710/10043* (2013.01); *C12N 2750/14143* (2013.01); *C12N 2800/22* (2013.01); *C12N 2830/008* (2013.01); *C12N 2830/15* (2013.01); *C12N 2830/85* (2013.01)

(58) Field of Classification Search

CPC .... C12N 15/85; C12N 15/86; C12N 15/8645; C12N 2830/85; C12N 2750/14143; C12N 2830/008; C12N 2830/15; A61K 48/0058; A61K 48/0075

USPC .................. 435/320.1; 424/199.1; 514/44 R

See application file for complete search history.

(56) References Cited

U.S. PATENT DOCUMENTS

| | | | |
|---|---|---|---|
| 2002/0198371 | A1 | 12/2002 | Wang et al. |
| 2008/0039413 | A1 | 2/2008 | Morris et al. |

FOREIGN PATENT DOCUMENTS

| | | |
|---|---|---|
| CN | 103421786 | 12/2013 |
| CN | 103451284 | 12/2013 |
| WO | WO 1996/26284 | 8/1996 |
| WO | WO 2002/095006 | 11/2002 |
| WO | WO 2003/074711 | 9/2003 |
| WO | WO 2007/039699 | 4/2007 |
| WO | WO 2007/078599 | 7/2007 |
| WO | WO 2008/073303 | 6/2008 |
| WO | WO 2008/124934 | 10/2008 |
| WO | WO 2009/130208 | 10/2009 |
| WO | WO 2011/051450 | 5/2011 |

OTHER PUBLICATIONS

Genbank: AC024952 "*Homo sapiens* chromosome 7 clone RP11-66F23, complete sequence", published Nov. 28, 2000, one page.*

Genbank: AQ471867 "CITBI-E1-2587B6.TH CITBI-E1 *Homo sapiens* genomic clone 2587B6, genomic survey sequence", published Dec. 19, 2010, one page.*

Milewski et al. (2004) Development 131, 829-837.*

Liu et al. (2007) PNAS, vol. 104(52), 20844-20849.*

Tosolini et al. (2017) Frontiers in Molecular Neuroscience, vol. 10, Article 405, doi:10.3389/fnmol.2017.00405, pp. 1-23.*

Wang et al. (2014) Disc. Med., vol. 18(98), 151-161, author manuscript p. 1-18.*

GenBank: DX563003.1 "MUGQ_CH252P037A01T7_AV828_063 CHORI-252 Vervet Monkey Library Chlorocebus aethiops genomic clone CH252-37A1, genomic survey sequence" published Feb. 2014, one page.

GenBank: AQ703822.1 "HS_5503_B1_C10_SP6E RPCI-11 Human Male BAC Library *Homo sapiens* genomic clone Plate=1079 Col=19 Row=F, genomic survey sequence" published May 2010, one page.

Katal et al., "Adeno-associated virus serotype 9 efficiently targets ischemic skeletal muscle following systemic delivery", Gene Therapy, 20:930-938 (Mar. 2013).

Atschul et al., "Basic local alignment search tool", J Mol Bio., 215(3) 403-410 (Oct. 1990).

De Bleser et al., "A distance difference matrix approach to idenitying transcription factors that regulate differential gene expression", Genome Biol., 8(5):R83 (2007).

GenBank Accession No. HY110671, "HY110671 RIKEN full-length enriched human cDNA library, brain *Homo sapiens* DNA clone H06D021N05, mRNA sequence," May 5, 2012 (1 page).

(Continued)

*Primary Examiner* — Anne Marie S Wehbe

(74) *Attorney, Agent, or Firm* — McDonnell Boehnen Hulbert & Berghoff LLP

(57) ABSTRACT

The present invention relates to nucleic acid regulatory elements that are able to enhance muscle-specific expression of genes, in particular expression in cardiac muscle and/or skeletal muscle, methods employing these regulatory elements and uses of these elements. Expression cassettes and vectors containing these nucleic acid regulatory elements are also disclosed. The present invention is particularly useful for applications using gene therapy, more particularly muscle-directed gene therapy, and for vaccination purposes.

19 Claims, 38 Drawing Sheets

Specification includes a Sequence Listing.

(56) References Cited

OTHER PUBLICATIONS

Encode project Consortium, "An integrated encyclopedia of DNA elements in the human genome", Nature, 489 (7414):57-74 (Sep. 2012).
Koo et al., "Delivery of AAV2/9-microdystrophin genes incorporating helix 1 of the coiled-coil motif in the C-terminal domain of dystrophin improves muscle pathology and restores the level of alpha1-syntrophin and alpha-dystrobrevin in skeletal muscles of mdx mice" Hum Gene Ther., 22(11):1379-88. (Nov. 2011). Epub (May 2011).
Kota et al., "Follistatin gene delivery enhances muscle growth and strength in nonhuman primates", Sci. Transl. Med., 1(6):6ra15 (Nov. 2009).
Levitt et al., "Definition of an efficient synthetic poly(A) site", Genes Dev., 3(7):1019-1025 (Jul. 1989).
Li et al., "High level desmin expression depends on a muscle-specific enhancer", J Biol. Chem., 266(10):6562-6570 (Apr. 1991).
Li et al., "Synthetic muscle promoters: activities exceeding naturally occuring regulatory sequences", Nat Biotechnol., 17(3):241-245 (Mar. 1999).
McCarty et al., "Adeno-associated virus terminal repeat (TR) mutant generates self-complementary vectors to overcome the rate-limiting step to transduction in vivo", Gene Ther., 10(26):2112-8 (Dec. 2003).
McCarty et al., "Self-complementary recombinant adeno-associated virus (scAAV) vectors promote efficient transduction independently of DNA synthesis", Gene Ther., 8(16):1248-54 (Aug. 2001).
Nathwani et al, "Sustained high-level expression of human factor IX (hFIX) after liver-targeted delivery of recombinant adeno-associated virus encoding the hFIX gene in rhesus macaques", Blood J., 100(5):1662-1669 (Sep. 2002).
Nathwani et al., "Self-complementary adeno-associated virus vectors containing a novel liver-specific human factor IX expression cassette enable highly efficient transduction of murine and nonhuman primate liver", Blood J., 107 (7):2653-2661 (Apr. 2006).
Son et al., "Database of mRNA gene expression profiles of multiple human organs", Genome Research, 15:443-450 (2005).
Su et al., "A gene atlas of the mouse and human protein-encoding transcriptomes" PNAS, 101(16):6062-6067. (Apr. 2004).
Tatusova et al., "BLAST 2 sequences, a new tool for comparing protein and nucleotide sequences", FEMS Microbiol Lett., 174(2):247-250 (May 1999).
Vandendriessche et al., "Efficacy and safety of adeno-associated viral vectors base don serotype 8 and 9 vs. lentiviral vectors for hemophilia B gene therapy", J. Thromb Haemost, 5(1):16-24 (Jan. 2007). Epub (Sep. 2006).
Wang et al., "Construction and analysis of compact muscle-specific promoters for AAV vectors", Gene Ther., 15 (22):1489-1499. (Nov. 2008). Epub (Jun. 2008).
Wu et al., "Optimization of self-complementary AAV vectors for liver-directed expression results in sustained correction of hemophilia B at low vector dose", Molecular Therapy, 16(2):280-289 (Feb. 2008).
Xiao et al., "TiSGeD: a database for tissue-specific genes", Bioinformatic, 26(9):1273-1275. (May 2010). Epub (Mar. 2010).
Written Opinion issued by the International Searching Authority for International Application No. PCT/EP2015/051081; dated Jul. 1, 2015, (19 pages).
International Search Report issued by the International Searching Authority for International Application No. PCT/EP2015/051081, dated Jul. 1, 2015, (14 pages).
GenBank Accession No. FI096286, "MUGQ_CH252P470D05Sp6_CH0143_029 CHORI-252 Vervet Monkey Library Chlorocebus aethiops genomic clone CH252-470D5, genomic survey sequence," May 1, 2008 (1 page).
GenBank Accession No. AQ503558, "RPCI-11-297C4.TV RPCI-11 *Homo sapiens* genomic clone RPCI-11-297C4, genomic survey sequence," Apr. 29, 1999 [retrieved from the Internet https://www.ncbi.nlm.nih.gov/nucgss/AQ503558] [retrieved on Nov. 6, 2017] (2 pages).
GenBank Accession No. AC127457, "*Homo sapiens* chromosome 16 clone RP11-100F10, complete sequence," Jan. 7, 2004 (2 pages).
English language translation of Abstract of CN103451284.

* cited by examiner

FIG. 2A

SEQ ID NO: 1

GTTCTCCTCTATAAATACCCGCTCTGGTATTTGGGGTTGGCAGCTGTTGCTGCCAGGGAGA
TGGTTGGGTTGACATGCGGCTCCTGACAAAACACAAACCCCTGGTGTGTGTGGGCGTGGGT
GGTGTGAGTAGGGGGATGAATCAGGGAGGGGGCGGGGGACCCAGGGGGCAGGAGCCACACA
AAGTCTGTGCGGGGGTGGGAGCGCACATAGCAATTGGAAACTGAAAGCTTATCAGACCCTT
TCTGGAAATCAGCCCACTGTTTATAAACTTGAGGCCCCACCCTCGACAGTACCGGGGAGGA
AGAGGGCCTGCACTAGTCCAGAGGGAAACTGAGGCTCAGGGCTAGCTCGCCCATAGACATA
CATGGCAGGCAGGCT

FIG. 2B

SEQ ID NO: 2

CGTCTATAAATTCCAGGGAAGGTCTCTGATTGGCCCTGCTCATTCCCAGGCCCATTCCTTG
ACCCAGTCACTGAAGTCAGGGAGATGCAGTAATAAGACTGGCTGGAATCAGGGTCTTTAGG
GGTGGAGGGATGGGGAGGAGGCACAGCATGTCATCAAAATAAGGAAATTGCAAAAGAAAGC
TTGCAGGCTACTTTGAATGACAATGAGAAAGACGGTGCTGCCTGAGTGTGTTAAGGATCCA
CATGGTCTCCAAAATCCTCCAGGAGCATACAGTCTAGTCTGGGAGATGAGACACAAAAATA
ACCAGAACACAACAGCTTGCACTGACTCGAGGGCTGGATAAGAATATCTGGAACTCCCCCA
TCTATTTCAGAAGCTTGTCTCTTGGATGAAAATTAGACACTTAATGGGAAAGGGCTTTGAA
AAGAGTGC

FIG. 2C

SEQ ID NO: 3

AAAAAATAAAAATAAAAAATAAAAATAAATAAAGTGGATGGCTTAGAGTATCTTTTCTGTT
TAGACCTGACTAAAGCTTAGACATAATTGTTAGTTTAGGCTCTCAGGGTAAAATTTATTAC
TGTAAATCCAAAAAATCCCTTCTTCTTCTTTTTTTTTTTTTTTTTGGTCCTTGAATTAAAT
GCTGTCACCTCCTTCTTGAAAGGAGAAACTATTAGTCAGATTTGAAAATCCTCTTTATCAC
CCAGGAAAATCATTTTTATGGACACTTTGTCTTTCTGTAGTCTGACTTAGAAGCAGCCTGT
TTTTGATAGGTTGAAGTTTTCATCTTGAACACAAACCCTGTTTGTGTGTCCCCTACTCCCC
AGTTTGATGTGCCAGGCACTTTGTTCTCAAGCCCAGCAGCTGTTGTGGGATGAGGGGACAT
TTTGCATGCTTAGCCAGCAGCTGCCAGAAACATTTCTAATCTGGTTTTGGCAGGAAATAGG
GCACAAGTGGAAGCCAAGTTAAAAGAAGCTGGAAAAATAAACAGAATAACTTTAGATGTCA
CT

FIG. 2D

SEQ ID NO: 4

TGCACTGTAGACTATTTATGTTTGCATATTTTTCAGGATTGTGTACAGTAAACCTTAAGTG
AATACAAAGGATCCAATTGTCCTGTAAGACTCACTTCAATTACAGATTGTGCTCAGTATTA
AACTTTGCTAGTACTTTCAGGATGCAGTCAATCAAGAGGCAGGGAAAGGTCTGTCAGCATC
CACAGCCTCCTTTTCAAATTGGACACTTAGTCTCTGGTCCGAATAATAGGTGCCCCCAGTG
TCACCTCACACAATGGGGTATACACAGTTTTTAAAAATTTATTTTCAGCTGGGCACAGTAG
CTCACACCTAAAATCCCAGCACTTTGGGAGGCTGAGGCAGGTGGATCACCTGAGGTCAGGA
GTTCAAGACCAGCCTGGCCAACGTGGCAAAATCCTGTCTCTACTAAAAATACAAAAATTAA
CCG

FIG. 2E

SEQ ID NO: 5

CAGTTTACTCACCAGGGATTCAGAGGCAGCACTGCTGAACCCTGAGCCCTTGGCACATCAG
GTTGGCTGTCAGAAGTCGGCCTTTGTACATACACAGTTCCCTTGTGAGGCCCAGCTGCGTG
TCCTAGGAGCGGGGCCTCTCTCCACAGCAGAGCTCAGCCTCTCAAGTGTATGGACAGCACG
GGTGCCTGATGGGTGGATTTAGCCATGAGTTGAAGGTGGCTTGGGGAGAATGAGAGTTCTA
GAGATAGGGAGAAGGGGTTGCCAATAGGAGAGTGGAATTCCTGAGCACCTCGTCACAGGCA
GCCGACAGAACATGAGCCGCAGGGCCCAGGCTATTTATACCTCGCCTGTCACTATCAGGGT
CCCCACAGCTCCCCCCACCTCCAGCCACACACAGCAGGTCCTTTTGCTCTTTCTGGTCCCT
TCTCTACTCCTCCCCCTCCCTACCTAA

FIG. 2F

SEQ ID NO: 6

CCCTTTCCCTGGCAGGATCTGCCCTGTGGCCCAAATGGGCATGTTGCCCAGGGGGCTCCCT
GGCACTATGGGGGAAGAGTCTCTCCTTCCCCTCTTATCATCTCAGTTGAGTCAGACTTGGG
GGAGGGGGATACACAGTGTGAGTCACTGGGTACCCTTTTCCTGAGCTCAGCTTCATACCGA
GGCGATGAGGCCAAACGGGCTGGTGACAGGGACACTGAGTCAGGGGCAGGGGCCCCGGTCT
TACTCCTGGGCCTCTGGATTTGGGCCCTACATGAGGCTTTTCTATCTGTAAAGTCAAGCAA
TGGCTGGGAGGCACACACAACCCCCCGCCCCCCCGCAGGCTTCTCCTTCATTGGCCCGGGC
AAGGTCCCTGCTTCCTCTCAGGCCGTCTCTGCACAAGCACACACACTTCCCTTCCCTGTCC
ACAGGTGGACAATGCCCTGGGCTAGG

FIG. 6
A
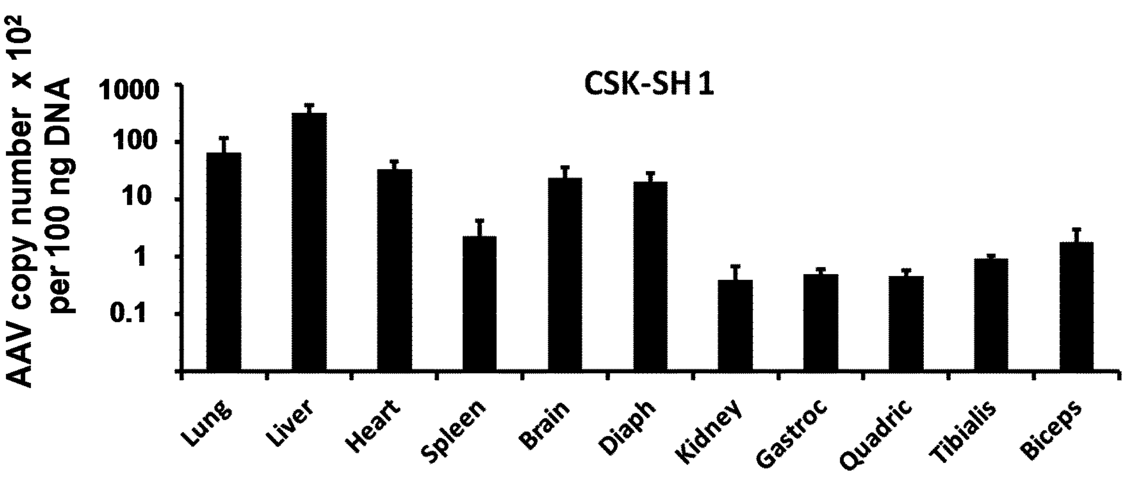
B
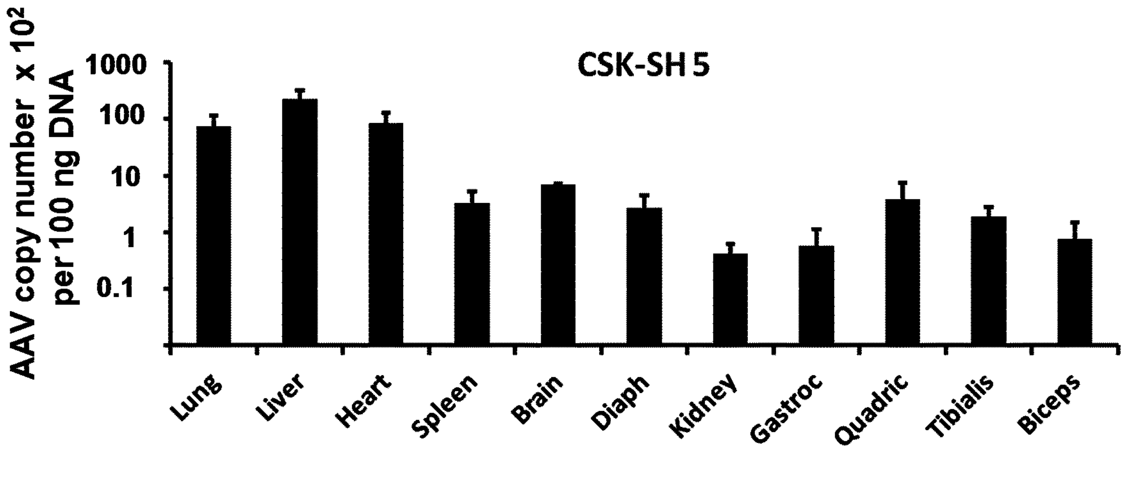

FIG. 7A

SEQ ID NO: 7

CTCACTCCCCGCCCAGGCAGCAAGGAGCCCACACCCTCATGCCCCTCAGCTTCAGCCCCCA
CCTCCAGGAGGCCCTACCCACGCTCATGACCTTGCTATTCTGGGCCTTGTGTCCTGTAGGG
AGATGGACAGGAGACAGCTGGGCTTCCAGGCCACCCAGGCGGGGGGCTAGCCGAGGGAAGC
CTGCTGGCTCTCCTGCTTGCTCTAATTTCTGGGGCTCCCCAAACCTTGGCCTCAGGAGACT
GGGGATAGGACCGGCCTTGAAAGTGGGGGAAGCTTTGGAGAGCCGGGTGCTGGGTTCTTAG
TGAGATGGCCAGTGAAGGCTGTGGTGCCCCGAGGTAAGCAGGGCCTGATCCCCTCCTAATC
TTCCAGCAGCAACTGGTGCTCTGAGGCTCCCCCTCCCCCAGCCCTGCCAGCCTTCAGGGAC
CTGCCTTCCAAAGATGGGCAGGGGAGGGGGACGAGGACACCCACCCACTCCTCAGACCAGC
ATGTCTT

FIG. 7B

SEQ ID NO: 8

CCCTCCAGATGGGTTTCCTGGAATCTAGATTTCCCAGGTTCCAAAGGACACCCGAGTCTCA
TGCCTGGAACTCAGTGAGACTAATTCACCTCTCCTCTGCCCTAATCTTCATCTCCAGCCAG
AAGCCAACAGATCCCAGGGGACTGGAGCCACAGGGGCTGCACCTGTTTACCGGGTATTTTT
AGGATGGTTGATGAACACATAATACCCACCCTATAGTCAGAGAAAGACAATGCCTGCTATG
TTAATCCTGTGGCTATTATAGTCTGTCATCTCATGGGTTGGGGCAGGACACTGACCCTCTC
AGAGGCCAGAGAGAGGCCTCGCAAGCAGGAGGTTAGGGA

FIG. 7C

SEQ ID NO: 9

ATGGAGACAATCCATGAATTCCTGAGATGCTTGGCTGGTATTAGATTTTATGGGCAGCTGC
TTATTCTTAGGGCTCTGCTTCTCCAAAGACACTGAGGAAGTCCAAAGGAAACACCAGCTGG
CGAAGAGCCACCTCCAGGCCCATCTGTCCATCATCAGCCTCCAGGAATGCCAGTGTCCAGA
GGGCACCAGGTCTGCGTCTGTCTCCCTGGGATGTGCCTTGTCCTTGGTGGGCATTTGGCAG
TGATCATGCCTCCCTGTCTCCCTCAGAGATCCAACTGTCCCCATTGTGGGGCCCTACCTTC
CAAGGCCGGTTTACACCTCCTGCCAAGCTCCGGGGCCTGCCCCCAGCCTGCCTCACTGACA
AATGCCAGACCAAGGGGTCCCACGTCAGGCAAGAGGCCTCAGCCTGTGCTCTGACACCCCT
CAG

FIG. 7D

SEQ ID NO: 10

TTCTGAGTCCTCTAAGGTCCCTCACTCCCAACTCAGCCCCATGTCCTGTCAATTCCCACTC
AGTGTCTGATCTCCTTCTCCTCACCTTTCCCATCTCCCGTTTGACCCAAGCTTCCTGAGCT
CTCCTCCCATTCCCCTTTTTGGAGTCCTCCTCCTCTCCCAGAACCCAGTAATAAGTGGGCT
CCTCCCTGGCCTGGACCCCCGTGGTAACCCTATAAGGCGAGGCAGCTGCTGTCTGAGGCAG
GGAGGGGCTGGTGTGGGAGGCTAAGGGCAGCTGCTAAGTTTAGGGTGGCTCCTTCTCTCTT
CTTAGAGACAACAGGTGGCTGGGGCCTCAGTGCCCAGAAAAGAAAATGTCTTAGAGGTATC
GGCATGGGCCTGGAGGAGGGGGACAGGGCAGGGGGAGGCATCTTCCTCAGGACATCGGGT
CCTAGAGG

FIG. 7E

SEQ ID NO: 11

GACTAGGAATAAATCACATATCCTCAATCCCTGGACAACTTGTTTACTTCTAGTGTTAGTT
TTTTCTTAAAAAAAAAATTGAAATCATTCTGAGGCTGGAATACTTTGGACATGCCCAGCAG
TTCCTGGCAGTTCCCACAGAAGCATTACCTCATGACTGGAGTGGGTAAAGCATACTGTGGG
CTATGGATAAGACTGACATTAACCACAAGCATGTTTGGCAGCAGACTGGTGCTTTACAAGC
TCCATGTTCAGCAGGAGCTGCAAAGTGTTCCTCCAAACCAATATTTGTCATTCTTGGATTC
TATTTAGGAGGTCCTGTTACTCACATGTTTCAATATCAGCAGAAGCCAGTTTCCCTGTGGT
ACCGAAGTGGATCCTGATGAATTTACCCTTGTAAGTAAAAAAAATGATGTTATACCCAAAG
CTTGAAGTACGTAGTGGGGATGCCACTGAAATAATTCAGACATGCTT

FIG. 7F

SEQ ID NO: 12

GTGCTCATAGCTCCACCTTTTGTTCCTAATATGGTCTTTCCAGCTCCCTCCACCCCATCAT
TGTTCTCCTGGGGGAACACAGGGTGAGACGCTTTGATGAACTGACATCACCAGCAAAAAAA
ATATCTAGCAACAGCTGAGGCTGATTTAGACAATGGAAAGTGGGGGAGGGAAGAGGTTCT
CCCTGACCCTGAAACTTTCCACTCATTCTGGGCAGCTCTATGGATGTTTTAAAAGAAGAGG
AAGAGGGGAGGGAAGAACATTGAAATAGAGAAGTGTACTTTGGCAATTCTAGGTTGGCAGT
TTGCATCCAGGGGGTCCTGGTTGCCTTTCAGCTTCCCGTTTCACTCTCCCCCAGACTGTGT
TGAATGCTGGTCAAACTCCGTTAGTTGAGTTTTAGCTTTTGATTCCTGGTATTCAAGGAGC
TTGGGCACAGGGAAGAGGGGAGGTCACTCATGATCCTTAACAATTCTCCCAGATCCCCAGA
TCAAATTGCTGTGCTATTCTGGGAGTCTCCG

FIG. 7G

SEQ ID NO: 13

ATCGTGTGTCAGAGGTTTGTGTCAGCTTCCCAGCAAGGGAACCAGAAAGGAAAAGGAACCG
GTTCCTCATGCTTCCTAGGGGAATGCATGCATATCTGAAGAGAAGGGAATCTTATATAAGG
CTGTTTAGCTAAGGGCAGCCACCAGCCAGGTGAGCCTTACAGAAGCACAGGGCTGGGTGTC
TGCAGTTCCCTAGCAGATTAACCTGGGTCACAGTGACTCAGAGCTCCAGCATGCGAGTTCC
AGGTGTGGAACTGAGCAAGTACAGATCTGCTTTTGCTCCACTTGGGAGTATTTTTCCTTCT
TAGTGAGCATGGGCAGCCTCCTGGCCAGGGAAGTCTGGCACTGTCTGGGCCTGACAGGGAA
ACCCTG

FIG. 13
A
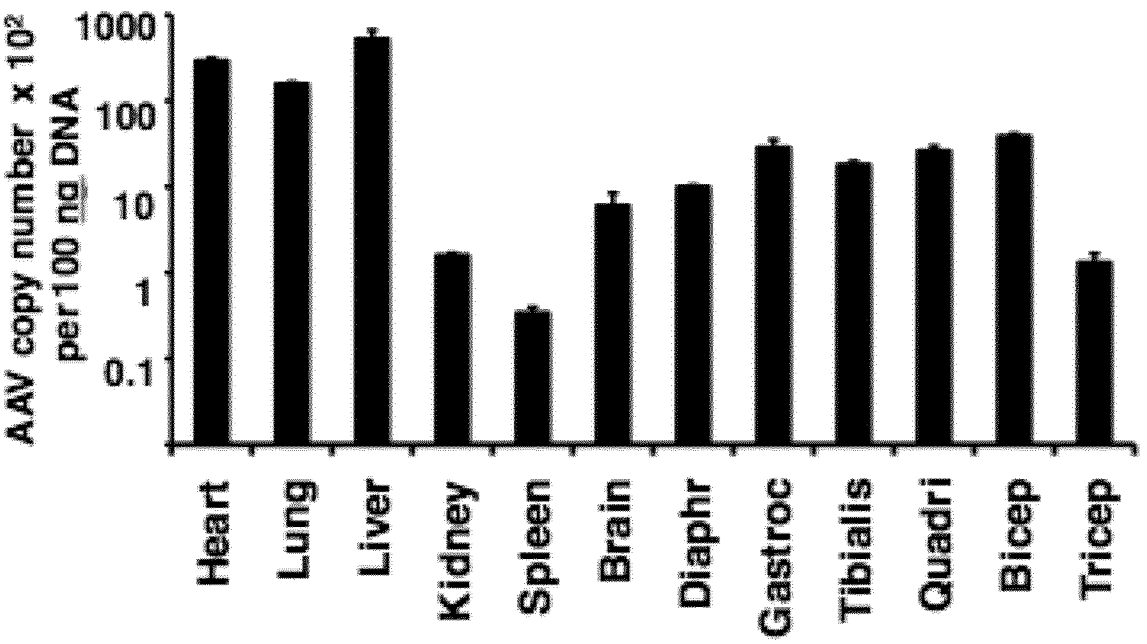
B
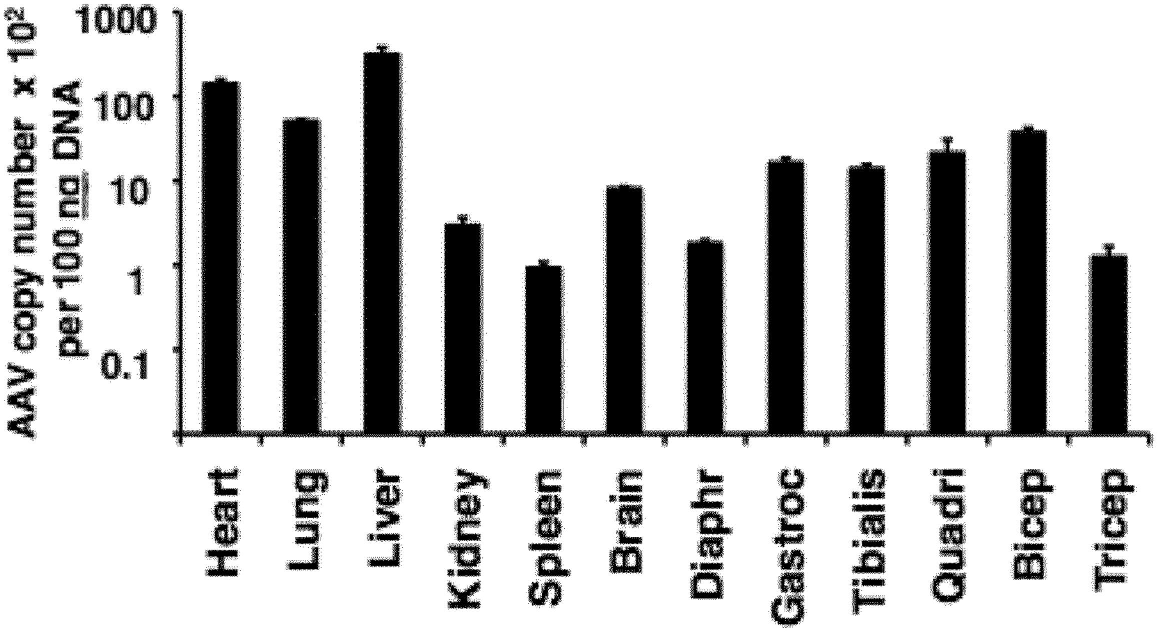

FIG. 16B

SEQ ID NO:44

CCTGCAGGCAGCTGCGCGCTCGCTCGCTCACTGAGGCCGCCCGGGCAAAGCCCGGGCGTCG
GGCGACCTTTGGTCGCCCGGCCTCAGTGAGCGAGCGAGCGCGCAGAGAGGGAGTGGCCAAC
TCCATCACTAGGGGTTCCTCGTACGTTCTGAGTCCTCTAAGGTCCCTCACTCCCAACTCAG
CCCCATGTCCTGTCAATTCCCACTCAGTGTCTGATCTCCTTCTCCTCACCTTTCCCATCTC
CCGTTTGACCCAAGCTTCCTGAGCTCTCCTCCCATTCCCCTTTTTGGAGTCCTCCTCCTCT
CCCAGAACCCAGTAATAAGTGGGCTCCTCCCTGGCCTGGACCCCCGTGGTAACCCTATAAG
GCGAGGCAGCTGCTGTCTGAGGCAGGGAGGGGCTGGTGTGGGAGGCTAAGGGCAGCTGCTA
AGTTTAGGGTGGCTCCTTCTCTCTTCTTAGAGACAACAGGTGGCTGGGGCCTCAGTGCCCA
GAAAAGAAAATGTCTTAGAGGTATCGGCATGGGCCTGGAGGAGGGGGGACAGGGCAGGGGG
AGGCATCTTCCTCAGGACATCGGGTCCTAGAGGGACCTTGCTTCCTAGCTGGGCCTTTCCT
TCTCCTCTATAAATACCAGCTCTGGTATTTCGCCTTGGCAGCTGTTGCTGCTAGGGAGACG
GCTGGCTTGACATGCATCTCCTGACAAAACACAAACCCGTGGTGTGAGTGGGTGTGGGCGG
TGTGAGTAGGGGGATGAATCAGAGAGGGGGCGAGGGAGACAGGGGCGCAGGAGTCAGGCAA
AGGCGATGCGGGGGTGCGACTACACGCAGTTGGAAACAGTCGTCAGAAGATTCTGGAAACT
ATCTTGCTGGCTATAAACTTGAGGGAAGCAGAAGGCCAACATTCCTCCCAAGGGAAACTGA
GGCTCAGAGTTAAAACCCAGGTATCAGTGATATGCATGTGCCCCGGCCAGGGTCACTCTCT
GACTAACCGGTACCTACCCTACAGGCCTACCTAGAGACTCTTTTGAAAGGATGGTAGAGAC
CTGTCCGGGCTTTGCCCACAGTCGTTGGAAACCTCAGCATTTTCTAGGCAACTTGTGCGAA
TAAAACACTTCGGGGGTCCTTCTTGTTCATTCCAATAACCTAAAACCTCTCCTCGGAGAAA
ATAGGGGGCCTCAAACAAACGAAATTCTCTAGCCCGCTTTCCCCAGGATAAGGCAGGCATC
CAAATGGAAAAAAAGGGGCCGGCCGGGGGTCTCCTGTCAGCTCCTTGCCCTGTGAAACCCA
GCAGGCCTGCCTGTCTTCTGTCCTCTTGGGGCTGTCCAGGGGCGCAGGCCTCTTGCGGGGG
AGCTGGCCTCCCCGCCCCCTCGCCTGTGGCCGCCCTTTTCCTGGCAGGACAGAGGGATCCT
GCAGCTGTCAGGGGAGGGGCGCCGGGGGGTGATGTCAGGAGGGCTACAAATAGTGCAGACA
GCTAAGGGGCTCCGTCACCCATCTTCACATCCACTCCAGCCGGCTGCCCGCCCGCTGCCTC
CTCTGTGCGTCCGCCCAGCCAGCCTCGTCCACGCCGCCACCTCTAGAAAGAGGTAAGGGTT
TAAGGGATGGTTGGTTGGTGGGGTATTAATGTTTAATTACCTGGAGCACCTGCCTGAAATC
ACTTTTTTTCAGGTTGGACGCGTGCCACCATGCTGTGGTGGGAGGAAGTGGAGGACTGCTA
CGAGAGAGAGGACGTGCAGAAGAAAACCTTCACCAAGTGGGTGAACGCCCAGTTCAGCAAG
TTCGGCAAGCAGCACATCGAGAACCTGTTCAGCGACCTGCAGGATGGCAGGAGACTGCTGG
ATCTGCTGGAGGGACTGACCGGCCAGAAGCTGCCCAAGGAGAAGGGCAGCACCAGAGTGCA
CGCCCTGAACAACGTGAACAAGGCCCTGAGAGTGCTGCAGAACAACAACGTGGACCTGGTG
AATATCGGCAGCACCGACATCGTGGACGGCAACCACAAGCTGACCCTGGGCCTGATCTGGA
ACATCATCCTGCACTGGCAGGTGAAGAACGTGATGAAGAACATCATGGCCGGCCTGCAGCA
GACCAACAGCGAGAAGATCCTGCTGAGCTGGGTGAGGCAGAGCACCAGAAACTACCCCCAG
GTGAACGTGATCAACTTCACCACCTCCTGGAGCGACGGCCTGGCCCTGAACGCCCTGATCC
ACAGCCACAGACCCGACCTGTTCGACTGGAACAGCGTGGTGTGTCAGCAGAGCGCCACCCA
GAGACTGGAGCACGCCTTCAACATCGCCAGATACCAGCTGGGCATCGAGAAGCTGCTGGAC
CCCGAGGACGTGGACACCACCTACCCCGACAAGAAAAGCATCCTGATGTATATTACCTCTC
TGTTTCAGGTGCTGCCCCAGCAGGTGTCCATCGAGGCCATCCAGGAAGTGGAAATGCTGCC
CAGGCCCCCCACCGTGTCCCTGGCCCAGGGCTATGAGAGAACCAGCAGCCCCAAGCCCAGA
TTCAAGAGCACCGTGTCCCTGGCCCAGGGCTATGAGAGAACCAGCAGCCCCAAGCCCAGAT
TCAAGAGCTACGCCTACACCCAGGCCGCCTACGTGACCACCTCCGACCCCACCAGAAGCCC
CTTCCCCAGCCAGCACCTGGAGGCCCCCGAGGACAAGAGCTTCGGCAGCAGCCTGATGGAG

FIG. 16B (continued)

AGCGAAGTGAACCTGGACAGATACCAGACCGCCCTGGAGGAAGTGCTGTCTTGGCTGCTGT
CCGCCGAGGACACCCTGCAGGCCCAGGGCGAGATCAGCAACGACGTGGAAGTGGTGAAGGA
CCAGTTCCACACCCACGAGGGCTACATGATGGATCTGACCGCCCACCAGGGCAGAGTGGGC
AATATCCTGCAGCTGGGCAGCAAGCTGATCGGCACCGGCAAGCTGAGCGAGGACGAGGAGA
CCGAAGTGCAGGAGCAGATGAACCTGCTGAACAGCAGATGGGAGTGCCTGAGAGTGGCCAG
CATGGAGAAGCAGAGCAACCTGCACCGCGTGCTGATGGACCTGCAGAACCAGAAGCTGAAG
GAGCTGAACGACTGGCTGACCAAGACCGAGGAGCGGACCAGAAAGATGGAGGAGGAGCCCC
TGGGCCCCGACCTGGAGGACCTGAAGAGACAGGTGCAGCAGCACAAAGTGCTGCAGGAGGA
CCTGGAACAGGAGCAGGTGCGCGTGAACAGCCTGACCCACATGGTGGTCGTGGTGGACGAG
AGCAGCGGCGACCACGCCACAGCCGCCCTGGAAGAGCAGCTGAAAGTGCTGGGCGACAGAT
GGGCCAACATCTGCCGGTGGACCGAGGACAGATGGGTGCTGCTGCAGGACATCCTGCTGAA
GTGGCAGAGACTGACAGAGGAGCAGTGCCTGTTTAGCGCCTGGCTGAGCGAGAAGGAGGAC
GCCGTGAACAAGATCCACACCACCGGCTTCAAGGACCAGAACGAGATGCTGAGCAGCCTGC
AGAAGCTGGCCGTGCTGAAGGCCGATCTGGAGAAGAAAAAGCAGAGCATGGGCAAGCTGTA
CTCCCTGAAGCAGGACCTGCTGTCCACCCTGAAGAACAAGAGCGTGACCCAGAAAACCGAG
GCCTGGCTGGACAATTTCGCCCGGTGCTGGGACAATCTGGTGCAGAAACTGGAGAAGAGCA
CCGCCCAGATCAGCCAGGCCGTGACCACCACCCAGCCCAGCCTGACACAGACCACCGTGAT
GGAGACCGTGACCACAGTGACCACCAGGGAGCAGATCCTGGTGAAGCACGCCCAGGAGGAG
CTGCCCCCTCCCCCCCCTCAGAAGAAGCGGCAGATCACAGTGGACACCCTGGAGAGACTGC
AGGAGCTGCAGGAAGCCACCGACGAGCTGGACCTGAAGCTGAGACAGGCCGAAGTGATCAA
GGGCAGCTGGCAGCCTGTGGGCGATCTGCTGATCGACAGCCTGCAGGACCACCTGGAGAAA
GTGAAGGCCCTGCGGGGCGAGATCGCCCCCCTGAAGGAGAATGTGAGCCACGTGAACGACC
TGGCCAGACAGCTGACCACCCTGGGCATCCAGCTGAGCCCCTACAATCTGAGCACCCTGGA
AGATCTGAACACCCGGTGGAAACTGCTGCAGGTGGCCGTGGAGGATAGAGTGAGGCAGCTG
CACGAGGCCCACAGAGACTTCGGCCCTGCCTCCCAGCACTTCCTGAGCACCAGCGTGCAGG
GCCCCTGGGAGAGAGCCATCTCCCCCAACAAAGTGCCCTACTACATCAACCACGAGACCCA
GACCACCTGCTGGGACCACCCTAAGATGACCGAGCTGTACCAGAGCCTGGCCGACCTGAAC
AATGTGCGGTTCAGCGCCTACAGAACCGCCATGAAGCTGCGGAGACTGCAGAAGGCCCTGT
GCCTGGACCTGCTGAGCCTGAGCGCCGCCTGCGACGCCCTGGACCAGCACAACCTGAAGCA
GAACGACCAGCCCATGGACATTCTGCAGATCATCAACTGCCTGACCACCATCTACGATCGG
CTGGAGCAGGAGCACAACAACCTGGTGAACGTGCCCCTGTGCGTGGACATGTGCCTGAATT
GGCTGCTGAACGTGTACGACACCGGCAGGACCGGCAGAATCAGAGTGCTGTCCTTCAAGAC
CGGCATCATCAGCCTGTGCAAGGCCCACCTGGAGGATAAGTACCGCTACCTGTTCAAGCAG
GTGGCCAGCAGCACCGGCTTCTGCGATCAGAGGAGACTGGGCCTGCTGCTGCACGATAGCA
TCCAGATCCCTAGGCAGCTGGGCGAAGTGGCCAGCTTTGGCGGCAGCAACATCGAGCCCTC
TGTGAGGAGCTGCTTCCAGTTCGCCAACAACAAGCCCGAGATCGAGGCCGCCCTGTTCCTG
GATTGGATGAGGCTGGAGCCCCAGAGCATGGTGTGGCTGCCTGTGCTGCACAGAGTGGCCG
CCGCCGAGACCGCCAAGCACCAGGCCAAGTGCAACATCTGCAAGGAGTGCCCCATCATCGG
CTTCCGGTACAGGAGCCTGAAGCACTTCAACTACGACATCTGCCAGAGCTGCTTTTTCAGC
GGCAGAGTGGCCAAGGGCCACAAGATGCACTACCCCATGGTGGAGTACTGCACCCCCACCA
CCTCCGGCGAGGATGTGAGAGACTTCGCCAAAGTGCTGAAGAATAAGTTCCGGACCAAGCG
GTACTTTGCCAAGCACCCCAGGATGGGCTACCTGCCCGTGCAGACCGTGCTGGAGGGCGAC
AACATGGAGACCGACACCATGTGATGATGACTCGAGAATAAAAGATCTTTATTTTCATTAG
ATCTGTGTGTTGGTTTTTTGTGTGAGGAACCCCTAGTGATGGAGTTGGCCACTCCCTCTCT
GCGCGCTCGCTCGCTCACTGAGGCCGGGCGACCAAAGGTCGCCCGACGCCCGGGCTTTGCC
CGGGCGGCCTCAGTGAGCGAGCGAGCGCGCAGCTGCCTGCAGGGGCGCCTGATGCGGTATT
TTCTCCTTACGCATCTGTGCGGTATTTCACACCGCATACGTCAAAGCAACCATAGTACGCG
CCCTGTAGCGGCGCATTAAGCGCGGCGGGTGTGGTGGTTACGCGCAGCGTGACCGCTACAC
TTGCCAGCGCCCTAGCGCCCGCTCCTTTCGCTTTCTTCCCTTCCTTTCTCGCCACGTTCGC

FIG. 16B (continued)

CGGCTTTCCCCGTCAAGCTCTAAATCGGGGGCTCCCTTTAGGGTTCCGATTTAGTGCTTTA
CGGCACCTCGACCCCAAAAAACTTGATTTGGGTGATGGTTCACGTAGTGGGCCATCGCCCT
GATAGACGGTTTTTCGCCCTTTGACGTTGGAGTCCACGTTCTTTAATAGTGGACTCTTGTT
CCAAACTGGAACAACACTCAACCCTATCTCGGGCTATTCTTTTGATTTATAAGGGATTTTG
CCGATTTCGGCCTATTGGTTAAAAAATGAGCTGATTTAACAAAAATTTAACGCGAATTTTA
ACAAAATATTAACGTTTACAATTTTATGGTGCACTCTCAGTACAATCTGCTCTGATGCCGC
ATAGTTAAGCCAGCCCCGACACCCGCCAACACCCGCTGACGCGCCCTGACGGGCTTGTCTG
CTCCCGGCATCCGCTTACAGACAAGCTGTGACCGTCTCCGGGAGCTGCATGTGTCAGAGGT
TTTCACCGTCATCACCGAAACGCGCGAGACGAAAGGGCCTCGTGATACGCCTATTTTTATA
GGTTAATGTCATGATAATAATGGTTTCTTAGACGTCAGGTGGCACTTTTCGGGGAAATGTG
CGCGGAACCCCTATTTGTTTATTTTTCTAAATACATTCAAATATGTATCCGCTCATGAGAC
AATAACCCTGATAAATGCTTCAATAATATTGAAAAAGGAAGAGTATGAGTATTCAACATTT
CCGTGTCGCCCTTATTCCCTTTTTTGCGGCATTTTGCCTTCCTGTTTTTGCTCACCCAGAA
ACGCTGGTGAAAGTAAAAGATGCTGAAGATCAGTTGGGTGCACGAGTGGGTTACATCGAAC
TGGATCTCAACAGCGGTAAGATCCTTGAGAGTTTTCGCCCCGAAGAACGTTTTCCAATGAT
GAGCACTTTTAAAGTTCTGCTATGTGGCGCGGTATTATCCCGTATTGACGCCGGGCAAGAG
CAACTCGGTCGCCGCATACACTATTCTCAGAATGACTTGGTTGAGTACTCACCAGTCACAG
AAAAGCATCTTACGGATGGCATGACAGTAAGAGAATTATGCAGTGCTGCCATAACCATGAG
TGATAACACTGCGGCCAACTTACTTCTGACAACGATCGGAGGACCGAAGGAGCTAACCGCT
TTTTTGCACAACATGGGGGATCATGTAACTCGCCTTGATCGTTGGGAACCGGAGCTGAATG
AAGCCATACCAAACGACGAGCGTGACACCACGATGCCTGTAGCAATGGCAACAACGTTGCG
CAAACTATTAACTGGCGAACTACTTACTCTAGCTTCCCGGCAACAATTAATAGACTGGATG
GAGGCGGATAAAGTTGCAGGACCACTTCTGCGCTCGGCCCTTCCGGCTGGCTGGTTTATTG
CTGATAAATCTGGAGCCGGTGAGCGTGGGTCTCGCGGTATCATTGCAGCACTGGGGCCAGA
TGGTAAGCCCTCCCGTATCGTAGTTATCTACACGACGGGGAGTCAGGCAACTATGGATGAA
CGAAATAGACAGATCGCTGAGATAGGTGCCTCACTGATTAAGCATTGGTAACTGTCAGACC
AAGTTTACTCATATATACTTTAGATTGATTTAAAACTTCATTTTTAATTTAAAAGGATCTA
GGTGAAGATCCTTTTTGATAATCTCATGACCAAAATCCCTTAACGTGAGTTTTCGTTCCAC
TGAGCGTCAGACCCCGTAGAAAAGATCAAAGGATCTTCTTGAGATCCTTTTTTTCTGCGCG
TAATCTGCTGCTTGCAAACAAAAAAACCACCGCTACCAGCGGTGGTTTGTTTGCCGGATCA
AGAGCTACCAACTCTTTTTCCGAAGGTAACTGGCTTCAGCAGAGCGCAGATACCAAATACT
GTCCTTCTAGTGTAGCCGTAGTTAGGCCACCACTTCAAGAACTCTGTAGCACCGCCTACAT
ACCTCGCTCTGCTAATCCTGTTACCAGTGGCTGCTGCCAGTGGCGATAAGTCGTGTCTTAC
CGGGTTGGACTCAAGACGATAGTTACCGGATAAGGCGCAGCGGTCGGGCTGAACGGGGGGT
TCGTGCACACAGCCCAGCTTGGAGCGAACGACCTACACCGAACTGAGATACCTACAGCGTG
AGCTATGAGAAAGCGCCACGCTTCCCGAAGGGAGAAAGGCGGACAGGTATCCGGTAAGCGG
CAGGGTCGGAACAGGAGAGCGCACGAGGGAGCTTCCAGGGGGAAACGCCTGGTATCTTTAT
AGTCCTGTCGGGTTTCGCCACCTCTGACTTGAGCGTCGATTTTTGTGATGCTCGTCAGGGG
GGCGGAGCCTATGGAAAAACGCCAGCAACGCGGCCTTTTTACGGTTCCTGGCCTTTTGCTG
GCCTTTTGCTCACATGT

FIG. 16D

SEQ ID NO:45

CCTGCAGGCAGCTGCGCGCTCGCTCGCTCACTGAGGCCGCCCGGGCAAAGCCCGGGCGTCG
GGCGACCTTTGGTCGCCCGGCCTCAGTGAGCGAGCGAGCGCGCAGAGAGGGAGTGGCCAAC
TCCATCACTAGGGGTTCCTCGTACGTTCTGAGTCCTCTAAGGTCCCTCACTCCCAACTCAG
CCCCATGTCCTGTCAATTCCCACTCAGTGTCTGATCTCCTTCTCCTCACCTTTCCCATCTC
CCGTTTGACCCAAGCTTCCTGAGCTCTCCTCCCATTCCCCTTTTTGGAGTCCTCCTCCTCT
CCCAGAACCCAGTAATAAGTGGGCTCCTCCCTGGCCTGGACCCCCGTGGTAACCCTATAAG
GCGAGGCAGCTGCTGTCTGAGGCAGGGAGGGGCTGGTGTGGGAGGCTAAGGGCAGCTGCTA
AGTTTAGGGTGGCTCCTTCTCTCTTCTTAGAGACAACAGGTGGCTGGGGCCTCAGTGCCCA
GAAAAGAAAATGTCTTAGAGGTATCGGCATGGGCCTGGAGGAGGGGGACAGGGCAGGGGG
AGGCATCTTCCTCAGGACATCGGGTCCTAGAGGGACCTTGCTTCCTAGCTGGGCCTTTCCT
TCTCCTCTATAAATACCAGCTCTGGTATTTCGCCTTGGCAGCTGTTGCTGCTAGGGAGACG
GCTGGCTTGACATGCATCTCCTGACAAAACACAAACCCGTGGTGTGAGTGGGTGTGGGCGG
TGTGAGTAGGGGGATGAATCAGAGAGGGGGCGAGGGAGACAGGGGCGCAGGAGTCAGGCAA
AGGCGATGCGGGGGTGCGACTACACGCAGTTGGAAACAGTCGTCAGAAGATTCTGGAAACT
ATCTTGCTGGCTATAAACTTGAGGGAAGCAGAAGGCCAACATTCCTCCCAAGGGAAACTGA
GGCTCAGAGTTAAAACCCAGGTATCAGTGATATGCATGTGCCCCGGCCAGGGTCACTCTCT
GACTAACCGGTACCTACCCTACAGGCCTACCTAGAGACTCTTTTGAAAGGATGGTAGAGAC
CTGTCCGGGCTTTGCCCACAGTCGTTGGAAACCTCAGCATTTTCTAGGCAACTTGTGCGAA
TAAAACACTTCGGGGGTCCTTCTTGTTCATTCCAATAACCTAAAACCTCTCCTCGGAGAAA
ATAGGGGGCCTCAAACAAACGAAATTCTCTAGCCCGCTTTCCCCAGGATAAGGCAGGCATC
CAAATGGAAAAAAAGGGGCCGGCCGGGGGTCTCCTGTCAGCTCCTTGCCCTGTGAAACCCA
GCAGGCCTGCCTGTCTTCTGTCCTCTTGGGGCTGTCCAGGGGCGCAGGCCTCTTGCGGGGG
AGCTGGCCTCCCCGCCCCCTCGCCTGTGGCCGCCCTTTTCCTGGCAGGACAGAGGGATCCT
GCAGCTGTCAGGGGAGGGGCGCCGGGGGGTGATGTCAGGAGGGCTACAAATAGTGCAGACA
GCTAAGGGGCTCCGTCACCCATCTTCACATCCACTCCAGCCGGCTGCCCGCCCGCTGCCTC
CTCTGTGCGTCCGCCCAGCCAGCCTCGTCCACGCCGCCACCTCTAGAAAGAGGTAAGGGTT
TAAGGGATGGTTGGTTGGTGGGGTATTAATGTTTAATTACCTGGAGCACCTGCCTGAAATC
ACTTTTTTTCAGGTTGGACGCGTATGGTCCGCGCGAGGCACCAGCCGGGTGGGCTTTGCCT
CCTGCTGCTGCTGCTCTGCCAGTTCATGGAGGACCGCAGTGCCCAGGCTGGGAACTGCTGG
CTCCGTCAAGCGAAGAACGGCCGCTGCCAGGTCCTGTACAAGACCGAACTGAGCAAGGAGG
AGTGCTGCAGCACCGGCCGGCTGAGCACCTCGTGGACCGAGGAGGACGTGAATGACAACAC
ACTCTTCAAGTGGATGATTTTCAACGGGGGCGCCCCCAACTGCATCCCCTGTAAAGAAACG
TGTGAGAACGTGGACTGTGGACCTGGGAAAAAATGCCGAATGAACAAGAAGAACAAACCCC
GCTGCGTCTGCGCCCCGGATTGTTCCAACATCACCTGGAAGGGTCCAGTCTGCGGGCTGGA
TGGGAAAACCTACCGCAATGAATGTGCACTCCTAAAGGCAAGATGTAAAGAGCAGCCAGAA
CTGGAAGTCCAGTACCAAGGCAGATGTAAAAAGACTTGTCGGGATGTTTTCTGTCCAGGCA
GCTCCACATGTGTGGTGGACCAGACCAATAATGCCTACTGTGTGACCTGTAATCGGATTTG
CCCAGAGCCTGCTTCCTCTGAGCAATATCTCTGTGGGAATGATGGAGTCACCTACTCCAGT
GCCTGCCACCTGAGAAAGGCTACCTGCCTGCTGGGCAGATCTATTGGATTAGCCTATGAGG
GAAAGTGTATCAAAGCAAAGTCCTGTGAAGATATCCAGTGCACTGGTGGGAAAAAATGTTT
ATGGGATTTCAAGGTTGGGAGAGGCCGGTGTTCCCTCTGTGATGAGCTGTGCCCTGACAGT
AAGTCGGATGAGCCTGTCTGTGCCAGTGACAATGCCACTTATGCCAGCGAGTGTGCCATGA
AGGAAGCTGCCTGCTCCTCAGGTGTGCTACTGGAAGTAAAGCACTCCGGATCTTGCAACTC
CATTTCGGAAGACACCGAGGAAGAGGAGGAAGATGAAGACCAGGACTACAGCTTTCCTATA

FIG. 16D (continued)

TCTTCTATTCTAGAGTGGGTCGAGAGGTCCGGCGGCGGAGAGGGCAGAGGAAGTCTTCTAA
CATGCGGTGACGTGGAGGAGAATCCCGGCCCAATGGAAGATGCCAAAAACATTAAGAAGGG
CCCAGCGCCATTCTACCCACTCGAAGACGGGACCGCCGGCGAGCAGCTGCACAAAGCCATG
AAGCGCTACGCCCTGGTGCCCGGCACCATCGCCTTTACCGACGCACATATCGAGGTGGACA
TTACCTACGCCGAGTACTTCGAGATGAGCGTTCGGCTGGCAGAAGCTATGAAGCGCTATGG
GCTGAATACAAACCATCGGATCGTGGTGTGCAGCGAGAATAGCTTGCAGTTCTTCATGCCC
GTGTTGGGTGCCCTGTTCATCGGTGTGGCTGTGGCCCCAGCTAACGACATCTACAACGAGC
GCGAGCTGCTGAACAGCATGGGCATCAGCCAGCCCACCGTCGTATTCGTGAGCAAGAAAGG
GCTGCAAAAGATCCTCAACGTGCAAAAGAAGCTACCGATCATACAAAAGATCATCATCATG
GATAGCAAGACCGACTACCAGGGCTTCCAAAGCATGTACACCTTCGTGACTTCCCATTTGC
CACCCGGCTTCAACGAGTACGACTTCGTGCCCGAGAGCTTCGACCGGGACAAAACCATCGC
CCTGATCATGAACAGTAGTGGCAGTACCGGATTGCCCAAGGGCGTAGCCCTACCGCACCGC
ACCGCTTGTGTCCGATTCAGTCATGCCCGCGACCCCATCTTCGGCAACCAGATCATCCCCG
ACACCGCTATCCTCAGCGTGGTGCCATTTCACCACGGCTTCGGCATGTTCACCACGCTGGG
CTACTTGATCTGCGGCTTTCGGGTCGTGCTCATGTACCGCTTCGAGGAGGAGCTATTCTTG
CGCAGCTTGCAAGACTATAAGATTCAATCTGCCCTGCTGGTGCCCACACTATTTAGCTTCT
TCGCTAAGAGCACTCTCATCGACAAGTACGACCTAAGCAACTTGCACGAGATCGCCAGCGG
CGGGGCGCCGCTCAGCAAGGAGGTAGGTGAGGCCGTGGCCAAACGCTTCCACCTACCAGGC
ATCCGCCAGGGCTACGGCCTGACAGAAACAACCAGCGCCATTCTGATCACCCCCGAAGGGG
ACGACAAGCCTGGCGCAGTAGGCAAGGTGGTGCCCTTCTTCGAGGCTAAGGTGGTGGACTT
GGACACCGGTAAGACACTGGGTGTGAACCAGCGCGGCGAGCTGTGCGTCCGTGGCCCCATG
ATCATGAGCGGCTACGTTAACAACCCCGAGGCTACAAACGCTCTCATCGACAAGGACGGCT
GGCTGCACAGCGGCGACATCGCCTACTGGGACGAGGACGAGCACTTCTTCATCGTGGACCG
GCTGAAGAGCCTGATCAAATACAAGGGCTACCAGGTAGCCCCAGCCGAACTGGAGAGCATC
CTGCTGCAACACCCCAACATCTTCGACGCCGGGGTCGCCGGCCTGCCCGACGACGATGCCG
GCGAGCTGCCCGCCGCAGTCGTCGTGCTGGAACACGGTAAAACCATGACCGAGAAGGAGAT
CGTGGACTATGTGGCCAGCCAGGTTACAACCGCCAAGAAGCTGCGCGGTGGTGTTGTGTTC
GTGGACGAGGTGCCTAAAGGACTGACCGGCAAGTTGGACGCCCGCAAGATCCGCGAGATTC
TCATTAAGGCCAAGAAGGGCGGCAAGATCGCCGTGTAAAATAAAAGATCTTTATTTTCATT
AGATCTGTGTGTTGGTTTTTTGTGTGAGGAACCCCTAGTGATGGAGTTGGCCACTCCCTCT
CTGCGCGCTCGCTCGCTCACTGAGGCCGGGCGACCAAAGGTCGCCCGACGCCCGGGCTTTG
CCCGGGCGGCCTCAGTGAGCGAGCGAGCGCGCAGCTGCCTGCAGGGGCGCCTGATGCGGTA
TTTTCTCCTTACGCATCTGTGCGGTATTTCACACCGCATACGTCAAAGCAACCATAGTACG
CGCCCTGTAGCGGCGCATTAAGCGCGGCGGGTGTGGTGGTTACGCGCAGCGTGACCGCTAC
ACTTGCCAGCGCCCTAGCGCCCGCTCCTTTCGCTTTCTTCCCTTCCTTTCTCGCCACGTTC
GCCGGCTTTCCCCGTCAAGCTCTAAATCGGGGGCTCCCTTTAGGGTTCCGATTTAGTGCTT
TACGGCACCTCGACCCCAAAAAACTTGATTTGGGTGATGGTTCACGTAGTGGGCCATCGCC
CTGATAGACGGTTTTTCGCCCTTTGACGTTGGAGTCCACGTTCTTTAATAGTGGACTCTTG
TTCCAAACTGGAACAACACTCAACCCTATCTCGGGCTATTCTTTTGATTTATAAGGGATTT
TGCCGATTTCGGCCTATTGGTTAAAAAATGAGCTGATTTAACAAAAATTTAACGCGAATTT
TAACAAAATATTAACGTTTACAATTTTATGGTGCACTCTCAGTACAATCTGCTCTGATGCC
GCATAGTTAAGCCAGCCCCGACACCCGCCAACACCCGCTGACGCGCCCTGACGGGCTTGTC
TGCTCCCGGCATCCGCTTACAGACAAGCTGTGACCGTCTCCGGGAGCTGCATGTGTCAGAG
GTTTTCACCGTCATCACCGAAACGCGCGAGACGAAAGGGCCTCGTGATACGCCTATTTTTA
TAGGTTAATGTCATGATAATAATGGTTTCTTAGACGTCAGGTGGCACTTTTCGGGGAAATG
TGCGCGGAACCCCTATTTGTTTATTTTTCTAAATACATTCAAATATGTATCCGCTCATGAG
ACAATAACCCTGATAAATGCTTCAATAATATTGAAAAAGGAAGAGTATGAGTATTCAACAT
TTCCGTGTCGCCCTTATTCCCTTTTTTGCGGCATTTTGCCTTCCTGTTTTTGCTCACCCAG
AAACGCTGGTGAAAGTAAAAGATGCTGAAGATCAGTTGGGTGCACGAGTGGGTTACATCGA

FIG. 16D (continued)

ACTGGATCTCAACAGCGGTAAGATCCTTGAGAGTTTTCGCCCCGAAGAACGTTTTCCAATG
ATGAGCACTTTTAAAGTTCTGCTATGTGGCGCGGTATTATCCCGTATTGACGCCGGGCAAG
AGCAACTCGGTCGCCGCATACACTATTCTCAGAATGACTTGGTTGAGTACTCACCAGTCAC
AGAAAAGCATCTTACGGATGGCATGACAGTAAGAGAATTATGCAGTGCTGCCATAACCATG
AGTGATAACACTGCGGCCAACTTACTTCTGACAACGATCGGAGGACCGAAGGAGCTAACCG
CTTTTTTGCACAACATGGGGGATCATGTAACTCGCCTTGATCGTTGGGAACCGGAGCTGAA
TGAAGCCATACCAAACGACGAGCGTGACACCACGATGCCTGTAGCAATGGCAACAACGTTG
CGCAAACTATTAACTGGCGAACTACTTACTCTAGCTTCCCGGCAACAATTAATAGACTGGA
TGGAGGCGGATAAAGTTGCAGGACCACTTCTGCGCTCGGCCCTTCCGGCTGGCTGGTTTAT
TGCTGATAAATCTGGAGCCGGTGAGCGTGGGTCTCGCGGTATCATTGCAGCACTGGGGCCA
GATGGTAAGCCCTCCCGTATCGTAGTTATCTACACGACGGGGAGTCAGGCAACTATGGATG
AACGAAATAGACAGATCGCTGAGATAGGTGCCTCACTGATTAAGCATTGGTAACTGTCAGA
CCAAGTTTACTCATATATACTTTAGATTGATTTAAAACTTCATTTTTAATTTAAAAGGATC
TAGGTGAAGATCCTTTTTGATAATCTCATGACCAAAATCCCTTAACGTGAGTTTTCGTTCC
ACTGAGCGTCAGACCCCGTAGAAAAGATCAAAGGATCTTCTTGAGATCCTTTTTTTCTGCG
CGTAATCTGCTGCTTGCAAACAAAAAAACCACCGCTACCAGCGGTGGTTTGTTTGCCGGAT
CAAGAGCTACCAACTCTTTTTCCGAAGGTAACTGGCTTCAGCAGAGCGCAGATACCAAATA
CTGTCCTTCTAGTGTAGCCGTAGTTAGGCCACCACTTCAAGAACTCTGTAGCACCGCCTAC
ATACCTCGCTCTGCTAATCCTGTTACCAGTGGCTGCTGCCAGTGGCGATAAGTCGTGTCTT
ACCGGGTTGGACTCAAGACGATAGTTACCGGATAAGGCGCAGCGGTCGGGCTGAACGGGGG
GTTCGTGCACACAGCCCAGCTTGGAGCGAACGACCTACACCGAACTGAGATACCTACAGCG
TGAGCTATGAGAAAGCGCCACGCTTCCCGAAGGGAGAAAGGCGGACAGGTATCCGGTAAGC
GGCAGGGTCGGAACAGGAGAGCGCACGAGGGAGCTTCCAGGGGGAAACGCCTGGTATCTTT
ATAGTCCTGTCGGGTTTCGCCACCTCTGACTTGAGCGTCGATTTTTGTGATGCTCGTCAGG
GGGGCGGAGCCTATGGAAAAACGCCAGCAACGCGGCCTTTTTACGGTTCCTGGCCTTTTGC
TGGCCTTTTGCTCACATGT

SEQUENCE LISTING

```
<160> NUMBER OF SEQ ID NOS: 46

<210> SEQ ID NO 1
<211> LENGTH: 381
<212> TYPE: DNA
<213> ORGANISM: Artificial
<220> FEATURE:
<223> OTHER INFORMATION: Heart and skeletal muscle-specific regulatory
      element 1 (CSk-SH1)

<400> SEQUENCE: 1
```

-continued

```
gttctcctct ataaataccc gctctggtat ttggggttgg cagctgttgc tgccagggag     60

atggttgggt tgacatgcgg ctcctgacaa aacacaaacc cctggtgtgt gtgggcgtgg    120

gtggtgtgag taggggggatg aatcagggag ggggcggggg acccaggggg caggagccac    180

acaaagtctg tgcgggggtg ggagcgcaca tagcaattgg aaactgaaag cttatcagac    240

cctttctgga aatcagccca ctgtttataa acttgaggcc ccaccctcga cagtaccggg    300

gaggaagagg gcctgcacta gtccagaggg aaactgaggc tcagggctag ctcgcccata    360

gacatacatg gcaggcaggc t                                              381


<210> SEQ ID NO 2
<211> LENGTH: 435
<212> TYPE: DNA
<213> ORGANISM: Artificial
<220> FEATURE:
<223> OTHER INFORMATION: Heart and skeletal muscle-specific regulatory
      element 2 (CSk-SH2)

<400> SEQUENCE: 2

cgtctataaa ttccagggaa ggtctctgat tggccctgct cattcccagg cccattcctt     60

gacccagtca ctgaagtcag ggagatgcag taataagact ggctggaatc agggtcttta    120

ggggtggagg gatggggagg aggcacagca tgtcatcaaa ataaggaaat tgcaaaagaa    180

agcttgcagg ctactttgaa tgacaatgag aaagacggtg ctgcctgagt gtgttaagga    240

tccacatggt ctccaaaatc ctccaggagc atacagtcta gtctgggaga tgagacacaa    300

aaataaccag aacacaacag cttgcactga ctcgagggct ggataagaat atctggaact    360

cccccatcta tttcagaagc ttgtctcttg gatgaaaatt agacacttaa tgggaaaggg    420

ctttgaaaag agtgc                                                     435


<210> SEQ ID NO 3
<211> LENGTH: 551
<212> TYPE: DNA
<213> ORGANISM: Artificial
<220> FEATURE:
<223> OTHER INFORMATION: Heart and skeletal muscle-specific regulatory
      element 3 (CSk-SH3)

<400> SEQUENCE: 3

aaaaaataaa aataaaaaat aaaaataaat aaagtggatg gcttagagta tcttttctgt     60

ttagacctga ctaaagctta gacataattg ttagtttagg ctctcagggt aaaatttatt    120

actgtaaatc caaaaaatcc cttcttcttc tttttttttt tttttttggt ccttgaatta    180

aatgctgtca cctccttctt gaaaggagaa actattagtc agatttgaaa atcctcttta    240

tcacccagga aaatcatttt tatggacact ttgtctttct gtagtctgac ttagaagcag    300

cctgtttttg ataggttgaa gttttcatct tgaacacaaa ccctgtttgt gtgtccccta    360

ctccccagtt tgatgtgcca ggcactttgt tctcaagccc agcagctgtt gtgggatgag    420

gggacatttt gcatgcttag ccagcagctg ccagaaacat ttctaatctg gttttggcag    480

gaaataggc acaagtggaa gccaagttaa aagaagctgg aaaaataaac agaataactt    540

tagatgtcac t                                                         551


<210> SEQ ID NO 4
<211> LENGTH: 430
<212> TYPE: DNA
<213> ORGANISM: Artificial
<220> FEATURE:
<223> OTHER INFORMATION: Heart and skeletal muscle-specific regulatory
```

element 4 (CSk-SH4)

<400> SEQUENCE: 4
tgcactgtag actatttatg tttgcatatt tttcaggatt gtgtacagta aaccttaagt 60
gaatacaaag gatccaattg tcctgtaaga ctcacttcaa ttacagattg tgctcagtat 120
taaactttgc tagtactttc aggatgcagt caatcaagag gcagggaaag gtctgtcagc 180
atccacagcc tccttttcaa attggacact tagtctctgg tccgaataat aggtgccccc 240
agtgtcacct cacacaatgg ggtatacaca gtttttaaaa atttattttc agctgggcac 300
agtagctcac acctaaaatc ccagcacttt gggaggctga ggcaggtgga tcacctgagg 360
tcaggagttc aagaccagcc tggccaacgt ggcaaaatcc tgtctctact aaaaatacaa 420
aaattaaccg 430

<210> SEQ ID NO 5
<211> LENGTH: 454
<212> TYPE: DNA
<213> ORGANISM: Artificial
<220> FEATURE:
<223> OTHER INFORMATION: Heart and skeletal muscle-specific regulatory element 5 (CSk-SH5)

<400> SEQUENCE: 5
cagtttactc accagggatt cagaggcagc actgctgaac cctgagccct tggcacatca 60
ggttggctgt cagaagtcgg cctttgtaca tacacagttc ccttgtgagg cccagctgcg 120
tgtcctagga gcggggcctc tctccacagc agagctcagc ctctcaagtg tatggacagc 180
acgggtgcct gatgggtgga tttagccatg agttgaaggt ggcttgggga gaatgagagt 240
tctagagata gggagaaggg gttgccaata ggagagtgga attcctgagc acctcgtcac 300
aggcagccga cagaacatga gccgcagggc ccaggctatt tatacctcgc ctgtcactat 360
cagggtcccc acagctcccc ccacctccag ccacacacag caggtccttt tgctctttct 420
ggtcccttct ctactcctcc ccctccctac ctaa 454

<210> SEQ ID NO 6
<211> LENGTH: 453
<212> TYPE: DNA
<213> ORGANISM: Artificial
<220> FEATURE:
<223> OTHER INFORMATION: Heart and skeletal muscle-specific regulatory element 6 (CSk-SH6)

<400> SEQUENCE: 6
ccctttccct ggcaggatct gccctgtggc ccaaatgggc atgttgccca gggggctccc 60
tggcactatg ggggaagagt ctctccttcc cctcttatca tctcagttga gtcagacttg 120
ggggaggggg atacacagtg tgagtcactg ggtacccttt tcctgagctc agcttcatac 180
cgaggcgatg aggccaaacg ggctggtgac agggacactg agtcaggggc aggggccccg 240
gtcttactcc tgggcctctg gatttgggcc ctacatgagg cttttctatc tgtaaagtca 300
agcaatggct gggaggcaca cacaaccccc cgcccccccg caggcttctc cttcattggc 360
ccgggcaagg tccctgcttc ctctcaggcc gtctctgcac aagcacacac acttcccttc 420
cctgtccaca ggtggacaat gccctgggct agg 453

<210> SEQ ID NO 7
<211> LENGTH: 495
<212> TYPE: DNA
<213> ORGANISM: Artificial

-continued

<220> FEATURE:
<223> OTHER INFORMATION: Skeletal muscle-specific regulatory element 1
(Sk-SH1)

<400> SEQUENCE: 7

```
ctcactcccc gcccaggcag caaggagccc acaccctcat gcccctcagc ttcagccccc     60

acctccagga ggccctaccc acgctcatga ccttgctatt ctgggccttg tgtcctgtag    120

ggagatggac aggagacagc tggcttcca ggccacccag gcgggggct agccgaggga    180

agcctgctgg ctctcctgct tgctctaatt tctggggctc cccaaacctt ggcctcagga    240

gactggggat aggaccggcc ttgaaagtgg gggaagcttt ggagagccgg gtgctgggtt    300

cttagtgaga tggccagtga aggctgtggt gccccgaggt aagcagggcc tgatcccctc    360

ctaatcttcc agcagcaact ggtgctctga ggctccccct cccccagccc tgccagcctt    420

cagggacctg ccttccaaag atgggcaggg gagggggacg aggacaccca cccactcctc    480

agaccagcat gtctt                                                     495
```

<210> SEQ ID NO 8
<211> LENGTH: 344
<212> TYPE: DNA
<213> ORGANISM: Artificial
<220> FEATURE:
<223> OTHER INFORMATION: Skeletal muscle-specific regulatory element 2
(Sk-SH2)

<400> SEQUENCE: 8

```
ccctccagat gggtttcctg gaatctagat ttcccaggtt ccaaaggaca cccgagtctc     60

atgcctggaa ctcagtgaga ctaattcacc tctcctctgc cctaatcttc atctccagcc    120

agaagccaac agatcccagg ggactggagc cacaggggct gcacctgttt accgggtatt    180

tttaggatgg ttgatgaaca cataataccc accctatagt cagagaaaga caatgcctgc    240

tatgttaatc ctgtggctat tatagtctgt catctcatgg gttggggcag gacactgacc    300

ctctcagagg ccagagagag gcctcgcaag caggaggtta ggga                     344
```

<210> SEQ ID NO 9
<211> LENGTH: 430
<212> TYPE: DNA
<213> ORGANISM: Artificial
<220> FEATURE:
<223> OTHER INFORMATION: Skeletal muscle-specific regulatory element 3
(Sk-SH3)

<400> SEQUENCE: 9

```
atggagacaa tccatgaatt cctgagatgc ttggctggta ttagatttta tgggcagctg     60

cttattctta gggctctgct tctccaaaga cactgaggaa gtccaaagga aacaccagct    120

ggcgaagagc cacctccagg cccatctgtc catcatcagc ctccaggaat gccagtgtcc    180

agagggcacc aggtctgcgt ctgtctccct gggatgtgcc ttgtccttgg tgggcatttg    240

gcagtgatca tgcctccctg tctccctcag agatccaact gtccccattg tggggcccta    300

ccttccaagg ccggtttaca cctcctgcca agctccgggg cctgccccca gcctgcctca    360

ctgacaaatg ccagaccaag gggtcccacg tcaggcaaga ggcctcagcc tgtgctctga    420

cacccctcag                                                           430
```

<210> SEQ ID NO 10
<211> LENGTH: 435
<212> TYPE: DNA
<213> ORGANISM: Artificial

<220> FEATURE:
<223> OTHER INFORMATION: Skeletal muscle-specific regulatory element 4
(Sk-SH4)

<400> SEQUENCE: 10
ttctgagtcc tctaaggtcc ctcactccca actcagcccc atgtcctgtc aattcccact 60
cagtgtctga tctccttctc ctcacctttc ccatctcccg tttgacccaa gcttcctgag 120
ctctcctccc attccccttt ttggagtcct cctcctctcc cagaacccag taataagtgg 180
gctcctccct ggcctggacc cccgtggtaa ccctataagg cgaggcagct gctgtctgag 240
gcagggaggg gctggtgtgg gaggctaagg gcagctgcta agtttagggt ggctccttct 300
ctcttcttag agacaacagg tggctggggc ctcagtgccc agaaaagaaa atgtcttaga 360
ggtatcggca tgggcctgga ggaggggga cagggcaggg ggaggcatct tcctcaggac 420
atcgggtcct agagg 435

<210> SEQ ID NO 11
<211> LENGTH: 474
<212> TYPE: DNA
<213> ORGANISM: Artificial
<220> FEATURE:
<223> OTHER INFORMATION: Skeletal muscle-specific regulatory element 5
(Sk-SH5)

<400> SEQUENCE: 11
gactaggaat aaatcacata tcctcaatcc ctggacaact tgtttacttc tagtgttagt 60
tttttcttaa aaaaaaaatt gaaatcattc tgaggctgga atactttgga catgcccagc 120
agttcctggc agttcccaca gaagcattac ctcatgactg gagtgggtaa agcatactgt 180
gggctatgga taagactgac attaaccaca agcatgtttg gcagcagact ggtgctttac 240
aagctccatg ttcagcagga gctgcaaagt gttcctccaa accaatattt gtcattcttg 300
gattctattt aggaggtcct gttactcaca tgtttcaata tcagcagaag ccagtttccc 360
tgtggtaccg aagtggatcc tgatgaattt acccttgtaa gtaaaaaaaa tgatgttata 420
cccaaagctt gaagtacgta gtggggatgc cactgaaata attcagacat gctt 474

<210> SEQ ID NO 12
<211> LENGTH: 519
<212> TYPE: DNA
<213> ORGANISM: Artificial
<220> FEATURE:
<223> OTHER INFORMATION: Skeletal muscle-specific regulatory element 6
(Sk-SH6)

<400> SEQUENCE: 12
gtgctcatag ctccaccttt tgttcctaat atggtctttc cagctccctc caccccatca 60
ttgttctcct gggggaacac agggtgagac gctttgatga actgacatca ccagcaaaaa 120
aaatatctag caacagctga ggctgatttt agacaatgga aagtggggga gggaagaggt 180
tctccctgac cctgaaactt tccactcatt ctgggcagct ctatggatgt tttaaaagaa 240
gaggaagagg ggagggaaga acattgaaat agagaagtgt actttggcaa ttctaggttg 300
gcagtttgca tccagggggt cctggttgcc tttcagcttc ccgtttcact ctcccccaga 360
ctgtgttgaa tgctggtcaa actccgttag ttgagtttta gcttttgatt cctggtattc 420
aaggagcttg ggcacaggga agaggggagg tcactcatga tccttaacaa ttctcccaga 480
tccccagatc aaattgctgt gctattctgg gagtctccg 519

<210> SEQ ID NO 13
<211> LENGTH: 372
<212> TYPE: DNA
<213> ORGANISM: Artificial
<220> FEATURE:
<223> OTHER INFORMATION: Skeletal muscle-specific regulatory element 7
(Sk-SH7)

<400> SEQUENCE: 13
atcgtgtgtc agaggtttgt gtcagcttcc cagcaaggga accagaaagg aaaaggaacc 60
ggttcctcat gcttcctagg ggaatgcatg catatctgaa gagaagggaa tcttatataa 120
ggctgtttag ctaagggcag ccaccagcca ggtgagcctt acagaagcac agggctgggt 180
gtctgcagtt ccctagcaga ttaacctggg tcacagtgac tcagagctcc agcatgcgag 240
ttccaggtgt ggaactgagc aagtacagat ctgcttttgc tccacttggg agtatttttc 300
cttcttagtg agcatgggca gcctcctggc cagggaagtc tggcactgtc tgggcctgac 360
agggaaaccc tg 372

<210> SEQ ID NO 14
<211> LENGTH: 20
<212> TYPE: DNA
<213> ORGANISM: Artificial
<220> FEATURE:
<223> OTHER INFORMATION: Primer

<400> SEQUENCE: 14
cccaccgtcg tattcgtgag 20

<210> SEQ ID NO 15
<211> LENGTH: 21
<212> TYPE: DNA
<213> ORGANISM: Artificial
<220> FEATURE:
<223> OTHER INFORMATION: primer

<400> SEQUENCE: 15
tcagggcgat ggttttgtcc c 21

<210> SEQ ID NO 16
<211> LENGTH: 983
<212> TYPE: DNA
<213> ORGANISM: Artificial
<220> FEATURE:
<223> OTHER INFORMATION: Desmin promoter

<400> SEQUENCE: 16
accttgcttc ctagctgggc ctttccttct cctctataaa taccagctct ggtatttcgc 60
cttggcagct gttgctgcta gggagacggc tggcttgaca tgcatctcct gacaaaacac 120
aaacccgtgg tgtgagtggg tgtgggcggt gtgagtaggg ggatgaatca gagagggggc 180
gagggagaca ggggcgcagg agtcaggcaa aggcgatgcg gggtgcgac tacacgcagt 240 tggaaacagt cgtcagaaga ttctggaaac tatcttgctg gctataaact tgagggaagc 300
agaaggccaa cattcctccc aagggaaact gaggctcaga gttaaaaccc aggtatcagt 360
gatatgcatg tgccccggcc agggtcactc tctgactaac cggtacctac cctacaggcc 420
tacctagaga ctcttttgaa aggatggtag agacctgtcc gggctttgcc cacagtcgtt 480
ggaaacctca gcattttcta ggcaacttgt gcgaataaaa cacttcgggg gtccttcttg 540
ttcattccaa taacctaaaa cctctcctcg gagaaaatag gggcctcaa acaaacgaaa 600 ttctctagcc cgctttcccc aggataaggc aggcatccaa atggaaaaaa aggggccggc 660
cgggggtctc ctgtcagctc cttgccctgt gaaacccagc aggcctgcct gtcttctgtc 720
ctcttggggc tgtccagggg cgcaggcctc ttgcggggga gctggcctcc ccgccccctc 780
gcctgtggcc gccctttttcc tggcaggaca gagggatcct gcagctgtca ggggaggggc 840 gccgggggt gatgtcagga gggctacaaa tagtgcagac agctaagggg ctccgtcacc 900
catcttcaca tccactccag ccggctgccc gcccgctgcc tcctctgtgc gtccgcccag 960
ccagcctcgt ccacgccgcc acc 983

<210> SEQ ID NO 17
<211> LENGTH: 1000
<212> TYPE: DNA
<213> ORGANISM: Artificial
<220> FEATURE:
<223> OTHER INFORMATION: Fragment of DES regulatory element

<400> SEQUENCE: 17
ccaaaagggt caggtccaag agggacctgg agtgccaagt ggaggtgtag aggcacggcc 60
agtacccatg gagaatggtg gatgtcctta ggggttagca agtgccgtgt gctaaggagg 120
gggctttgga ggttgggcag gccctctgtg gggctccatt tttgtggggg tgggggctgg 180
agcattatag gggtgggaa gtgattgggg ctgtcaccct agccttcctt atctgacgcc 240
cacccatgcc tcctcaggta ccccctgccc cccacagctc ctctcctgtg ccttgtttcc 300
cagccatgcg ttctcctcta taaataccg ctctggtatt tggggttggc agctgttgct 360
gccagggaga tggttgggtt gacatgcggc tcctgacaaa acacaaaccc ctggtgtgtg 420
tgggcgtggg tggtgtgagt agggggatga atcagggagg gggcgggga cccagggggc 480 aggagccaca caaagtctgt gcgggggtgg gagcgcacat agcaattgga aactgaaagc 540
ttatcagacc ctttctggaa atcagcccac tgtttataaa cttgaggccc caccctcgac 600
agtaccgggg aggaagaggg cctgcactag tccagaggga aactgaggct cagggctagc 660
tcgcccatag acatacatgg caggcaggct ttggccagga tccctccgcc tgccaggcgt 720
ctccctgccc tcccttcctg cctagagacc cccaccctca agcctggctg gtctttgcct 780
gagacccaaa cctcttcgac ttcaagagaa tatttaggaa caaggtggtt tagggccttt 840
cctgggaaca ggccttgacc ctttaagaaa tgacccaaag tctctccttg accaaaaagg 900
ggaccctcaa actaaaggga agcctctctt ctgctgtctc ccctgacccc actccccccc 960
accccaggac gaggagataa ccagggctga aagaggcccg 1000

<210> SEQ ID NO 18
<211> LENGTH: 1000
<212> TYPE: DNA
<213> ORGANISM: Artificial
<220> FEATURE:
<223> OTHER INFORMATION: Fragment of DES regulatory element

<400> SEQUENCE: 18
aatctggttc tttgggctgt aagtgatcaa agcaatacca agtgccttaa attaaaaaaa 60
aaaaaaaaaa aaaaaacgga aagtttgttg gcccaaggcc aggaaggaca gtgtgggagc 120
tcaactcaca aagttgaggg aagcactgca ggaaccaagg ggctggcctg ctcctcctct 180
ccagcctcct ctgcttctta catattgacc tctctttctt cctactcccc cagggggcag 240
gaaacatggc ttccacaggt tccagttgaa gaatcccagt tccgtctata aattccaggg 300
aaggtctctg attggccctg ctcattccca ggcccattcc ttgacccagt cactgaagtc 360

-continued

```
agggagatgc agtaataaga ctggctggaa tcagggtctt taggggtgga gggatgggga    420

ggaggcacag catgtcatca aaataaggaa attgcaaaag aaagcttgca ggctactttg    480

aatgacaatg agaaagacgg tgctgcctga gtgtgttaag gatccacatg gtctccaaaa    540

tcctccagga gcatacagtc tagtctggga gatgagacac aaaaataacc agaacacaac    600

agcttgcact gactcgaggg ctggataaga atatctggaa ctcccccatc tatttcagaa    660

gcttgtctct tggatgaaaa ttagacactt aatgggaaag ggctttgaaa agagtgcagt    720

aacaaagccc cctttacaat ttacccggca cattcacacc catcctgagg ccaaagccac    780

aggctgtgag gtctcactgt ctcagcttcc tgagctataa aatgggaatg atgctagtgt    840

ctacctccta gggttggaga attgggggtc atgggtgtga agtgctcagc agcttggccc    900

acactaggtg gtcagtacat gtaaggtatt attgttgcta catacattag tagggcctgg    960

gcctctttaa acctttatag ggtagcatgg caaggctaac                        1000
```

<210> SEQ ID NO 19
<211> LENGTH: 1000
<212> TYPE: DNA
<213> ORGANISM: Artificial
<220> FEATURE:
<223> OTHER INFORMATION: Fragment of ACTN2 regulatory element

<400> SEQUENCE: 19

```
cagatggatc acctgaagtc aggagtttaa gaccagtctg gccaacatgg caaaaccccg      60

tctctactaa aaatacaaaa atcagctagg tgtggtggca ggcacctgta ttcctagcta    120

ctagggtggt tgaggcggga gaatcacttg aactcgggag gcggagattg cggtgagctg    180

agatcatgcc actgcactcc agcctggaag caagactccg tctcaaaaaa taaaaataaa    240

aaataaaaat aaataaagtg gatggcttag agtatctttt ctgtttagac ctgactaaag    300

cttagacata attgttagtt taggctctca gggtaaaatt tattactgta aatccaaaaa    360

atcccttctt cttctttttt tttttttttt tggtccttga attaaatgct gtcacctcct    420

tcttgaaagg agaaactatt agtcagattt gaaaatcctc tttatcaccc aggaaaatca    480

tttttatgga cactttgtct ttctgtagtc tgacttagaa gcagcctgtt tttgataggt    540

tgaagttttc atcttgaaca caaaccctgt ttgtgtgtcc cctactcccc agtttgatgt    600

gccaggcact ttgttctcaa gcccagcagc tgttgtggga tgaggggaca ttttgcatgc    660

ttagccagca gctgccagaa acatttctaa tctggttttg gcaggaaata gggcacaagt    720

ggaagccaag ttaaaagaag ctggaaaaat aaacagaata actttagatg tcacttaata    780

tatggtccat tttcagccga agatttgccc tagtaatttg ttaatatgac tggactgtga    840

tcccttccaa aggcagggtt gaatatagtc acctttgaga tccaggatgt agtccagtgc    900

ttggaatatg cttgtaggag gttattgtta ttattttttc aatgatagac tatactgcaa    960

atttgtttaa ttgatttaat tagtagctta aaactgttgt                        1000
```

<210> SEQ ID NO 20
<211> LENGTH: 999
<212> TYPE: DNA
<213> ORGANISM: Artificial
<220> FEATURE:
<223> OTHER INFORMATION: Fragment of ACTN2 regulatory element

<400> SEQUENCE: 20

```
agctgaagcc gtgggacgtc tgagcggcac atttttatgg tcatcacaga tggtgctggg      60

tttttccttt tttttttttt ttttttttttg gtgagaagtc aattggccaa acttgaaatt    120
```

taccaataaa accctttaag tgttacaaaa tcactgggca aaggaataca tttgagatgt 180
ggtagcatct gtgaattcca tttacctaag agtatgaatt acaaaccaga tgaatgacag 240
attagttgtc atcaactaca cacagtttat tttttcatgt gagttgcact gtagactatt 300
tatgtttgca tatttttcag gattgtgtac agtaaacctt aagtgaatac aaaggatcca 360
attgtcctgt aagactcact tcaattacag attgtgctca gtattaaact ttgctagtac 420
tttcaggatg cagtcaatca agaggcaggg aaaggtctgt cagcatccac agcctccttt 480
tcaaattgga cacttagtct ctggtccgaa taataggtgc cccagtgtc acctcacaca 540 atggggtata cacagttttt aaaaatttat tttcagctgg gcacagtagc tcacacctaa 600
aatcccagca ctttgggagg ctgaggcagg tggatcacct gaggtcagga gttcaagacc 660
agcctggcca acgtggcaaa atcctgtctc tactaaaaat acaaaaatta accgggcatg 720
gtggtggcac ctgtagtccc agctactcgg gaggctgagg caggagaatc ttttgaaccc 780
gggaggcaga ggttgcagtg agccaagatc ccaccactgc actccagcct gggtgacaga 840
gtgagactgt gcctcaaaaa aaattaaaaa aagtattttc atttaaaaag gggcgagtca 900
ccaaccaccc tgaagtctag ttttagtgtc tttttatgtt ggagcttgtg gctgctcctg 960
cattgtcctt ttgaagtccc taagtgtcat cagaattta 999

<210> SEQ ID NO 21
<211> LENGTH: 999
<212> TYPE: DNA
<213> ORGANISM: Artificial
<220> FEATURE:
<223> OTHER INFORMATION: Fragment of FLNC regulatory element

<400> SEQUENCE: 21
cacactgacc tcccctggag cgagctcttg agtcagaggg aaagcaaggg aagctacgct 60
gggagttcct tctcccctcc ctggcttcct ccggcctctc cacctgaaca gaggcgctca 120
gctggctggg ggacctcaga taatgcctgc aaaacaggac tgtggaccat tagggtctgt 180
aaaggggctg tcagctccga gctacctcac cttaaccctt tctcctcccc agcagctcaa 240
agaggaatgc atcctttctc agatctgtgt ctcagtttac tcaccaggga ttcagaggca 300
gcactgctga accctgagcc cttggcacat caggttggct gtcagaagtc ggcctttgta 360
catacacagt tcccttgtga ggcccagctg cgtgtcctag gagcggggcc tctctccaca 420
gcagagctca gcctctcaag tgtatggaca gcacgggtgc ctgatgggtg gatttagcca 480
tgagttgaag gtggcttggg gagaatgaga gttctagaga tagggagaag ggttgccaa 540 taggagagtg gaattcctga gcacctcgtc acaggcagcc gacagaacat gagccgcagg 600
gcccaggcta tttatacctc gcctgtcact atcagggtcc ccacagctcc ccccacctcc 660
agccacacac agcaggtcct tttgctcttt ctggtccctt ctctactcct ccccctccct 720
acctaaggac caggcaattt cattcataga cccctgtcat cataagcatt gcccccacag 780
aaccctgaca ctttttcctc agctccgtaa caggggggtgc cctcattggc ccttggggga 840
aagagccccc aaagatgctc actatccctt cttttacacc aggtctaggg gtagaagagg 900
aattagatat aatgattcat ctaaaagggc ccagaacctt ccctggctta aagaaacttc 960
tcaggctcag atatggcctc ctagccagct cagctagac 999

<210> SEQ ID NO 22
<211> LENGTH: 1000
<212> TYPE: DNA

<213> ORGANISM: Artificial
<220> FEATURE:
<223> OTHER INFORMATION: Fragment of FLNC regulatory element

<400> SEQUENCE: 22

```
aaaaaaaaaa gaaaaaagaa aaagaaatac gttctctagc tctttctcct caccccaggc     60
cagagtctgt ttgggtgcct cggtttccct gctgttctat tccccaggcc tgcagccttt    120
ggcttgccct gagtgcagct ttgcctgggc atcccagctg gctcccttag gctctccctg    180
accactctgc ccctggtcct gcctacccac ctggtcacat ttccccctgg ctgctctggc    240
tggggctctc cctgtttctg cctggctgac ccaccctttc cctggcagga tctgccctgt    300
ggcccaaatg ggcatgttgc ccagggggct ccctggcact atgggggaag agtctctcct    360
tcccctctta tcatctcagt tgagtcagac ttgggggagg gggatacaca gtgtgagtca    420
ctgggtaccc ttttcctgag ctcagcttca taccgaggcg atgaggccaa acgggctggt    480
gacagggaca ctgagtcagg ggcaggggcc ccggtcttac tcctgggcct ctggatttgg    540
gccctacatg aggcttttct atctgtaaag tcaagcaatg gctgggaggc acacacaacc    600
ccccgccccc ccgcaggctt ctccttcatt ggcccgggca aggtccctgc ttcctctcag    660
gccgtctctg cacaagcaca cacacttccc ttccctgtcc acaggtggac aatgccctgg    720
gctaggagcc agccctcgca ggccctgtca acagcctgcc accaactagt ctagaaaatt    780
ctgtgaacac cagatcagtg ggttttgccc taatcactgg cctcagtttc cccatttacc    840
tcttcagccc gtgcggggtg tggagggagc atatttcatt cctgacagtt tggtgtgttg    900
ggtgtggatg gagaactgtc ggccctcccc gccaccttcc agcgcggcgg caccgggggc    960
ccagggggtg ggcgccctca accccgtccc gccgcccggg                         1000
```

<210> SEQ ID NO 23
<211> LENGTH: 1000
<212> TYPE: DNA
<213> ORGANISM: Artificial
<220> FEATURE:
<223> OTHER INFORMATION: Fragment of ATP2A1 regulatory element

<400> SEQUENCE: 23

```
ccctgtgggc atttgagttt ataacaccac ccccattgtg gcacacccct ccaccccgta     60
aaacacaggc tctgctcttg gaatcagtct tcctgatctg tggctgtgcc ctccaacaga    120
gggcacccct gggcttccca gctctggggg tagtgggtgc caacaaggag gggcctgggg    180
ctgaagaatc ccacccgctg agctcggcct tctcccttcc ccactgtcca gctccgcctt    240
tcagcatcct gcctcactcc ccgcccaggc agcaaggagc ccacaccctc atgcccctca    300
gcttcagccc ccacctccag gaggccctac ccacgctcat gaccttgcta ttctgggcct    360
tgtgtcctgt agggagatgg acaggagaca gctgggcttc caggccaccc aggcgggggg    420
ctagccgagg gaagcctgct ggctctcctg cttgctctaa tttctggggc tccccaaacc    480
ttggcctcag gagactgggg ataggaccgg ccttgaaagt gggggaagct ttggagagcc    540
gggtgctggg ttcttagtga gatggccagt gaaggctgtg gtgccccgag gtaagcaggg    600
cctgatcccc tcctaatctt ccagcagcaa ctggtgctct gaggctcccc ctcccccagc    660
cctgccagcc ttcagggacc tgccttccaa agatgggcag gggaggggga cgaggacacc    720
cacccactcc tcagaccagc atgtcttggc tgttggggcc tgagagactt tccctctaag    780
cctttcttta cagatggtta aaccgaagtt ctgcactcat cagggactgg ccagggtgtc    840
tctgtgtccc atgcttttag ctccagccct caggtgtgac aggaggatca ctttccatcc    900
```

ctgggcgtgg agacccctgt gggaagggat ccccgagggc gcctctggct cagcctccct 960
ccatggcagt tcacacccac agccttccct agagcagccc 1000

<210> SEQ ID NO 24
<211> LENGTH: 999
<212> TYPE: DNA
<213> ORGANISM: Artificial
<220> FEATURE:
<223> OTHER INFORMATION: Fragment of TNNI1 regulatory element

<400> SEQUENCE: 24
gggccacagt gaaggcccag aggggcaagt agcagctggg ggaagaggac cattgggcta 60
accctgcatc tcttataagg caatatggaa atgaggcccc tgaacccatg ccccaaaagc 120
ccaagagggc taaagactca gctttcaggg atttttcagt ggctctggtg cacgtgggat 180
acgagggtgc ctggctgtgg ggagtgatgt gagcagtgtt gcaggctgac cccagtgagt 240
gtttccaggg ctgagcagaa tggcagtggc agcagggcac acctttatgc tcagggaggt 300
ctgagggtct gcagacactc tgcatccccc tccagatggg tttcctggaa tctagatttc 360
ccaggttcca aaggacaccc gagtctcatg cctggaactc agtgagacta attcacctct 420
cctctgccct aatcttcatc tccagccaga agccaacaga tcccagggga ctggagccac 480
aggggctgca cctgtttacc gggtattttt aggatggttg atgaacacat aatacccacc 540
ctatagtcag agaaagacaa tgcctgctat gttaatcctg tggctattat agtctgtcat 600
ctcatgggtt ggggcaggac actgaccctc tcagaggcca gagagaggcc tcgcaagcag 660
gaggttaggg agccccagcc atgctcccca tttggagaag gagagagtaa tgggcagggg 720
tgtcctaagg agacacaccc cagtgcccac agaggtaaag gccctgccct ctctacaacg 780
acattctgct gcctaataga ggttgctcta attctgttct ggtcgggtca actttgagaa 840
gcctctatgt gagacggctg ccagggagaa atgacagggt ctggggaggc ataggggttg 900
gggacatagg attccaagtg gagaggctgt gatggataat gaaggcaggc tccagccaaa 960
aggagcagct agaggggaga aggaatttag gggctttgc 999

<210> SEQ ID NO 25
<211> LENGTH: 999
<212> TYPE: DNA
<213> ORGANISM: Artificial
<220> FEATURE:
<223> OTHER INFORMATION: Fragment of TNNI1 regulatory element

<400> SEQUENCE: 25
ttgtggggtc tgggaagtgg ggaattaaaa gacacttgta aagtgcctgc caataattgt 60
atcccagagc caccccttcc tctgccctaa ttctctcctt tccctttgtg cccatgaagc 120
actatcccaa ccccaatgaa cacagctttg gccacctccc ctgaatctcc caacgggtca 180
gaaagccttc tgggcctccc tccacctctg cctccgccac caggggaggg taaggctggg 240
gtggaggagg tggaggtgta gtgtgacccc agagtctcag ctgtcatgct ggggcacaga 300
gggaggggta tggagacaat ccatgaattc ctgagatgct tggctggtat tagattttat 360
gggcagctgc ttattcttag ggctctgctt ctccaaagac actgaggaag tccaaaggaa 420
acaccagctg gcgaagagcc acctccaggc ccatctgtcc atcatcagcc tccaggaatg 480
ccagtgtcca gagggcacca ggtctgcgtc tgtctccctg ggatgtgcct tgtccttggt 540
gggcatttgg cagtgatcat gcctccctgt ctccctcaga gatccaactg tccccattgt 600

```
ggggccctac cttccaaggc cggtttacac ctcctgccaa gctccggggc ctgcccccag    660

cctgcctcac tgacaaatgc cagaccaagg ggtcccacgt caggcaagag gcctcagcct    720

gtgctctgac accccctcaga cgggggccct tgccaggctc tgtggaagac aagcgaggac    780

tgataagtca ggatgaagat agcagccact ggaaggcttg gagagccagg attccatctc    840

ctctacaagt agcaagcaag gagataatga gaaaatcctc cccccgaggg ggggagcaaa    900

gagtctctgg tggttgcctc agagctgggc tttcccttcc ttgaggcttt gcagcgtgga    960

agggactatc cgctagacta tgagattgag tctgtgtgt                            999
```

<210> SEQ ID NO 26
<211> LENGTH: 1000
<212> TYPE: DNA
<213> ORGANISM: Artificial
<220> FEATURE:
<223> OTHER INFORMATION: Fragment of MYLPF1 regulatory element

<400> SEQUENCE: 26

```
tcttttgggg atccaaggcc ccagtcccgt caacccctct cccctcactg ccacatccct     60

ctgtgctcct catgttccac tgagaatccc gacctcaatc tcatgagcgc tccaggttgt    120

ccttagatca caagcataaa gacctgacgt tatgagctcc aaccttccaa cttctaaacg    180

ccctcttctt tctctgaccc ccatattctg atttccatat agcatccacc atcctggaat    240

tccagtgaga cctagctccc gacttctcag ctcctccttg gtttctgagt cctctaaggt    300

ccctcactcc caactcagcc ccatgtcctg tcaattccca ctcagtgtct gatctccttc    360

tcctcacctt tcccatctcc cgtttgaccc aagcttcctg agctctcctc ccattcccct    420

ttttggagtc ctcctcctct cccagaaccc agtaataagt gggctcctcc ctggcctgga    480

cccccgtggt aaccctataa ggcgaggcag ctgctgtctg aggcagggag gggctggtgt    540

gggaggctaa gggcagctgc taagtttagg gtggctcctt ctctcttctt agagacaaca    600

ggtggctggg gcctcagtgc ccagaaaaga aaatgtctta gaggtatcgg catgggcctg    660

gaggaggggg gacagggcag ggggaggcat cttcctcagg acatcgggtc ctagagggag    720

cgggaggaga aggagatggt tgtccttgcc aacttggggc ttcctcagcc actatttttc    780

cagacttctg ctgcatggag gggactgggt cactgaggcc cagagggaga agagagggta    840

catcaaagtc acacaatcag ccaagctggc tcttggccag aataaagtga gctgccactg    900

gctatcaagg cacctcacag aaagtgacca gctggctgtc cttttagggt cttttcctcc    960

cctcttgagt tccagcctcc acaccagtac ccagagaaaa                          1000
```

<210> SEQ ID NO 27
<211> LENGTH: 999
<212> TYPE: DNA
<213> ORGANISM: Artificial
<220> FEATURE:
<223> OTHER INFORMATION: Fragment of MYH1 regulatory element

<400> SEQUENCE: 27

```
gggatcatta gctaaatctc actggcctct tgagatttca actgaatgtt cctgtgaagt     60

accacatatt atgtctctac aaacactatt gcagttcctc ctgcctcctg ggaaaaaagt    120

gaaatatgct tggctcaaga tattcacttc tcatacagaa gatccttgac atttggaata    180

taattgagtc ctgagactcc ctctgcaggg tcctgtcgcc atataataga gggactacta    240

aaagcaacag tattaaagct cagactagga ataaatcaca tatcctcaat ccctggacaa    300

cttgtttact tctagtgtta gttttttctt aaaaaaaaaa ttgaaatcat tctgaggctg    360
```

gaatactttg gacatgccca gcagttcctg gcagttccca cagaagcatt acctcatgac 420
tggagtgggt aaagcatact gtgggctatg gataagactg acattaacca caagcatgtt 480
tggcagcaga ctggtgcttt acaagctcca tgttcagcag gagctgcaaa gtgttcctcc 540
aaaccaatat ttgtcattct tggattctat ttaggaggtc ctgttactca catgtttcaa 600
tatcagcaga agccagtttc cctgtggtac cgaagtggat cctgatgaat ttacccttgt 660
aagtaaaaaa aatgatgtta tacccaaagc ttgaagtacg tagtggggat gccactgaaa 720
taattcagac atgctttctc tggcatctaa aggcagagaa gaccctttgg caaccaagag 780
acttacaaag cgagaggagt tgtcattcct cacggtcttg gcgttgccaa aggcctccag 840
tagggggttg gcactgatga tttgatcttc cagagtcccc tgcaaaggca agagcagtcc 900
ttgcatctgg ggcttgggaa tttcctacct gagagtcccg acagagcctg gattctgact 960
aacaatcaga ctcacctgca ttttgccaga agtaacttc 999

<210> SEQ ID NO 28
<211> LENGTH: 1000
<212> TYPE: DNA
<213> ORGANISM: Artificial
<220> FEATURE:
<223> OTHER INFORMATION: Fragment of TPM3 regulatory element

<400> SEQUENCE: 28
gtgcctacct gtttacttct ttcttctgcc tgcttctgct cagcttcagc ttgctctgcc 60
cgatccagag cattctcctt gtctaacttc agcatctgca tctttttctt gatggcctcc 120
atcatgagca gtggctgttg gtaggctcac ctgtgaacac tggagaactg gagactgggg 180
caagaaagaa ggggctgctg cctgagtgac caggaggtcc ccagacttga gtctttatct 240
gtgctcatag ctccaccttt tgttcctaat atggtctttc cagctccctc caccccatca 300
ttgttctcct gggggaacac agggtgagac gctttgatga actgacatca ccagcaaaaa 360
aaatatctag caacagctga ggctgatttt agacaatgga aagtggggga gggaagaggt 420
tctccctgac cctgaaactt tccactcatt ctgggcagct ctatggatgt tttaaaagaa 480
gaggaagagg ggagggaaga acattgaaat agagaagtgt actttggcaa ttctaggttg 540
gcagtttgca tccaggggggt cctggttgcc tttcagcttc ccgtttcact ctcccccaga 600
ctgtgttgaa tgctggtcaa actccgttag ttgagtttta gcttttgatt cctggtattc 660
aaggagcttg ggcacaggga agaggggagg tcactcatga tccttaacaa ttctcccaga 720
tccccagatc aaattgctgt gctattctgg gagtctccga ttggcaggga gacgtttttc 780
ctccccacca agagccacaa gagtagagta agaggtaggg ttggaatctc caaccctatc 840
cttgaaggct atcccagagc ttcaagtggg gtggggagag aaacagggga gggtcagaac 900
aatccagaca ggatcatacc ctttgttttc ccacagtaat cttaaaatag aactgttgta 960
cccacacaga ctttggtctg tgtggctctc tcctcttctt 1000

<210> SEQ ID NO 29
<211> LENGTH: 999
<212> TYPE: DNA
<213> ORGANISM: Artificial
<220> FEATURE:
<223> OTHER INFORMATION: Fragment of ANKRD2 regulatory element

<400> SEQUENCE: 29
ggcatgcaat ctccagcaga gtgagcctgg aactgccagt cttctgggcc ctgatcccag 60

-continued

```
ctcccctggt gtcctcatga gtcctcagga aaagccactc tttgcttttc tttaaagcag    120

agccatgctg cctgccctgc ctcctccatc agttgctggg aggattaagc aggaagacag    180

atgtgaaagt gcttgcaagg cgaagacagc acctcaggaa ggtggtctgc tcctgcagca    240

agaggggcta acttccggcc ctggagacgc tgtagccatc gtgatgttaa agcaaaatct    300

ctgacagatt tagatcgtgt gtcagaggtt tgtgtcagct tcccagcaag ggaaccagaa    360

aggaaaagga accggttcct catgcttcct aggggaatgc atgcatatct gaagagaagg    420

gaatcttata taaggctgtt tagctaaggg cagccaccag ccaggtgagc cttacagaag    480

cacagggctg ggtgtctgca gttccctagc agattaacct gggtcacagt gactcagagc    540

tccagcatgc gagttccagg tgtggaactg agcaagtaca gatctgcttt tgctccactt    600

gggagtattt ttccttctta gtgagcatgg gcagcctcct ggccagggaa gtctggcact    660

gtctgggcct gacagggaaa ccctgggagg gtagaaggat ccagagtagc tgctgttcct    720

cgctagctgg gcttagtgct ttccggagac ccctttcttg aagcaagact ctgtaagccc    780

tgcagaggtc ccctgagcac ttaccaagag aggagacaga ttggataagg tttgttcatg    840

actaaaagtc acccagccaa atgcagtgat gcttaacggg gaagcatgtg ggaccccgga    900

gagccgaagg ccagcgtgag ctgtgatcag agagggagac agctgccctt cctgctacca    960

cggccctggc ctggacaagt agagtgtgac cctcctcac                           999
```

<210> SEQ ID NO 30
<211> LENGTH: 663
<212> TYPE: DNA
<213> ORGANISM: Artificial
<220> FEATURE:
<223> OTHER INFORMATION: CMV promoter

<400> SEQUENCE: 30

```
acgcgtggag ctagttatta atagtaatca attacggggt cattagttca tagcccatat     60

atggagttcc gcgttacata acttacggta aatggcccgc ctggctgacc gcccaacgac    120

ccccgcccat tgacgtcaat aatgacgtat gttcccatag taacgtcaat agggactttc    180

cattgacgtc aatgggtgga gtatttacgg taaactgccc acttggcagt acatcaagtg    240

tatcatatgc caagtacgcc ccctattgac gtcaatgacg gtaaatggcc cgcctggcat    300

tatgcccagt acatgacctt atgggacttt cctacttggc agtacatcta cgtattagtc    360

atcgctatta ccatggtgat gcggttttgg cagtacatca atgggcgtgg atagcggttt    420

gactcacggg gatttccaag tctccacccc attgacgtca atgggagttt gttttgcacc    480

aaaatcaacg ggactttcca aaatgtcgta acaactccgc cccattgacg caaatgggcg    540

gtaggcgtgt acggtgggag gtctatataa gcagagctcg tttagtgaac cgtcagatcg    600

cctggagacg ccatccacgc tgttttgacc tccatagaag acaccgggac cgatccagcc    660

tcc                                                                  663
```

<210> SEQ ID NO 31
<211> LENGTH: 20
<212> TYPE: DNA
<213> ORGANISM: Artificial
<220> FEATURE:
<223> OTHER INFORMATION: Primer

<400> SEQUENCE: 31

```
tgtgtccgtc gtggatctga                                                 20
```

<210> SEQ ID NO 32
<211> LENGTH: 22
<212> TYPE: DNA
<213> ORGANISM: Artificial
<220> FEATURE:
<223> OTHER INFORMATION: primer

<400> SEQUENCE: 32
gcctgcttca ccaccttctt ga 22

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
gtccctcact cccaactcag 20

<210> SEQ ID NO 34
<211> LENGTH: 23
<212> TYPE: DNA
<213> ORGANISM: Artificial Sequence
<220> FEATURE:
<223> OTHER INFORMATION: primer

<400> SEQUENCE: 34
gaggagaagg agatcagaca ctg 23

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
tagctgggcc tttccttctc 20

<210> SEQ ID NO 36
<211> LENGTH: 20
<212> TYPE: DNA
<213> ORGANISM: Artificial Sequence
<220> FEATURE:
<223> OTHER INFORMATION: primer

<400> SEQUENCE: 36
cgtctcccta gcagcaacag 20

<210> SEQ ID NO 37
<211> LENGTH: 171
<212> TYPE: DNA
<213> ORGANISM: Artificial Sequence
<220> FEATURE:
<223> OTHER INFORMATION: Fragment a of skeletal muscle-specific regulatory element 4 (Sk-SH4a)

<400> SEQUENCE: 37
ctctaaggtc cctcactccc aactcagccc catgtcctgt caattcccac tcagtgtctg 60
atctccttct cctcaccttt cccatctccc gtttgaccca agcttcctga gctctcctcc 120
cattcccctt tttggagtcc tcctcctctc ccagaaccca gtaataagtg g 171

<210> SEQ ID NO 38
<211> LENGTH: 51

```
<212> TYPE: DNA
<213> ORGANISM: Artificial Sequence
<220> FEATURE:
<223> OTHER INFORMATION: Fragment b of skeletal muscle-specific
      regulatory element 4 (Sk-SH4b)

<400> SEQUENCE: 38

tggcctggac ccccgtggta accctataag gcgaggcagc tgctgtctga g              51


<210> SEQ ID NO 39
<211> LENGTH: 60
<212> TYPE: DNA
<213> ORGANISM: Artificial Sequence
<220> FEATURE:
<223> OTHER INFORMATION: Fragment c of skeletal muscle-specific
      regulatory element 4 (Sk-SH4c)

<400> SEQUENCE: 39

gcagggaggg gctggtgtgg gaggctaagg gcagctgcta agtttagggt ggctccttct     60


<210> SEQ ID NO 40
<211> LENGTH: 41
<212> TYPE: DNA
<213> ORGANISM: Artificial Sequence
<220> FEATURE:
<223> OTHER INFORMATION: Fragment d of skeletal muscle-specific
      regulatory element 4 (Sk-SH4d)

<400> SEQUENCE: 40

aggaggggg acagggcagg gggaggcatc ttcctcagga c                          41


<210> SEQ ID NO 41
<211> LENGTH: 120
<212> TYPE: DNA
<213> ORGANISM: Artificial Sequence
<220> FEATURE:
<223> OTHER INFORMATION: Fragment e of skeletal muscle-specific
      regulatory element 4 (Sk-SH4e)

<400> SEQUENCE: 41

gcagggaggg gctggtgtgg gaggctaagg gcagctgcta agtttagggt ggctccttct     60

ctcttcttag agacaacagg tggctggggc ctcagtgccc agaaaagaaa atgtcttaga    120


<210> SEQ ID NO 42
<211> LENGTH: 17
<212> TYPE: DNA
<213> ORGANISM: Artificial Sequence
<220> FEATURE:
<223> OTHER INFORMATION: primer

<400> SEQUENCE: 42

gtgccctact acatcaa                                                    17


<210> SEQ ID NO 43
<211> LENGTH: 16
<212> TYPE: DNA
<213> ORGANISM: Artificial Sequence
<220> FEATURE:
<223> OTHER INFORMATION: primer

<400> SEQUENCE: 43

aggttgtgct ggtcca                                                     16


<210> SEQ ID NO 44
<211> LENGTH: 8069
<212> TYPE: DNA
```

<213> ORGANISM: Artificial Sequence
<220> FEATURE:
<223> OTHER INFORMATION: AAVss-SkSH4-Des-MVM-MD1 plasmid construct

<400> SEQUENCE: 44
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tcgtacgttc tgagtcctct aaggtccctc actcccaact 180
cagccccatg tcctgtcaat tcccactcag tgtctgatct ccttctcctc acctttccca 240
tctcccgttt gacccaagct tcctgagctc tcctcccatt cccctttttg gagtcctcct 300
cctctcccag aacccagtaa taagtgggct cctccctggc ctggaccccc gtggtaaccc 360
tataaggcga ggcagctgct gtctgaggca gggaggggct ggtgtgggag gctaagggca 420
gctgctaagt ttagggtggc tccttctctc ttcttagaga caacaggtgg ctggggcctc 480
agtgcccaga aaagaaaatg tcttagaggt atcggcatgg gcctggagga gggggggacag 540 ggcaggggga ggcatcttcc tcaggacatc gggtcctaga gggaccttgc ttcctagctg 600
ggcctttcct tctcctctat aaataccagc tctggtattt cgccttggca gctgttgctg 660
ctagggagac ggctggcttg acatgcatct cctgacaaaa cacaaacccg tggtgtgagt 720
gggtgtgggc ggtgtgagta gggggatgaa tcagagaggg ggcgagggag acaggggcgc 780
aggagtcagg caaaggcgat gcgggggtgc gactacacgc agttggaaac agtcgtcaga 840
agattctgga aactatcttg ctggctataa acttgaggga agcagaaggc caacattcct 900
cccaagggaa actgaggctc agagttaaaa cccaggtatc agtgatatgc atgtgccccg 960
gccagggtca ctctctgact aaccggtacc taccctacag gcctacctag agactctttt 1020
gaaaggatgg tagagacctg tccgggcttt gcccacagtc gttggaaacc tcagcatttt 1080
ctaggcaact tgtgcgaata aaacacttcg gggtccttc ttgttcattc caataaccta 1140
aaacctctcc tcggagaaaa tagggggcct caaacaaacg aaattctcta gcccgctttc 1200
cccaggataa ggcaggcatc caaatggaaa aaaaggggcc ggccgggggt ctcctgtcag 1260
ctccttgccc tgtgaaaccc agcaggcctg cctgtcttct gtcctcttgg ggctgtccag 1320
gggcgcaggc ctcttgcggg ggagctggcc tccccgcccc ctcgcctgtg gccgcccttt 1380
tcctggcagg acagagggat cctgcagctg tcaggggagg ggcgccgggg ggtgatgtca 1440
ggagggctac aaatagtgca gacagctaag gggctccgtc acccatcttc acatccactc 1500
cagccggctg cccgcccgct gcctcctctg tgcgtccgcc cagccagcct cgtccacgcc 1560
gccacctcta gaaagaggta agggtttaag ggatggttgg ttggtggggt attaatgttt 1620
aattacctgg agcacctgcc tgaaatcact ttttttcagg ttggacgcgt gccaccatgc 1680
tgtggtggga ggaagtggag gactgctacg agagagagga cgtgcagaag aaaaccttca 1740
ccaagtgggt gaacgcccag ttcagcaagt tcggcaagca gcacatcgag aacctgttca 1800
gcgacctgca ggatggcagg agactgctgg atctgctgga gggactgacc ggccagaagc 1860
tgcccaagga gaagggcagc accagagtgc acgccctgaa caacgtgaac aaggccctga 1920
gagtgctgca gaacaacaac gtggacctgg tgaatatcgg cagcaccgac atcgtggacg 1980
gcaaccacaa gctgaccctg ggcctgatct ggaacatcat cctgcactgg caggtgaaga 2040
acgtgatgaa gaacatcatg gccggcctgc agcagaccaa cagcgagaag atcctgctga 2100
gctgggtgag gcagagcacc agaaactacc cccaggtgaa cgtgatcaac ttcaccacct 2160
cctggagcga cggcctggcc ctgaacgccc tgatccacag ccacagaccc gacctgttcg 2220
actggaacag cgtggtgtgt cagcagagcg ccacccagag actggagcac gccttcaaca 2280
tcgccagata ccagctgggc atcgagaagc tgctggaccc cgaggacgtg gacaccacct 2340
accccgacaa gaaaagcatc ctgatgtata ttacctctct gtttcaggtg ctgccccagc 2400
aggtgtccat cgaggccatc caggaagtgg aaatgctgcc caggcccccc accgtgtccc 2460
tggcccaggg ctatgagaga accagcagcc ccaagcccag attcaagagc accgtgtccc 2520
tggcccaggg ctatgagaga accagcagcc ccaagcccag attcaagagc tacgcctaca 2580
cccaggccgc ctacgtgacc acctccgacc ccaccagaag ccccttcccc agccagcacc 2640
tggaggcccc cgaggacaag agcttcggca gcagcctgat ggagagcgaa gtgaacctgg 2700
acagatacca gaccgccctg gaggaagtgc tgtcttggct gctgtccgcc gaggacaccc 2760
tgcaggccca gggcgagatc agcaacgacg tggaagtggt gaaggaccag ttccacaccc 2820
acgagggcta catgatggat ctgaccgccc accagggcag agtgggcaat atcctgcagc 2880
tgggcagcaa gctgatcggc accggcaagc tgagcgagga cgaggagacc gaagtgcagg 2940
agcagatgaa cctgctgaac agcagatggg agtgcctgag agtggccagc atggagaagc 3000
agagcaacct gcaccgcgtg ctgatggacc tgcagaacca gaagctgaag gagctgaacg 3060
actggctgac caagaccgag gagcggacca gaaagatgga ggaggagccc ctgggccccg 3120
acctggagga cctgaagaga caggtgcagc agcacaaagt gctgcaggag gacctggaac 3180
aggagcaggt gcgcgtgaac agcctgaccc acatggtggt cgtggtggac gagagcagcg 3240
gcgaccacgc cacagccgcc ctggaagagc agctgaaagt gctgggcgac agatgggcca 3300
acatctgccg gtggaccgag gacagatggg tgctgctgca ggacatcctg ctgaagtggc 3360
agagactgac agaggagcag tgcctgttta gcgcctggct gagcgagaag gaggacgccg 3420
tgaacaagat ccacaccacc ggcttcaagg accagaacga gatgctgagc agcctgcaga 3480
agctggccgt gctgaaggcc gatctggaga agaaaaagca gagcatgggc aagctgtact 3540
ccctgaagca ggacctgctg tccaccctga agaacaagag cgtgacccag aaaaccgagg 3600
cctggctgga caatttcgcc cggtgctggg acaatctggt gcagaaactg gagaagagca 3660
ccgcccagat cagccaggcc gtgaccacca cccagcccag cctgacacag accaccgtga 3720
tggagaccgt gaccacagtg accaccaggg agcagatcct ggtgaagcac gcccaggagg 3780
agctgccccc tcccccccct cagaagaagc ggcagatcac agtggacacc ctggagagac 3840
tgcaggagct gcaggaagcc accgacgagc tggacctgaa gctgagacag gccgaagtga 3900
tcaagggcag ctggcagcct gtgggcgatc tgctgatcga cagcctgcag gaccacctgg 3960
agaaagtgaa ggccctgcgg ggcgagatcg ccccctgaa ggagaatgtg agccacgtga 4020
acgacctggc cagacagctg accaccctgg gcatccagct gagcccctac aatctgagca 4080
ccctggaaga tctgaacacc cggtggaaac tgctgcaggt ggccgtggag gatagagtga 4140
ggcagctgca cgaggcccac agagacttcg gccctgcctc ccagcacttc ctgagcacca 4200
gcgtgcaggg cccctgggag agagccatct cccccaacaa agtgccctac tacatcaacc 4260
acgagaccca gaccacctgc tgggaccacc ctaagatgac cgagctgtac cagagcctgg 4320
ccgacctgaa caatgtgcgg ttcagcgcct acagaaccgc catgaagctg cggagactgc 4380
agaaggccct gtgcctggac ctgctgagcc tgagcgccgc ctgcgacgcc ctggaccagc 4440
acaacctgaa gcagaacgac cagcccatgg acattctgca gatcatcaac tgcctgacca 4500
ccatctacga tcggctggag caggagcaca acaacctggt gaacgtgccc ctgtgcgtgg 4560
acatgtgcct gaattggctg ctgaacgtgt acgacaccgg caggaccggc agaatcagag 4620
tgctgtcctt caagaccggc atcatcagcc tgtgcaaggc ccacctggag gataagtacc 4680
gctacctgtt caagcaggtg gccagcagca ccggcttctg cgatcagagg agactgggcc 4740
tgctgctgca cgatagcatc cagatcccta ggcagctggg cgaagtggcc agctttggcg 4800
gcagcaacat cgagccctct gtgaggagct gcttccagtt cgccaacaac aagcccgaga 4860
tcgaggccgc cctgttcctg gattggatga ggctggagcc ccagagcatg gtgtggctgc 4920
ctgtgctgca cagagtggcc gccgccgaga ccgccaagca ccaggccaag tgcaacatct 4980
gcaaggagtg ccccatcatc ggcttccggt acaggagcct gaagcacttc aactacgaca 5040
tctgccagag ctgctttttc agcggcagag tggccaaggg ccacaagatg cactacccca 5100
tggtggagta ctgcaccccc accacctccg gcgaggatgt gagagacttc gccaaagtgc 5160
tgaagaataa gttccggacc aagcggtact ttgccaagca ccccaggatg ggctacctgc 5220
ccgtgcagac cgtgctggag ggcgacaaca tggagaccga caccatgtga tgatgactcg 5280
agaataaaag atctttattt tcattagatc tgtgtgttgg tttttgtgt gaggaacccc 5340
tagtgatgga gttggccact ccctctctgc gcgctcgctc gctcactgag gccgggcgac 5400
caaaggtcgc ccgacgcccg ggctttgccc gggcggcctc agtgagcgag cgagcgcgca 5460
gctgcctgca ggggcgcctg atgcggtatt ttctccttac gcatctgtgc ggtatttcac 5520
accgcatacg tcaaagcaac catagtacgc gccctgtagc ggcgcattaa gcgcggcggg 5580
tgtggtggtt acgcgcagcg tgaccgctac acttgccagc gccctagcgc ccgctccttt 5640
cgctttcttc ccttcctttc tcgccacgtt cgccggcttt ccccgtcaag ctctaaatcg 5700
ggggctccct ttagggttcc gatttagtgc tttacggcac ctcgacccca aaaaacttga 5760
tttgggtgat ggttcacgta gtgggccatc gccctgatag acggtttttc gccctttgac 5820
gttggagtcc acgttcttta atagtggact cttgttccaa actggaacaa cactcaaccc 5880
tatctcgggc tattcttttg atttataagg gattttgccg atttcggcct attggttaaa 5940
aaatgagctg atttaacaaa aatttaacgc gaattttaac aaaatattaa cgtttacaat 6000
tttatggtgc actctcagta caatctgctc tgatgccgca tagttaagcc agccccgaca 6060
cccgccaaca cccgctgacg cgccctgacg ggcttgtctg ctcccggcat ccgcttacag 6120
acaagctgtg accgtctccg ggagctgcat gtgtcagagg ttttcaccgt catcaccgaa 6180
acgcgcgaga cgaaagggcc tcgtgatacg cctattttta taggttaatg tcatgataat 6240
aatggtttct tagacgtcag gtggcacttt tcggggaaat gtgcgcggaa cccctatttg 6300
tttatttttc taaatacatt caaatatgta tccgctcatg agacaataac cctgataaat 6360
gcttcaataa tattgaaaaa ggaagagtat gagtattcaa catttccgtg tcgcccttat 6420
tcccttttttt gcggcatttt gccttcctgt ttttgctcac ccagaaacgc tggtgaaagt 6480
aaaagatgct gaagatcagt tgggtgcacg agtgggttac atcgaactgg atctcaacag 6540
cggtaagatc cttgagagtt ttcgccccga agaacgtttt ccaatgatga gcacttttaa 6600
agttctgcta tgtggcgcgg tattatcccg tattgacgcc gggcaagagc aactcggtcg 6660
ccgcatacac tattctcaga atgacttggt tgagtactca ccagtcacag aaaagcatct 6720
tacggatggc atgacagtaa gagaattatg cagtgctgcc ataaccatga gtgataacac 6780
tgcggccaac ttacttctga caacgatcgg aggaccgaag gagctaaccg cttttttgca 6840
caacatgggg gatcatgtaa ctcgccttga tcgttgggaa ccggagctga atgaagccat 6900
accaaacgac gagcgtgaca ccacgatgcc tgtagcaatg gcaacaacgt tgcgcaaact 6960

```
attaactggc gaactactta ctctagcttc ccggcaacaa ttaatagact ggatggaggc   7020

ggataaagtt gcaggaccac ttctgcgctc ggcccttccg gctggctggt ttattgctga   7080

taaatctgga gccggtgagc gtgggtctcg cggtatcatt gcagcactgg ggccagatgg   7140

taagccctcc cgtatcgtag ttatctacac gacggggagt caggcaacta tggatgaacg   7200

aaatagacag atcgctgaga taggtgcctc actgattaag cattggtaac tgtcagacca   7260

agtttactca tatatacttt agattgattt aaaacttcat ttttaattta aaaggatcta   7320

ggtgaagatc ctttttgata atctcatgac caaaatccct taacgtgagt tttcgttcca   7380

ctgagcgtca gaccccgtag aaaagatcaa aggatcttct tgagatcctt tttttctgcg   7440

cgtaatctgc tgcttgcaaa caaaaaaacc accgctacca gcggtggttt gtttgccgga   7500

tcaagagcta ccaactcttt ttccgaaggt aactggcttc agcagagcgc agataccaaa   7560

tactgtcctt ctagtgtagc cgtagttagg ccaccacttc aagaactctg tagcaccgcc   7620

tacatacctc gctctgctaa tcctgttacc agtggctgct gccagtggcg ataagtcgtg   7680

tcttaccggg ttggactcaa gacgatagtt accggataag gcgcagcggt cgggctgaac   7740

ggggggttcg tgcacacagc ccagcttgga gcgaacgacc tacaccgaac tgagatacct   7800

acagcgtgag ctatgagaaa gcgccacgct tcccgaaggg agaaaggcgg acaggtatcc   7860

ggtaagcggc agggtcggaa caggagagcg cacgagggag cttccagggg gaaacgcctg   7920

gtatctttat agtcctgtcg ggtttcgcca cctctgactt gagcgtcgat ttttgtgatg   7980

ctcgtcaggg gggcggagcc tatggaaaaa cgccagcaac gcggcctttt tacggttcct   8040

ggccttttgc tggccttttg ctcacatgt                                     8069


<210> SEQ ID NO 45
<211> LENGTH: 7217
<212> TYPE: DNA
<213> ORGANISM: Artificial Sequence
<220> FEATURE:
<223> OTHER INFORMATION: AAVss-SkSH4-Des-MVM-FST-2A-Luc2 plasmid
      construct

<400> SEQUENCE: 45

cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc tcgtacgttc tgagtcctct aaggtccctc actcccaact    180

cagccccatg tcctgtcaat tcccactcag tgtctgatct ccttctcctc acctttccca    240

tctcccgttt gacccaagct tcctgagctc tcctcccatt cccctttttg gagtcctcct    300

cctctcccag aacccagtaa taagtgggct cctccctggc ctggaccccc gtggtaaccc    360

tataaggcga ggcagctgct gtctgaggca gggaggggct ggtgtgggag gctaagggca    420

gctgctaagt ttagggtggc tccttctctc ttcttagaga caacaggtgg ctggggcctc    480

agtgcccaga aaagaaaatg tcttagaggt atcggcatgg gcctggagga ggggggacag    540

ggcaggggga ggcatcttcc tcaggacatc gggtcctaga gggaccttgc ttcctagctg    600

ggcctttcct tctcctctat aaataccagc tctggtattt cgccttggca gctgttgctg    660

ctagggagac ggctggcttg acatgcatct cctgacaaaa cacaaacccg tggtgtgagt    720

gggtgtgggc ggtgtgagta gggggatgaa tcagagaggg ggcgagggag acaggggcgc    780

aggagtcagg caaaggcgat gcgggggtgc gactacacgc agttggaaac agtcgtcaga    840

agattctgga aactatcttg ctggctataa acttgaggga agcagaaggc caacattcct    900
```

-continued

```
cccaagggaa actgaggctc agagttaaaa cccaggtatc agtgatatgc atgtgccccg    960
gccagggtca ctctctgact aaccggtacc taccctacag gcctacctag agactctttt   1020
gaaaggatgg tagagacctg tccgggcttt gcccacagtc gttggaaacc tcagcatttt   1080
ctaggcaact tgtgcgaata aaacacttcg gggtccttc ttgttcattc caataaccta   1140
aaacctctcc tcggagaaaa tagggggcct caaacaaacg aaattctcta gcccgctttc   1200
cccaggataa ggcaggcatc caaatggaaa aaaagggggcc ggccgggggt ctcctgtcag   1260
ctccttgccc tgtgaaaccc agcaggcctg cctgtcttct gtcctcttgg ggctgtccag   1320
gggcgcaggc ctcttgcggg ggagctggcc tccccgcccc ctcgcctgtg gccgcccttt   1380
tcctggcagg acagagggat cctgcagctg tcaggggagg ggcgccgggg ggtgatgtca   1440
ggagggctac aaatagtgca gacagctaag ggctccgtc acccatcttc acatccactc   1500
cagccggctg cccgcccgct gcctcctctg tgcgtccgcc cagccagcct cgtccacgcc   1560
gccacctcta gaaagaggta agggtttaag ggatggttgg ttggtggggt attaatgttt   1620
aattacctgg agcacctgcc tgaaatcact tttttcagg ttggacgcgt atggtccgcg   1680
cgaggcacca gccgggtggg ctttgcctcc tgctgctgct gctctgccag ttcatggagg   1740
accgcagtgc ccaggctggg aactgctggc tccgtcaagc gaagaacggc cgctgccagg   1800
tcctgtacaa gaccgaactg agcaaggagg agtgctgcag caccggccgg ctgagcacct   1860
cgtggaccga ggaggacgtg aatgacaaca cactcttcaa gtggatgatt ttcaacgggg   1920
gcgcccccaa ctgcatcccc tgtaaagaaa cgtgtgagaa cgtggactgt ggacctggga   1980
aaaaatgccg aatgaacaag aagaacaaac cccgctgcgt ctgcgccccg gattgttcca   2040
acatcacctg gaagggtcca gtctgcgggc tggatgggaa aacctaccgc aatgaatgtg   2100
cactcctaaa ggcaagatgt aaagagcagc cagaactgga agtccagtac caaggcagat   2160
gtaaaaagac ttgtcgggat gttttctgtc caggcagctc cacatgtgtg gtggaccaga   2220
ccaataatgc ctactgtgtg acctgtaatc ggatttgccc agagcctgct tcctctgagc   2280
aatatctctg tgggaatgat ggagtcacct actccagtgc ctgccacctg agaaaggcta   2340
cctgcctgct gggcagatct attggattag cctatgaggg aaagtgtatc aaagcaaagt   2400
cctgtgaaga tatccagtgc actggtggga aaaaatgttt atgggatttc aaggttggga   2460
gaggccggtg ttccctctgt gatgagctgt gccctgacag taagtcggat gagcctgtct   2520
gtgccagtga caatgccact tatgccagcg agtgtgccat gaaggaagct gcctgctcct   2580
caggtgtgct actggaagta aagcactccg gatcttgcaa ctccatttcg gaagacaccg   2640
aggaagagga ggaagatgaa gaccaggact acagctttcc tatatcttct attctagagt   2700
gggtcgagag gtccggcggc ggagagggca gaggaagtct tctaacatgc ggtgacgtgg   2760
aggagaatcc cggcccaatg gaagatgcca aaaacattaa gaagggccca gcgccattct   2820
acccactcga agacgggacc gccggcgagc agctgcacaa agccatgaag cgctacgccc   2880
tggtgcccgg caccatcgcc tttaccgacg cacatatcga ggtggacatt acctacgccg   2940
agtacttcga gatgagcgtt cggctggcag aagctatgaa gcgctatggg ctgaatacaa   3000
accatcggat cgtggtgtgc agcgagaata gcttgcagtt cttcatgccc gtgttgggtg   3060
ccctgttcat cggtgtggct gtggccccag ctaacgacat ctacaacgag cgcgagctgc   3120
tgaacagcat gggcatcagc cagcccaccg tcgtattcgt gagcaagaaa gggctgcaaa   3180
agatcctcaa cgtgcaaaag aagctaccga tcatacaaaa gatcatcatc atggatagca   3240
```

```
agaccgacta ccagggcttc caaagcatgt acaccttcgt gacttcccat ttgccacccg   3300
gcttcaacga gtacgacttc gtgcccgaga gcttcgaccg ggacaaaacc atcgccctga   3360
tcatgaacag tagtggcagt accggattgc ccaagggcgt agccctaccg caccgcaccg   3420
cttgtgtccg attcagtcat gcccgcgacc ccatcttcgg caaccagatc atccccgaca   3480
ccgctatcct cagcgtggtg ccatttcacc acggcttcgg catgttcacc acgctgggct   3540
acttgatctg cggctttcgg gtcgtgctca tgtaccgctt cgaggaggag ctattcttgc   3600
gcagcttgca agactataag attcaatctg ccctgctggt gcccacacta tttagcttct   3660
tcgctaagag cactctcatc gacaagtacg acctaagcaa cttgcacgag atcgccagcg   3720
gcggggcgcc gctcagcaag gaggtaggtg aggccgtggc caaacgcttc cacctaccag   3780
gcatccgcca gggctacggc ctgacagaaa caaccagcgc cattctgatc acccccgaag   3840
gggacgacaa gcctggcgca gtaggcaagg tggtgccctt cttcgaggct aaggtggtgg   3900
acttggacac cggtaagaca ctgggtgtga accagcgcgg cgagctgtgc gtccgtggcc   3960
ccatgatcat gagcggctac gttaacaacc ccgaggctac aaacgctctc atcgacaagg   4020
acggctggct gcacagcggc gacatcgcct actgggacga ggacgagcac ttcttcatcg   4080
tggaccggct gaagagcctg atcaaataca agggctacca ggtagcccca gccgaactgg   4140
agagcatcct gctgcaacac cccaacatct tcgacgccgg ggtcgccggc ctgcccgacg   4200
acgatgccgg cgagctgccc gccgcagtcg tcgtgctgga acacggtaaa accatgaccg   4260
agaaggagat cgtggactat gtggccagcc aggttacaac cgccaagaag ctgcgcggtg   4320
gtgttgtgtt cgtggacgag gtgcctaaag gactgaccgg caagttggac gcccgcaaga   4380
tccgcgagat tctcattaag gccaagaagg gcggcaagat cgccgtgtaa aataaaagat   4440
ctttattttc attagatctg tgtgttggtt ttttgtgtga ggaaccccta gtgatggagt   4500
tggccactcc ctctctgcgc gctcgctcgc tcactgaggc cgggcgacca aaggtcgccc   4560
gacgcccggg ctttgcccgg gcggcctcag tgagcgagcg agcgcgcagc tgcctgcagg   4620
ggcgcctgat gcggtatttt ctccttacgc atctgtgcgg tatttcacac cgcatacgtc   4680
aaagcaacca tagtacgcgc cctgtagcgg cgcattaagc gcggcgggtg tggtggttac   4740
gcgcagcgtg accgctacac ttgccagcgc cctagcgccc gctcctttcg ctttcttccc   4800
ttcctttctc gccacgttcg ccggctttcc ccgtcaagct ctaaatcggg ggctcccttt   4860
agggttccga tttagtgctt tacggcacct cgaccccaaa aaacttgatt tgggtgatgg   4920
ttcacgtagt gggccatcgc cctgatagac ggtttttcgc cctttgacgt tggagtccac   4980
gttctttaat agtggactct tgttccaaac tggaacaaca ctcaacccta tctcgggcta   5040
ttcttttgat ttataaggga ttttgccgat ttcggcctat tggttaaaaa atgagctgat   5100
ttaacaaaaa tttaacgcga attttaacaa aatattaacg tttacaattt tatggtgcac   5160
tctcagtaca atctgctctg atgccgcata gttaagccag ccccgacacc cgccaacacc   5220
cgctgacgcg ccctgacggg cttgtctgct cccggcatcc gcttacagac aagctgtgac   5280
cgtctccggg agctgcatgt gtcagaggtt ttcaccgtca tcaccgaaac gcgcgagacg   5340
aaagggcctc gtgatacgcc tatttttata ggttaatgtc atgataataa tggtttctta   5400
gacgtcaggt ggcacttttc ggggaaatgt gcgcggaacc cctatttgtt tatttttcta   5460
aatacattca aatatgtatc cgctcatgag acaataaccc tgataaatgc ttcaataata   5520
ttgaaaaagg aagagtatga gtattcaaca tttccgtgtc gcccttattc ccttttttgc   5580
ggcattttgc cttcctgttt ttgctcaccc agaaacgctg gtgaaagtaa aagatgctga   5640
```

-continued

```
agatcagttg ggtgcacgag tgggttacat cgaactggat ctcaacagcg gtaagatcct   5700
tgagagtttt cgccccgaag aacgttttcc aatgatgagc acttttaaag ttctgctatg   5760
tggcgcggta ttatcccgta ttgacgccgg gcaagagcaa ctcggtcgcc gcatacacta   5820
ttctcagaat gacttggttg agtactcacc agtcacagaa aagcatctta cggatggcat   5880
gacagtaaga gaattatgca gtgctgccat aaccatgagt gataacactg cggccaactt   5940
acttctgaca acgatcggag gaccgaagga gctaaccgct tttttgcaca acatggggga   6000
tcatgtaact cgccttgatc gttgggaacc ggagctgaat gaagccatac caaacgacga   6060
gcgtgacacc acgatgcctg tagcaatggc aacaacgttg cgcaaactat taactggcga   6120
actacttact ctagcttccc ggcaacaatt aatagactgg atggaggcgg ataaagttgc   6180
aggaccactt ctgcgctcgg cccttccggc tggctggttt attgctgata aatctggagc   6240
cggtgagcgt gggtctcgcg gtatcattgc agcactgggg ccagatggta agccctcccg   6300
tatcgtagtt atctacacga cggggagtca ggcaactatg gatgaacgaa atagacagat   6360
cgctgagata ggtgcctcac tgattaagca ttggtaactg tcagaccaag tttactcata   6420
tatactttag attgatttaa aacttcattt ttaatttaaa aggatctagg tgaagatcct   6480
ttttgataat ctcatgacca aaatccctta acgtgagttt tcgttccact gagcgtcaga   6540
ccccgtagaa aagatcaaag gatcttcttg agatcctttt tttctgcgcg taatctgctg   6600
cttgcaaaca aaaaaaccac cgctaccagc ggtggtttgt ttgccggatc aagagctacc   6660
aactcttttt ccgaaggtaa ctggcttcag cagagcgcag ataccaaata ctgtccttct   6720
agtgtagccg tagttaggcc accacttcaa gaactctgta gcaccgccta catacctcgc   6780
tctgctaatc ctgttaccag tggctgctgc cagtggcgat aagtcgtgtc ttaccgggtt   6840
ggactcaaga cgatagttac cggataaggc gcagcggtcg ggctgaacgg ggggttcgtg   6900
cacacagccc agcttggagc gaacgaccta caccgaactg agatacctac agcgtgagct   6960
atgagaaagc gccacgcttc ccgaagggag aaaggcggac aggtatccgg taagcggcag   7020
ggtcggaaca ggagagcgca cgagggagct tccaggggga aacgcctggt atctttatag   7080
tcctgtcggg tttcgccacc tctgacttga gcgtcgattt ttgtgatgct cgtcaggggg   7140
gcggagccta tggaaaaacg ccagcaacgc ggccttttta cggttcctgg ccttttgctg   7200
gccttttgct cacatgt                                                  7217

<210> SEQ ID NO 46
<211> LENGTH: 49
<212> TYPE: DNA
<213> ORGANISM: Artificial Sequence
<220> FEATURE:
<223> OTHER INFORMATION: Synthetic polyadenylation signal

<400> SEQUENCE: 46

aataaaagat ctttattttc attagatctg tgtgttggtt ttttgtgtg                 49
```

MUSCLE-SPECIFIC NUCLEIC ACID REGULATORY ELEMENTS AND METHODS AND USE THEREOF

INCORPORATION BY CROSS-REFERENCE

This application is a U.S. National Phase of International Application No. PCT/EP2015/051081, filed Jan. 21, 2015, which claims priority to European Patent Application No. 14151960.3, filed Jan. 21, 2014, the disclosure of each of which is hereby incorporated by cross-reference in its entirety.

FIELD

The present invention relates to nucleic acid regulatory elements that are able to enhance muscle-specific expression of genes, methods employing these regulatory elements and use thereof. The invention further encompasses expression cassettes, vectors and pharmaceutical compositions comprising these regulatory elements. The present invention is particularly useful for applications using gene therapy, more particularly muscle-directed gene therapy, and for vaccination purposes.

BACKGROUND

Muscle is an attractive target for gene therapy. Gene delivery to muscle can be used to augment expression of muscle structural proteins, such as dystrophin and sarcoglycans, e.g. to treat muscular dystrophy. In addition, muscle can be used as a therapeutic platform to express non-muscle secretory/regulatory pathway proteins for diabetes, atherosclerosis, hemophilia, cancer, etc.

Efforts to deliver transgenes to muscle have focused on vectors derived from adenoviruses, retroviruses, lentiviruses, and adeno-associated viruses (AAV), and plasmids. Adenoviral vectors have a relatively large cloning capacity can be produced at high titers and display relatively efficient transduction of muscle. Unfortunately, these vectors can elicit a robust cellular immune response against viral and some transgene proteins. Moreover, they can evoke a rapid activation of the innate immune system that can contribute to a dose-limiting and potentially dangerous inflammatory immune response. Adenoviral vectors do not integrate into the host genome, so their ability to persist for long periods of time is unclear. Retroviral and lentiviral vectors integrate stably into the target cell genome, potentially allowing persistent gene transfer. Whereas lentiviral vectors can transduce both dividing and non-dividing cells, conventional retroviral vectors derived from Moloney murine leukemia virus (MoMLV) can only transduce dividing cells. Consequently, lentiviral vectors can be used to transduce non-dividing skeletal muscle cells, whereas these are refractory to transduction by direct injection with retroviral vectors. Nevertheless, even lentiviral transduction of skeletal muscle is not very efficient. Naked plasmid DNA displays a remarkable ability to transfer genes to muscle. Plasmids display minimal immunogenicity and toxicity, and have an extremely large cloning capacity. The primary disadvantage of plasmids is their relatively poor transfection efficiency under typical delivery protocols. Retention of plasmids is another important consideration.

Adeno-associated viral vector (AAV) is by far the most promising gene delivery vehicle for muscle-directed gene therapy. AAV's natural tropism to muscle cells, their long-term persistent transgene expression, their multiple serotypes, as well as their minimal immune response have made AAV vectors well suited for muscle-directed gene therapy. AAV vector can be delivered into both skeletal muscle and cardiac muscle by means of local, regional, and systemic administrations.

There however remain concerns regarding the efficacy and safety of some gene delivery approaches. The major limiting factors are: insufficient and/or transient transgene expression levels, and inappropriate expression of the transgene in unwanted cell types. In particular, it has been shown that inadvertent transgene expression in antigen-presenting cells (APCs), increases the risk of untoward immune responses against the gene-modified cells and/or the therapeutic transgene product that consequently curtails long-term gene expression.

Conventional methods of vector design relied on haphazard trial-and-error approaches whereby transcriptional enhancers were combined with promoters to boost expression levels. Though this could sometimes be effective, it often resulted in non-productive combinations that resulted in either modest or no increased expression levels of the gene of interest and/or loss of tissue specificity. Moreover, these conventional approaches did not take into account the importance of including evolutionary conserved regulatory motifs into the expression modules, which is particularly relevant for clinical translation.

A computational approach depending upon a modified distance difference matrix (DDM)-multidimensional scaling (MDS) strategy (De Bleser et al. 2007. Genome Biol 8, R83) has proven to be useful for the in silico identification of clusters of evolutionary conserved transcription factor binding site (TFBS) motifs associated with robust tissue-specific expression in liver (WO2009/130208) and heart (WO2011/051450).

There remains a need in the art for safe and efficient gene delivery to muscle.

SUMMARY

The present inventors have relied on a modified DDM-MDS strategy (De Bleser et al., 2007) combined with an enhanced screening strategy to identify evolutionarily conserved transcription factor binding site (TFBS) motifs associated with highly expressed muscle-specific genes defined herein as nucleic acid regulatory elements. As shown in the experimental section, the inventors could identify nucleic acid regulatory elements that specifically enhanced gene expression in both heart and skeletal muscle, and skeletal muscle-specific nucleic acid regulatory elements. These regulatory elements were subsequently validated in vivo yielding efficient and tissue-specific gene expression. This approach hence, allows for the use of lower and thus safer vector doses, while maximizing therapeutic efficacy.

The invention therefore provides the following aspects:

Aspect 1: a nucleic acid regulatory element for enhancing muscle-specific gene expression comprising, consisting essentially of, or consisting of a functional fragment of a sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, a sequence having at least 80%, preferably at least 85%, more preferably at least 90%, even more preferably at least 95%, such as 95%, 96%, 97%, 98%, or 99%, identity to any of these sequences, wherein said functional fragment comprises at least 20, preferably at least 25, more preferably at least 50, at least 100, at least 200 or at least 250, contiguous nucleotides from the sequence from which it is derived, and wherein said functional fragment comprises at least 1, preferably at least 5, more preferably at least 10 or at least 15, of the transcription factor binding sites (TFBS) that are present in the sequence from which it is derived.

Aspect 2: the nucleic acid regulatory element according to aspect 1 for enhancing cardiac and skeletal muscle-specific gene expression, comprising a functional fragment of a sequence selected from the group consisting of: SEQ ID NO:1, SEQ ID NO:2, SEQ ID NO:3, SEQ ID NO:4, SEQ ID NO:5, SEQ ID NO:6, or a sequence having at least 80%, preferably at least 85%, more preferably at least 90%, even more preferably at least 95%, such as 95%, 96%, 97%, 98%, or 99%, identity to any of these sequences, wherein said functional fragment comprise at least 20, preferably at least 25, more preferably at least 50, at least 100, at least 200 or at least 250, contiguous nucleotides from the sequence from which it is derived, and wherein said functional fragment comprises at least 1, preferably at least 5, more preferably at least 10 or at least 15, of the transcription factor binding sites (TFBS) that are present in the sequence from which it is derived.

Aspect 3: the nucleic acid regulatory element according to aspect 1 for enhancing skeletal muscle-specific gene expression comprising a functional fragment of a sequence selected from the group consisting of: SEQ ID NO:7, SEQ ID NO:8, SEQ ID NO:9, SEQ ID NO:10, SEQ ID NO:11, SEQ ID NO:12, SEQ ID NO:13, a sequence having at least 80%, preferably at least 85%, more preferably at least 90%, even more preferably at least 95%, such as 95%, 96%, 97%, 98%, or 99%, identity to any of these sequences, wherein said functional fragment comprise at least 20, preferably at least 25, more preferably at least 50, at least 100, at least 200 or at least 250, contiguous nucleotides from the sequence from which it is derived, and wherein said functional fragment comprises at least 1, preferably at least 5, more preferably at least 10 or at least 15, of the transcription factor binding sites (TFBS) that are present in the sequence from which it is derived.

Aspect 4: the nucleic acid regulatory element according to aspect 1, 2, or 3, comprising, consisting essentially of, or consisting of a sequence selected from the group consisting of: the nucleotide sequence from position 33 to 58 in SEQ ID NO:1; the nucleotide sequence from position 90 to 142 in SEQ ID NO:1; the nucleotide sequence from position 143 to 233 in SEQ ID NO:1; the nucleotide sequence from position 240 to 310 in SEQ ID NO:1; the nucleotide sequence from position 90 to 233 in SEQ ID NO:1; the nucleotide sequence from position 47 to 130 in SEQ ID NO:5; the nucleotide sequence from position 252 to 293 in SEQ ID NO:5; the nucleotide sequence from position 330 to 450 in SEQ ID NO:5; the nucleotide sequence from position 10 to 180 in SEQ ID NO:10 (i.e. SEQ ID NO:37); the nucleotide sequence from position 190 to 240 in SEQ ID NO:10 (i.e. SEQ ID NO:38); the nucleotide sequence from position 241 to 300 in SEQ ID NO:10 (i.e. SEQ ID NO:39); the nucleotide sequence from position 241 to 360 in SEQ ID NO:10 (i.e. SEQ ID NO:41); the nucleotide sequence from position 380 to 420 in SEQ ID NO:10 (i.e. SEQ ID NO:40); or a sequence having at least 95% identity to any of said sequences.

Aspect 5: the nucleic acid regulatory element according to any one of aspects 1 to 4 comprising, consisting essentially of or consisting of a sequence selected from the group consisting of: the nucleotide sequence from position 33 to 310 in SEQ ID NO:1; the nucleotide sequence from position 47 to 450 in SEQ ID NO:5; the nucleotide sequence from position 10 to 420 in SEQ ID NO:10, or a sequence having at least 95% identity to any of said sequences.

Aspect 6: the nucleic acid regulatory element according to any one of aspects 1 to 5, comprising, consisting essentially of, or consisting of a sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, or a sequence having at least 80%, preferably at least 85%, more preferably at least 90%, even more preferably at least 95%, such as 95%, 96%, 97%, 98%, or 99%, identity to any of these sequences.

Aspect 7: the nucleic acid regulatory element according to any one of aspects 1, 2, or 4 to 6 for enhancing cardiac and skeletal muscle-specific gene expression comprising, consisting essentially of, or consisting of a sequence selected from the group consisting of: SEQ ID NO:1, SEQ ID NO:2, SEQ ID NO:3, SEQ ID NO:4, SEQ ID NO:5, SEQ ID NO:6, or a sequence having at least 80%, preferably at least 85%, more preferably at least 90%, even more preferably at least 95%, such as 95%, 96%, 97%, 98%, or 99%, identity to any of these sequences.

Aspect 8: the nucleic acid regulatory element according to any one of aspects 1, 3 to 6 for enhancing skeletal muscle-specific gene expression comprising, consisting essentially of, or consisting of a sequence selected from the group consisting of: SEQ ID NO:7, SEQ ID NO:8, SEQ ID NO:9, SEQ ID NO:10, SEQ ID NO:11, SEQ ID NO:12, SEQ ID NO:13, or a sequence having at least 80%, preferably at least 85%, more preferably at least 90%, even more preferably at least 95%, such as 95%, 96%, 97%, 98%, or 99%, identity to any of these sequences.

Aspect 9: the nucleic acid regulatory element according to any one of aspects 1 to 8, comprising, consisting essentially of, or consisting of a sequence selected from the group consisting of: SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, a functional fragment thereof comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or SEQ ID NO:13, or a sequence having at least 80%, preferably at least 85%, more preferably at least 90%, even more preferably at least 95%, such as 95%, 96%, 97%, 98%, or 99%, identity to any of these sequences.

Aspect 10: the nucleic acid regulatory element according to any one of aspects 1, 2, 4 to 7, 9, comprising, consisting essentially of, or consisting of a sequence selected from the group consisting of: SEQ ID NO:17, SEQ ID NO:18, SEQ ID NO:19, SEQ ID NO:20, SEQ ID NO:21, SEQ ID NO:22, a functional fragment thereof comprising SEQ ID NO:1, SEQ ID NO:2, SEQ ID NO:3, SEQ ID NO:4, SEQ ID NO:5, or SEQ ID NO:6, or a sequence having at least 80%, preferably at least 85%, more preferably at least 90%, even more preferably at least 95%, such as 95%, 96%, 97%, 98%, or 99%, identity to any of these sequences.

Aspect 11: the nucleic acid regulatory element according to any one of aspects 1, 3 to 6, 8, or 9, comprising, consisting essentially of, or consisting of a sequence selected from the group consisting of: SEQ ID NO:23, SEQ ID NO:24, SEQ ID NO:25, SEQ ID NO:26, SEQ ID NO:27, SEQ ID NO:28, SEQ ID NO:29, a functional fragment thereof comprising SEQ ID NO:7, SEQ ID NO:8, SEQ ID NO:9, SEQ ID NO:10, SEQ ID NO:11, SEQ ID NO:12, or SEQ ID NO:13, or a sequence having at least 80%, preferably at least 85%, more preferably at least 90%, even more preferably at least 95%, such as 95%, 96%, 97%, 98%, or 99%, identity to any of these sequences.

Aspect 12: a nucleic acid regulatory element for enhancing muscle-specific gene expression comprising, consisting essentially of, or consisting of the complement of a sequence as defined in any one of aspects 1 to 11.

Aspect 13: a nucleic acid regulatory element for enhancing muscle-specific gene expression hybridizing under stringent conditions to the nucleic acid regulatory element according to any one of aspects 1 to 12.

Aspect 14: the nucleic acid regulatory element according to any one of aspects 1 to 13, having a maximal length of 1000 nucleotides, preferably 800 nucleotides, more preferably 600 nucleotides, such as 550 nucleotides, 500 nucleotides, 450 nucleotides, 400 nucleotides, 350 nucleotides, or 300 nucleotides, still comprising the regulatory element defined by any one of SEQ ID Nos: 1-13, or any one of the functional fragments thereof defined in any one of aspects 3 to 5.

Aspect 15: use of the nucleic acid regulatory element according to any one aspects 1 to 14 in a nucleic acid expression cassette, or a vector, more particularly for enhancing muscle-specific expression of said nucleic acid expression cassette or vector.

Aspect 16: a nucleic acid expression cassette comprising at least one, such as one, two, three, four, five or more, nucleic acid regulatory element according to any one of aspects 1 to 14, operably linked to a promoter.

Aspect 17: the nucleic acid expression cassette according to aspect 16, wherein the nucleic acid regulatory element is operably linked to a promoter and a transgene.

Aspect 18: the nucleic acid expression cassette according any one of aspects 16 or 17, wherein the promoter is a muscle-specific promoter, preferably the promoter from the desmin (DES) gene.

Aspect 19: the nucleic acid expression cassette according to any one of aspects 17 or 18, wherein the transgene encodes a therapeutic protein or an immunogenic protein.

Aspect 20: the nucleic acid expression cassette according to any one of aspects 17 to 19, wherein the transgene encodes a secretable protein or a structural protein, such as dystrophin or sarcoglycan.

Aspect 21: the nucleic acid expression cassette according to any one of aspects 16 to 20, further comprising an intron, preferably the Minute Virus of Mouse (MVM) intron.

Aspect 22: the nucleic acid expression cassette according to any one of aspects 16 to 21, further comprising a polyadenylation signal, preferably the Simian Virus 40 (SV40) polyadenylation signal.

Aspect 23: a vector comprising the nucleic acid regulatory element according to any one of aspects 1 to 14, or the nucleic acid expression cassette according to any one of aspects 16 to 22.

Aspect 24: the vector according to aspect 23, which is a viral vector, preferably an adeno-associated viral (AAV) vector, more preferably an AAV9 vector.

Aspect 25: the vector according to aspect 23, which is a non-viral vector, preferably a plasmid, a minicircle or a transposon-based vector, such as a PiggyBac-based vector or a Sleeping Beauty-based vector.

Aspect 26: a pharmaceutical composition comprising the nucleic acid expression cassette according to any one of aspects 16 to 22, or the vector according to any one of aspects 23 to 25, and a pharmaceutically acceptable carrier.

Aspect 27: the nucleic acid regulatory element according to any one of aspects 1 to 14, the nucleic acid expression cassette according to any one of aspects 16 to 22, the vector according to any one of aspects 23 to 25, or the pharmaceutical composition according to aspect 26 for use in medicine.

Aspect 28: the nucleic acid regulatory element according to any one of aspects 1 to 14, the nucleic acid expression cassette according to any one of aspects 16 to 22, the vector according to any one of aspects 23 to 25, or the pharmaceutical composition according to aspect 26 for use in gene therapy, preferably muscle-directed gene therapy.

Aspect 29: the nucleic acid regulatory element, the nucleic acid expression cassette, the vector, or the pharmaceutical composition according for use according to aspect 28, wherein the gene therapy is for muscular dystrophy (e.g. Duchenne muscular dystrophy (DMD)/Becker muscular dystrophy (BMD)), myotonic dystrophy, neuromuscular disease, motor neuron diseases (MND), such as e.g. Charcot-Marie-Tooth disease (CMT), spinal muscular atrophy (SMA), and amyotrophic lateral sclerosis (ALS), Emery-Dreifuss muscular dystrophy, facioscapulohumeral muscular dystrophy (FSHD), congenital muscular dystrophies, congenital myopathies, limb girdle muscular dystrophy, metabolic myopathies, muscle inflammatory diseases, myasthenia, mitochondrial myopathies, anomalies of ionic channels, nuclear envelop diseases, cardiomyopathies, cardiac hypertrophy, heart failure, distal myopathies, cardiovascular diseases, hemophilia, including hemophilia A and B, and diabetes.

Aspect 30: the nucleic acid regulatory element according to any one of aspects 1 to 14, the nucleic acid expression cassette according to any one of aspects 16 to 22, the vector according to any one of aspects 23 to 25, or the pharmaceutical composition according to aspect 26 for use as a vaccine, preferably a prophylactic vaccine, or for use in vaccination therapy, preferably prophylactic vaccination.

Aspect 31: A method, preferably an in vitro or ex vivo method, for expressing a transgene product in muscle cells, preferably heart muscle cells and/or skeletal muscle cells, comprising:

introducing the nucleic acid expression cassette according to any one of aspects 16 to 22, or the vector according to any one of aspects 23 to 25 into the muscle cells;

expressing the transgene product in the muscle cells.

BRIEF DESCRIPTION OF DRAWINGS

FIG. 2: Nucleotide sequences of the cardiac and skeletal muscle-specific regulatory elements CSk-SH1 (A, SEQ ID NO: 1), CSk-SH2 (B, SEQ ID NO: 2), CSk-SH3 (C, SEQ ID NO: 3), CSk-SH4 (D, SEQ ID NO: 4), CSk-SH5 (E, SEQ ID NO: 5), and CSk-SH6 (F, SEQ ID NO: 6).

FIG. 6: Transduction efficiency in different organs of mice injected with AAV9sc-CSk-SH1-Des-Luc2 (CSk-SH1) (A) or AAV9sc-CSk-SH5-Des-Luc2 (CSk-SH5) (B). AAV copy number relative to 100 ng of genomic DNA was determined for both constructs at a dose of $5\times10^9$ vg/mouse.

FIG. 7: Nucleotide sequences of the muscle-specific regulatory elements Sk-SH1 (A, SEQ ID NO: 7), Sk-SH2 (B, SEQ ID NO: 8), Sk-SH3 (C, SEQ ID NO: 9), Sk-SH4 (D, SEQ ID NO: 10), Sk-SH5 (E, SEQ ID NO: 11), Sk-SH6 (F, SEQ ID NO: 12), Sk-SH7 (G, SEQ ID NO: 13).

FIG. 13: Transduction efficiency in different organs of mice injected with AAV9sc-Sk-SH4-Des-MVM-Luc-pA vector (A) or AAV9sc-Sk-SH1-Des-MVM-Luc-pA vector (B). AAV copy number relative to 100 ng of genomic DNA was determined for both vectors (n=3).

DESCRIPTION

Figure 1:
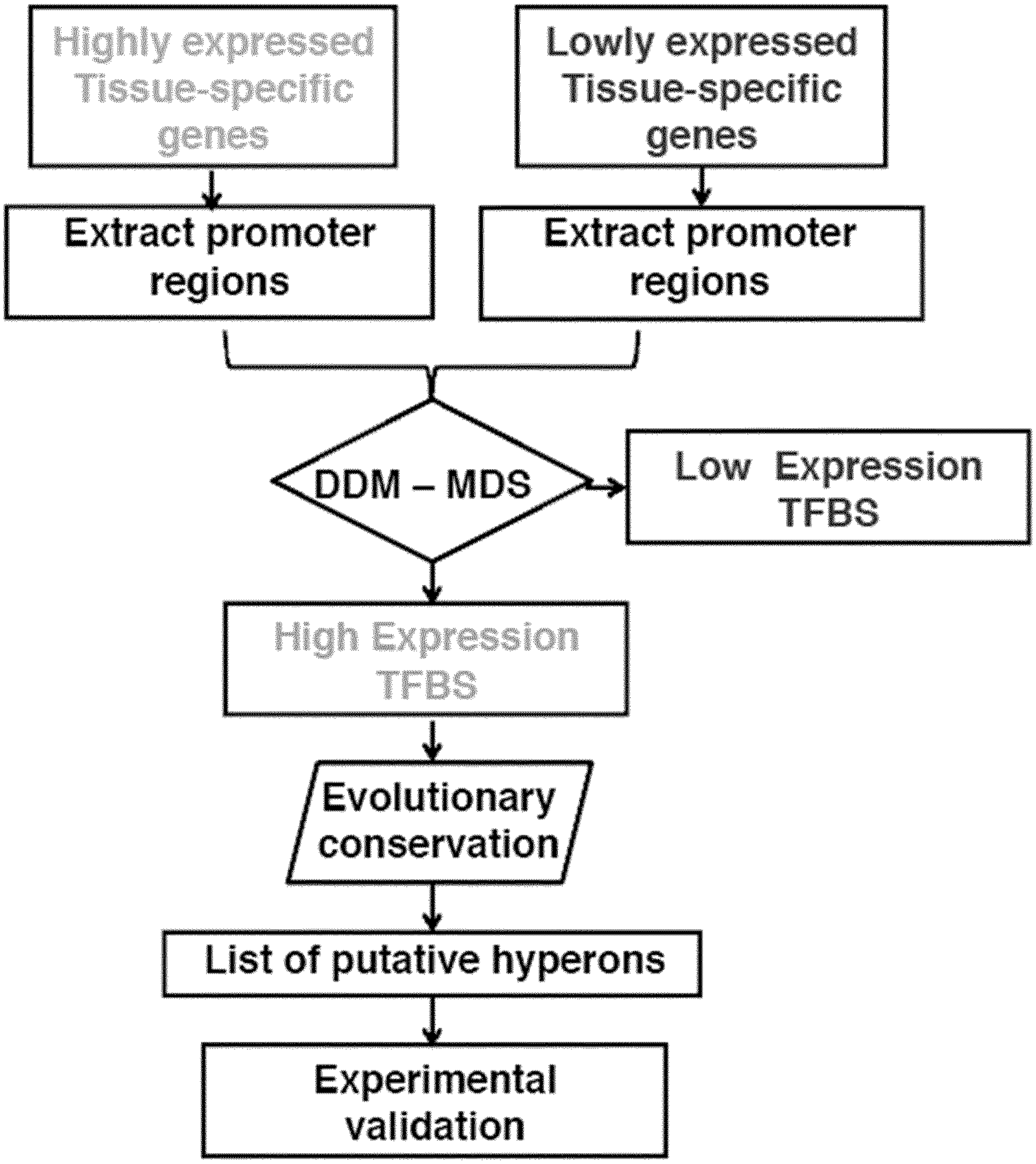
FIG. 1: Flow diagram of the identification and validation of nucleic acid regulatory elements. A computational approach was used to identify the nucleic acid regulatory elements involving the following steps: (1) identification of tissue-specific genes that are highly expressed e.g. based on statistical analysis of micro-array expression data of normal human tissues; (2) extraction of the corresponding promoter sequences from publicly available databases; (3) identification of the regulatory modules and the transcription factor binding sites (TFBS) they contain (4) Next, the genomic context of the highly expressed genes was searched for evolutionary conserved clusters of TFBS (i.e. nucleic acid regulatory elements). The identified nucleic acid regulatory elements were de novo designed and validated in vivo by testing whether inclusion in a construct increases expression of a reporter gene.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms also encompass "consisting of" and "consisting essentially of", which enjoy well-established meanings in patent terminology.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Whereas the terms "one or more" or "at least one", such as one or more members or at least one member of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members. In another example, "one or more" or "at least one" may refer to 1, 2, 3, 4, 5, 6, 7 or more.

The discussion of the background to the invention herein is included to explain the context of the invention. This is not to be taken as an admission that any of the material referred to was published, known, or part of the common general knowledge in any country as of the priority date of any of the claims.

Throughout this disclosure, various publications, patents and published patent specifications are referenced by an identifying citation. All documents cited in the present specification are hereby incorporated by reference in their entirety. In particular, the teachings or sections of such documents herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the invention. When specific terms are defined in connection with a particular aspect of the invention or a particular embodiment of the invention, such connotation is meant to apply throughout this specification, i.e., also in the context of other aspects or embodiments of the invention, unless otherwise defined.

In the following passages, different aspects or embodiments of the invention are defined in more detail. Each aspect or embodiment so defined may be combined with any other aspect(s) or embodiment(s) unless clearly indicated to the contrary. In particular, any feature indicated as being preferred or advantageous may be combined with any other feature or features indicated as being preferred or advantageous.

Reference throughout this specification to "one embodiment", "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

For general methods relating to the invention, reference is made inter alia to well-known textbooks, including, e.g., "Molecular Cloning: A Laboratory Manual, 2nd Ed." (Sambrook et al., 1989), "Current Protocols in Molecular Biology" (Ausubel et al., 1987).

In an aspect, the invention relates to a nucleic acid regulatory element for enhancing muscle-specific gene expression comprising, consisting essentially of (i.e., the regulatory element may for instance additionally comprise sequences used for cloning purposes, but the indicated sequences make up the essential part of the regulatory element, e.g. they do not form part of a larger regulatory region such as a promoter), or consisting of a sequence selected from the group consisting of: SEQ ID NO:1, SEQ ID NO: 2, SEQ ID NO:3, SEQ ID NO:4, SEQ ID NO:5, SEQ ID NO:6, SEQ ID NO: 7, SEQ ID NO: 8, SEQ ID NO: 9, SEQ ID NO: 10, SEQ ID NO: 11, SEQ ID NO: 12, SEQ ID NO: 13, a sequence having at least 80%, preferably at least 85%, more preferably at least 90%, even more preferably at least 95%, such as 95%, 96%, 97%, 98%, or 99%, identity to any of these sequences, or a functional fragment thereof (i.e. a functional fragment of a sequence selected from the group consisting of: SEQ ID NO:1, SEQ ID NO: 2, SEQ ID NO:3, SEQ ID NO:4, SEQ ID NO:5, SEQ ID NO:6, SEQ ID NO: 7, SEQ ID NO: 8, SEQ ID NO: 9, SEQ ID NO: 10, SEQ ID NO: 11, SEQ ID NO: 12, SEQ ID NO: 13, or of a sequence having high percentage sequence identity to any of said sequences).

A 'regulatory element' as used herein refers to a transcriptional control element, in particular a non-coding cis-acting transcriptional control element, capable of regulating and/or controlling transcription of a gene, in particular tissue-specific transcription of a gene. Regulatory elements comprise at least one transcription factor binding site (TFBS), more in particular at least one binding site for a tissue-specific transcription factor, most particularly at least one binding site for a muscle-specific transcription factor. Typically, regulatory elements as used herein increase or enhance promoter-driven gene expression when compared to the transcription of the gene from the promoter alone, without the regulatory elements. Thus, regulatory elements particularly comprise enhancer sequences, although it is to be understood that the regulatory elements enhancing transcription are not limited to typical far upstream enhancer sequences, but may occur at any distance of the gene they regulate. Indeed, it is known in the art that sequences regulating transcription may be situated either upstream (e.g. in the promoter region) or downstream (e.g. in the 3'UTR) of the gene they regulate in vivo, and may be located in the immediate vicinity of the gene or further away. Of note, although regulatory elements as disclosed herein typically comprise naturally occurring sequences, combinations of (parts of) such regulatory elements or several copies of a regulatory element, i.e. regulatory elements comprising non-naturally occurring sequences, are themselves also envisaged as regulatory element. Regulatory elements as used herein may comprise part of a larger sequence involved in transcriptional control, e.g. part of a promoter sequence. However, regulatory elements alone are typically not sufficient to initiate transcription, but require a promoter to this end. The regulatory elements disclosed herein are provided as nucleic acid molecules, i.e. isolated nucleic acids, or isolated nucleic acid molecules. Said nucleic acid regulatory element hence have a sequence which is only a small part of the naturally occurring genomic sequence and hence is not naturally occurring as such, but is isolated therefrom.

The term "nucleic acid" as used herein typically refers to an oligomer or polymer (preferably a linear polymer) of any length composed essentially of nucleotides. A nucleotide unit commonly includes a heterocyclic base, a sugar group, and at least one, e.g. one, two, or three, phosphate groups, including modified or substituted phosphate groups. Heterocyclic bases may include inter alia purine and pyrimidine bases such as adenine (A), guanine (G), cytosine (C), thymine (T) and uracil (U) which are widespread in naturally-occurring nucleic acids, other naturally-occurring bases (e.g., xanthine, inosine, hypoxanthine) as well as chemically or biochemically modified (e.g., methylated), non-natural or derivatised bases. Sugar groups may include inter alia pentose (pentofuranose) groups such as preferably ribose and/or 2-deoxyribose common in naturally-occurring nucleic acids, or arabinose, 2-deoxyarabinose, threose or hexose sugar groups, as well as modified or substituted sugar groups. Nucleic acids as intended herein may include naturally occurring nucleotides, modified nucleotides or mixtures thereof. A modified nucleotide may include a modified heterocyclic base, a modified sugar moiety, a modified phosphate group or a combination thereof. Modifications of phosphate groups or sugars may be introduced to improve stability, resistance to enzymatic degradation, or some other useful property. The term "nucleic acid" further preferably encompasses DNA, RNA and DNA/RNA hybrid molecules, specifically including hnRNA, pre-mRNA, mRNA, cDNA, genomic DNA, amplification products, oligonucleotides, and synthetic (e.g., chemically synthesised) DNA, RNA or DNA/RNA hybrids. A nucleic acid can be naturally occurring, e.g., present in or isolated from nature; or can be non-naturally occurring, e.g., recombinant, i.e., produced by recombinant DNA technology, and/or partly or entirely, chemically or biochemically synthesised. A "nucleic acid" can be double-stranded, partly double stranded, or single-stranded. Where single-stranded, the nucleic acid can be the sense strand or the antisense strand. In addition, nucleic acid can be circular or linear.

As used herein "transcription factor binding site", "transcription factor binding sequence" or "TFBS" refers to a sequence of a nucleic acid region to which transcription factors bind. Non-limiting examples of TFBS include binding sites for transcription factor 3, also known as TCF3 or E2A; binding sites for nuclear factor I, also known as NF1; binding sites for CCAAT-enhancer-binding protein, also known as C/EBP; binding sites for myogenic differentiation, also known as MyoD; binding sites for sterol regulatory element-binding protein, also known as SREBP; binding sites for leukemia/lymphoma-related factor, also known as LRF; binding sites for protein 53, also known as p53; binding sites for hepatocyte nuclear factor 3-alpha, also known as HNF3a; binding sites for hepatocyte nuclear factor 3-beta, also known as HNF3b; binding sites for hepatocyte nuclear factor 4, also known as HNF4; binding sites for myocyte-specific enhancer factor 2A, also known as MEF2A or RSRFC4; binding sites for peroxisome proliferator-activated receptor, also known as PPAR; binding sites for serum response factor, also known as SRF; binding sites for transcription activator-like protein 1 b, also known as Tall_b. Transcription factor binding sites may be found in databases such as Transfac®.

Sequences disclosed herein may be part of sequences of regulatory elements capable of controlling transcription of muscle-specific genes in vivo, in particular controlling the following genes: desmin also known as DES, CSM1 or CSM2; actinin, alpha 2 also known as ACTN2 or CMD1AA; filamin-C (FLNC) also known as actin-binding-like protein (ABLP), filamin-2 (FLN2), ABP-280, ABP280A, ABPA, ABPL, MFM5, or MPD4; sarcoplasmic/endoplasmic reticulum calcium ATPase 1 also known as ATP2A1, ATP2A, or SERCA1; troponin I type 1 (slow skeletal muscle) also known as TNNI1, SSTNI, or TNN1; myosin light chain phosphorylatable fast skeletal muscle (MYLPF); myosin-1 also known as MYH1, MYHSA1, MYHa; MyHC-2X/D, or MyHC-2x; tropomyosin alpha-3 chain also known as TPM3, CFTD, NEM1, OK/SW-c1.5, TM-5, TM3, TM30, TM30 nm, TM5, TPMsk3, TRK, hTM5, or hscp30; and ankyrin repeat domain-containing protein 2 also known as ANKRD2, or ARPP. Accordingly, in embodiments, the nucleic acid regulatory elements disclosed herein comprise a sequence from Des regulatory elements, i.e. regulatory elements that control expression of the Des gene in vivo, e.g. regulatory elements comprising SEQ ID NO:1, SEQ ID NO: 17, SEQ ID NO:2, SEQ ID NO:18, or functional fragments thereof. In embodiments, the nucleic acid regulatory elements disclosed herein comprise a sequence from ACTN2 regulatory elements, i.e. regulatory elements that control expression of the ACTN2 gene in vivo, e.g. regulatory elements comprising SEQ ID NO:3, SEQ ID NO:19, SEQ ID NO:4, SEQ ID NO:20, or functional fragments thereof. In embodiments, the nucleic acid regulatory elements disclosed herein comprise a sequence from FLNC regulatory elements, i.e. regulatory elements that control expression of the FLNC gene in vivo, e.g. regulatory elements comprising SEQ ID NO:5, SEQ ID NO:21, SEQ ID NO:6, SEQ ID NO:22, or functional fragments thereof. In embodiments, the nucleic acid regulatory elements disclosed herein comprise a sequence from ATP2A1 regulatory elements, i.e. regulatory elements that control expression of the ATP2A1 gene in vivo, e.g. regulatory elements comprising SEQ ID NO:7, SEQ ID NO:23, or functional fragments thereof. In embodiments, the nucleic acid regulatory elements disclosed herein comprise a sequence from TNNI1 regulatory elements, i.e. regulatory elements that control expression of the TNNI1 gene in vivo, e.g. regulatory elements comprising SEQ ID NO:8, SEQ ID NO:24, SEQ ID NO:9, SEQ ID NO:25, or functional fragments thereof. In embodiments, the nucleic acid regulatory elements disclosed herein comprise a sequence from MYLPF regulatory elements, i.e. regulatory elements that control expression of the MYLPF gene in vivo, e.g. regulatory elements comprising SEQ ID NO:10, SEQ ID NO:26, or functional fragments thereof, such as regulatory elements comprising or consisting of SEQ ID NO:37, SEQ ID NO:38, SEQ ID NO:39, SEQ ID NO:40 or SEQ ID NO:41. In embodiments, the nucleic acid regulatory elements disclosed herein comprise a sequence from MYH1 regulatory elements, i.e. regulatory elements that control expression of the MYH1 gene in vivo, e.g. regulatory elements comprising SEQ ID NO:11, SEQ ID NO:27, or functional fragments thereof. In embodiments, the nucleic acid regulatory elements disclosed herein comprise a sequence from TPM3 regulatory elements, i.e. regulatory elements that control expression of the TPM3 gene in vivo, e.g. regulatory elements comprising SEQ ID NO:12, SEQ ID NO:28, or functional fragments thereof. In embodiments, the nucleic acid regulatory elements disclosed herein comprise a sequence from ANKRD2 regulatory elements, i.e. regulatory elements that control expression of the ANKRD2 gene in vivo, e.g. regulatory elements comprising SEQ ID NO:13, SEQ ID NO:29, or functional fragments thereof.

As used herein, the terms "identity" and "identical" and the like refer to the sequence similarity between two polymeric molecules, e.g., between two nucleic acid molecules, e.g., two DNA molecules. Sequence alignments and determination of sequence identity can be done, e.g., using the Basic Local Alignment Search Tool (BLAST) originally described by Altschul et al. 1990 (J Mol Biol 215: 403-10), such as the "Blast 2 sequences" algorithm described by Tatusova and Madden 1999 (FEMS Microbiol Lett 174: 247-250). Typically, the percentage sequence identity is calculated over the entire length of the sequence. As used herein, the term "substantially identical" denotes at least 90%, preferably at least 95%, such as 95%, 96%, 97%, 98% or 99%, sequence identity.

The term 'functional fragment' as used in the application refers to fragments of the regulatory element sequences disclosed herein that retain the capability of regulating muscle-specific expression, i.e. they can still confer tissue specificity and they are capable of regulating expression of a (trans)gene in the same way (although possibly not to the same extent) as the sequence from which they are derived. Functional fragments may preferably comprise at least 20, at least 25, at least 30, at least 35, at least 40, at least 45, at least 50, at least 60, at least 70, at least 80, at least 90, at least 100, at least 120, at least 150, at least 200, at least 250, at least 300, at least 350, or at least 400 contiguous nucleotides from the sequence from which they are derived. Also preferably, functional fragments may comprise at least 1, more preferably at least 2, at least 3, or at least 4, even more preferably at least 5, at least 10, or at least 15, of the transcription factor binding sites (TFBS) that are present in the sequence from which they are derived.

"Muscle-specific expression" as used in the application, refers to the preferential or predominant expression of a (trans)gene (as RNA and/or polypeptide) in muscles or muscle tissue, as compared to other (i.e. non-muscle) tissues. According to particular embodiments, at least 50%, more particularly at least 60%, at least 70%, at least 75%, at least 80%, at least 85%, at least 90%, at least 95%, at least 98%, at least 99% or 100% of the (trans)gene expression occurs within muscle. According to a particular embodiment, muscle-specific expression entails that there is no 'leakage' of expressed gene product to other organs or tissue than muscle, such as lung, liver, brain, kidney and/or spleen.

As used herein "cardiac and skeletal muscle-specific expression" refers to the preferential or predominant expression of a (trans)gene in heart, in particular heart muscle, and skeletal muscle. According to particular embodiments, at least 50%, more particularly at least 60%, at least 70%, at least 75%, at least 80%, at least 85%, at least 90%, at least 95%, at least 98%, at least 99% or 100% of the (trans)gene expression occurs within heart and skeletal muscle. Thus, according to particular embodiments, less than 10%, less than 5%, less than 2% or even less than 1% of the (trans) gene expression occurs in an organ or tissue other than heart and skeletal muscle.

As used herein "skeletal muscle-specific expression" refers to the preferential or predominant expression of a (trans)gene in skeletal muscle. According to particular embodiments, at least 50%, more particularly at least 60%, at least 70%, at least 75%, at least 80%, at least 85%, at least 90%, at least 95%, at least 98%, at least 99% or 100% of the (trans)gene expression occurs within skeletal muscle. Thus, according to particular embodiments, less than 10%, less than 5%, less than 2% or even less than 1% of the (trans) gene expression occurs in an organ or tissue other than skeletal muscle.

The same applies mutatis mutandis for myocyte-specific and myoblast-specific expression, which may be considered as a particular form of muscle-specific expression. Throughout the application, where muscle-specific is mentioned in the context of expression, myocyte-specific and myoblast-specific expression are also explicitly envisaged. Similarly, where cardiac and skeletal muscle-specific expression is used in the application, cardiomyocyte and skeletal myocyte-specific expression and cardiac myoblast and skeletal myoblast-specific expression is also explicitly envisaged. Similarly, where skeletal muscle-specific expression is used in the application, skeletal myocyte-specific and skeletal myoblast-specific expression is also explicitly envisaged.

As used herein, the terms "heart muscle" or "cardiac muscle" refer to the autonomically regulated, striated muscle type found in the heart.

As used herein, the term "skeletal muscle" refers to the voluntarily controlled, striated muscle type that is attached to the skeleton. Non-limiting examples of skeletal muscle include the biceps, the triceps, the quadriceps, the tibialis interior, and the gastrocnemius muscle.

The term "myocyte," as used herein, refers to a cell that has been differentiated from a progenitor myoblast such that it is capable of expressing muscle-specific phenotype under appropriate conditions. Terminally differentiated myocytes fuse with one another to form myotubes, a major constituent of muscle fibers. The term "myocyte" also refers to myocytes that are de-differentiated. The term includes cells in vivo and cells cultured ex vivo regardless of whether such cells are primary or passaged.

The term "myoblast" as used herein, refers to an embryonic cell in the mesoderm that differentiates to give rise to a muscle cell or myocyte. The term includes cells in vivo and cells cultured ex vivo regardless of whether such cells are primary or passaged.

In embodiments, the invention relates to a nucleic acid regulatory element for enhancing muscle-specific gene expression comprising, consisting essentially of, or consisting of a functional fragment of a sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, a sequence having at least 80%, preferably at least 85%, more preferably at least 90%, even more preferably at least 95%, such as 95%, 96%, 97%, 98%, or 99%, identity to any of these sequences, wherein said functional fragment comprises at least 20, preferably at least 25, more preferably at least 50, at least 100, at least 200 or at least 250, contiguous nucleotides from the sequence from which it is derived, and wherein said functional fragment comprises at least 1, preferably at least 5, more preferably at least 10 or at least 15, of the transcription factor binding sites (TFBS) that are present in the sequence from which it is derived.

In further embodiments, the invention relates to a nucleic acid regulatory element for enhancing cardiac and skeletal muscle-specific gene expression comprising a functional fragment of a sequence selected from the group consisting of: SEQ ID NO:1, SEQ ID NO:2, SEQ ID NO:3, SEQ ID NO:4, SEQ ID NO:5, SEQ ID NO:6, or a sequence having at least 80%, preferably at least 85%, more preferably at least 90%, even more preferably at least 95%, such as 95%, 96%, 97%, 98%, or 99%, identity to any of these sequences, wherein said functional fragment comprise at least 20, preferably at least 25, more preferably at least 50, at least 100, at least 200 or at least 250, contiguous nucleotides from the sequence from which it is derived, and wherein said functional fragment comprises at least 1, preferably at least 5, more preferably at least 10 or at least 15, of the transcription factor binding sites (TFBS) that are present in the sequence from which it is derived.

In yet further embodiments, the invention relates to a nucleic acid regulatory element for enhancing cardiac and skeletal muscle-specific gene expression comprising a functional fragment of a sequence selected from the group consisting of: SEQ ID NO:1 and SEQ ID NO:5, or a sequence having at least 80%, preferably at least 85%, more preferably at least 90%, even more preferably at least 95%, such as 95%, 96%, 97%, 98%, or 99%, identity to any of these sequences, wherein said functional fragment consists of the nucleotide sequence from position 33 to 58 in SEQ ID NO:1; the nucleotide sequence from position 90 to 142 in SEQ ID NO:1; the nucleotide sequence from position 143 to 233 in SEQ ID NO:1; the nucleotide sequence from position 240 to 310 in SEQ ID NO:1; the nucleotide sequence from position 90 to 233 in SEQ ID NO:1; the nucleotide sequence from position 47 to 130 in SEQ ID NO:5; the nucleotide sequence from position 252 to 293 in SEQ ID NO:5; or the nucleotide sequence from position 330 to 450 in SEQ ID NO:5.

In further embodiments, the invention relates to a nucleic acid regulatory element for enhancing skeletal muscle-specific gene expression comprising a functional fragment of a sequence selected from the group consisting of: SEQ ID NO:7, SEQ ID NO:8, SEQ ID NO:9, SEQ ID NO:10, SEQ ID NO:11, SEQ ID NO:12, SEQ ID NO:13, a sequence having at least 80%, preferably at least 85%, more preferably at least 90%, even more preferably at least 95%, such as 95%, 96%, 97%, 98%, or 99%, identity to any of these sequences, wherein said functional fragment comprise at least 20, preferably at least 25, more preferably at least 50, at least 100, at least 200 or at least 250, contiguous nucleotides from the sequence from which it is derived, and wherein said functional fragment comprises at least 1, preferably at least 5, more preferably at least 10 or at least 15, of the transcription factor binding sites (TFBS) that are present in the sequence from which it is derived.

In yet further embodiments, the invention relates to a nucleic acid regulatory element for enhancing skeletal muscle-specific gene expression comprising a functional fragment of SEQ ID NO:10 or a sequence having at least 80%, preferably at least 85%, more preferably at least 90%, even more preferably at least 95%, such as 95%, 96%, 97%, 98%, or 99%, identity to SEQ ID NO:10, wherein said functional fragment consists of the nucleotide sequence from position 10 to 180 in SEQ ID NO:10; the nucleotide sequence from position 190 to 240 in SEQ ID NO:10; the nucleotide sequence from position 241 to 300 in SEQ ID NO:10; the nucleotide sequence from position 241 to 360 in SEQ ID NO:10; or the nucleotide sequence from position 380 to 420 in SEQ ID NO:10.

In certain embodiments, the nucleic acid regulatory elements of the invention comprise or consist of a sequence selected from the group consisting of: the nucleotide sequence from position 33 to 58 in SEQ ID NO:1; the nucleotide sequence from position 90 to 142 in SEQ ID NO:1; the nucleotide sequence from position 143 to 233 in SEQ ID NO:1; the nucleotide sequence from position 240 to 310 in SEQ ID NO:1; the nucleotide sequence from position 90 to 233 in SEQ ID NO:1; the nucleotide sequence from position 47 to 130 in SEQ ID NO:5; the nucleotide sequence from position 252 to 293 in SEQ ID NO:5; the nucleotide sequence from position 330 to 450 in SEQ ID NO:5; the nucleotide sequence from position 10 to 180 in SEQ ID NO:10; the nucleotide sequence from position 190 to 240 in SEQ ID NO:10; the nucleotide sequence from position 241 to 300 in SEQ ID NO:10; the nucleotide sequence from position 241 to 360 in SEQ ID NO:10; the nucleotide sequence from position 380 to 420 in SEQ ID NO:10; or a sequence having at least 95% identity to any of said sequences.

In certain embodiments, the nucleic acid regulatory elements of the invention comprise or consist of a sequence selected from the group consisting of: the nucleotide sequence from position 33 to 310 in SEQ ID NO:1; the nucleotide sequence from position 47 to 450 in SEQ ID NO:5; the nucleotide sequence from position 10 to 420 in SEQ ID NO:10, or a sequence having at least 95% identity to any of said sequences.

In further embodiments, the invention provides a nucleic acid regulatory element for enhancing muscle-specific gene expression comprising, consisting essentially of, or consisting of a sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, or a sequence having at least 80%, preferably at least 85%, more preferably at least 90%, even more preferably at least 95%, such as 95%, 96%, 97%, 98%, or 99%, identity to any of these sequences.

In yet further embodiments, the invention provides for a nucleic acid regulatory element for enhancing cardiac and skeletal muscle-specific gene expression comprising a sequence selected from the group consisting of: SEQ ID NO:1, SEQ ID NO:2, SEQ ID NO:3, SEQ ID NO:4, SEQ ID NO:5, SEQ ID NO:6, or a sequence having at least 80%, preferably at least 85%, more preferably at least 90%, even more preferably at least 95%, such as 95%, 96%, 97%, 98%, or 99%, identity to any of these sequences.

In yet further embodiments, the invention provides for a nucleic acid regulatory element for enhancing skeletal muscle-specific gene expression comprising, consisting essentially of, or consisting of a sequence selected from the group consisting of: SEQ ID NO:7, SEQ ID NO:8, SEQ ID NO:9, SEQ ID NO:10, SEQ ID NO:11, SEQ ID NO:12, SEQ ID NO:13, or a sequence having at least 80%, preferably at least 85%, more preferably at least 90%, even more preferably at least 95%, such as 95%, 96%, 97%, 98%, or 99%, identity to any of these sequences.

In further embodiments, the nucleic acid regulatory elements for enhancing muscle-specific gene expression, comprise, consist essentially of, or consist of a sequence selected from the group consisting of: SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, a functional fragment thereof comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or SEQ ID NO:13, or a sequence having at least 80%, preferably at least 85%, more preferably at least 90%, even more preferably at least 95%, such as 95%, 96%, 97%, 98%, or 99%, identity to any of these sequences.

In further embodiments, the nucleic acid regulatory elements for enhancing cardiac and skeletal muscle-specific gene expression comprise, consist essentially of, or consist of a sequence selected from the group consisting of: SEQ ID NO:17, SEQ ID NO:18, SEQ ID NO:19, SEQ ID NO:20, SEQ ID NO:21, SEQ ID NO:22, a functional fragment thereof comprising SEQ ID NO:1, SEQ ID NO:2, SEQ ID NO:3, SEQ ID NO:4, SEQ ID NO:5, or SEQ ID NO:6, or a sequence having at least 80%, preferably at least 85%, more preferably at least 90%, even more preferably at least 95%, such as 95%, 96%, 97%, 98%, or 99%, identity to any of these sequences.

In further embodiments, the nucleic acid regulatory elements for enhancing skeletal muscle-specific gene expression comprise, consist essentially of, or consist of a sequence selected from the group consisting of: SEQ ID NO:23, SEQ ID NO:24, SEQ ID NO:25, SEQ ID NO:26, SEQ ID NO:27, SEQ ID NO:28, SEQ ID NO:29, a functional fragment thereof comprising SEQ ID NO:7, SEQ ID NO:8, SEQ ID NO:9, SEQ ID NO:10, SEQ ID NO:11, SEQ ID NO:12, or SEQ ID NO:13, or a sequence having at least 80%, preferably at least 85%, more preferably at least 90%, even more preferably at least 95%, such as 95%, 96%, 97%, 98%, or 99%, identity to any of these sequences.

It is also possible to make nucleic acid regulatory elements that comprise an artificial sequence by combining two or more identical or different sequences disclosed herein or functional fragments thereof. Accordingly, in certain embodiments a nucleic acid regulatory element for enhancing muscle-specific gene expression is provided comprising at least two sequences selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, a sequence having at least 90%, preferably at least 95%, such as 95%, 96%, 97%, 98%, or 99%, identity to any of these sequences, or a functional fragment thereof.

Also disclosed herein is a nucleic acid regulatory element for enhancing muscle-specific gene expression, in particular cardiac and skeletal muscle-specific gene expression, comprising at least two sequences selected from the group consisting of: SEQ ID NO:1, SEQ ID NO:2, SEQ ID NO:3, SEQ ID NO:4, SEQ ID NO:5, SEQ ID NO:6, a sequence having at least 90%, preferably at least 95%, such as 95%, 96%, 97%, 98%, or 99%, identity to any of these sequences, or a fragment thereof.

Also disclosed herein is a nucleic acid regulatory element for enhancing muscle-specific gene expression, in particular skeletal muscle-specific gene expression, comprising at least two sequences selected from the group consisting of: SEQ ID NO:7, SEQ ID NO:8, SEQ ID NO:9, SEQ ID NO:10, SEQ ID NO:11, SEQ ID NO:12, SEQ ID NO:13, a sequence having at least 90%, preferably at least 95%, such as 95%, 96%, 97%, 98%, or 99%, identity to any of these sequences, or a fragment thereof.

For example, disclosed herein is a nucleic acid regulatory element comprising, consisting essentially of, or consisting of SEQ ID NO:1 and SEQ ID NO:5; a nucleic acid regulatory element comprising, consisting essentially of, or consisting of SEQ ID NO:1 and SEQ ID NO:10; a nucleic acid regulatory element comprising, consisting essentially of, or consisting of SEQ ID NO:1, SEQ ID NO:5, and SEQ ID NO:10; a nucleic acid regulatory element comprising, consisting essentially of, or consisting of 2, 3, 4, or 5 repeats, e.g. tandem repeats, of SEQ ID NO:1; a nucleic acid regulatory element comprising, consisting essentially of, or consisting of 2, 3, 4, or 5 repeats, e.g. tandem repeats, of SEQ ID NO:5; or a nucleic acid regulatory element comprising, consisting essentially of, or consisting of 2, 3, 4, or 5 repeats, e.g. tandem repeats, of SEQ ID NO:10.

Particular examples of nucleic acid regulatory elements that comprise an artificial sequence include the regulatory elements that are obtained by rearranging the transcription factor binding sites (TFBS) that are present in the sequences disclosed herein. Said rearrangement may encompass changing the order of the TFBSs and/or changing the position of one or more TFBSs relative to the other TFBSs and/or changing the copy number of one or more of the TFBSs. For example, also disclosed herein is a nucleic acid regulatory element for enhancing muscle-specific gene expression, in particular cardiac and skeletal muscle-specific gene expression, comprising binding sites for E2A, HNH1, NF1, C/EBP, LRF, MyoD, and SREBP; or for E2A, NF1, p53, C/EBP, LRF, and SREBP; or for E2A, HNH1, HNF3a, HNF3b, NF1, C/EBP, LRF, MyoD, and SREBP; or E2A, HNF3a, NF1, C/EBP, LRF, MyoD, and SREBP; or for E2A, HNF3a, NF1, CEBP, LRF, MyoD, and SREBP; or for HNF4, NF1, RSRFC4, C/EBP, LRF, and MyoD, or NF1, PPAR, p53, C/EBP, LRF, and MyoD. For example, also disclosed herein is a nucleic acid regulatory element for enhancing muscle-specific gene expression, in particular skeletal muscle-specific gene expression, comprising binding sites for E2A, NF1, SRFC, p53, C/EBP, LRF, and MyoD; or for E2A, NF1, C/EBP, LRF, MyoD, and SREBP; or for E2A, HNF3a, C/EBP, LRF, MyoD, SEREBP, and Tall_b; or for E2A, SRF, p53, C/EBP, LRF, MyoD, and SREBP; or for HNF4, NF1, RSRFC4, C/EBP, LRF, and SREBP; or for E2A, HNF3a, HNF3b, NF1, SRF, C/EBP, LRF, MyoD, and SREBP; or for E2A, CEBP, and MyoD. In further examples, these nucleic acid regulatory elements comprise at least two, such as 2, 3, 4, or more copies of one or more of the recited TFBSs.

In case the regulatory element is provided as a single stranded nucleic acid, e.g. when using a single-stranded AAV vector, the complement strand is considered equivalent to the disclosed sequences. Hence, also disclosed herein is a nucleic acid regulatory element for enhancing muscle-specific gene expression comprising, consisting essentially of, or consisting of the complement of a sequence described herein, in particular a sequence selected from the group consisting of: SEQ ID NO:1, SEQ ID NO:2, SEQ ID NO:3, SEQ ID NO:4, SEQ ID NO:5, SEQ ID NO:6, SEQ ID NO: 7, SEQ ID NO: 8, SEQ ID NO: 9, SEQ ID NO: 10, SEQ ID NO: 11, SEQ ID NO: 12, SEQ ID NO: 13, a sequence having at least 80%, preferably at least 85%, more preferably at least 90%, even more preferably at least 95%, such as 95%, 96%, 97%, 98%, or 99%, identity to any of these sequences, or a functional fragment thereof.

Also disclosed herein is a nucleic acid regulatory element for enhancing muscle-specific gene expression hybridizing under stringent conditions to a nucleic acid regulatory element described herein, in particular to the nucleic acid regulatory element comprising, consisting essentially of, or consisting of a sequence selected from the group consisting of: SEQ ID NO:1, SEQ ID NO: 2, SEQ ID NO:3, SEQ ID NO:4, SEQ ID NO:5, SEQ ID NO:6, SEQ ID NO: 7, SEQ ID NO: 8, SEQ ID NO: 9, SEQ ID NO: 10, SEQ ID NO: 11, SEQ ID NO: 12, SEQ ID NO: 13, a sequence having at least 90%, preferably at least 95%, such as 95%, 96%, 97%, 98%, or 99%, identity to any of these sequences, a functional fragment thereof, or to its complement. Said nucleic acid regulatory elements do not need to be of equal length as the sequence they hybridize to. In preferred embodiments, the size of said hybridizing nucleic acid regulatory element does not differ more than 25% in length, in particular 20% in length, more in particular 15% in length, most in particular 10% in length from the sequence it hybridizes to.

The expression 'hybridize under stringent conditions', refers to the ability of a nucleic acid molecule to hybridize to a target nucleic acid molecule under defined conditions of temperature and salt concentration. Typically, stringent hybridization conditions are no more than 25° C. to 30° C. (for example, 20° C., 15° C., 10° C. or 5° C.) below the melting temperature (Tm) of the native duplex. Methods of calculating Tm are well known in the art. By way of non-limiting example, representative salt and temperature conditions for achieving stringent hybridization are: lx SSC, 0.5% SDS at 65° C. The abbreviation SSC refers to a buffer used in nucleic acid hybridization solutions. One liter of the 20× (twenty times concentrate) stock SSC buffer solution (pH 7.0) contains 175.3 g sodium chloride and 88.2 g sodium citrate. A representative time period for achieving hybridization is 12 hours.

Preferably the regulatory elements as described herein are fully functional while being only of limited length. This allows their use in vectors or nucleic acid expression cassettes without unduly restricting their payload capacity. Accordingly, in embodiments, the regulatory element disclosed herein is a nucleic acid of 1500 nucleotides or less, 1000 nucleotides or less, 900 nucleotides or less, 800 nucleotides or less, 700 nucleotides or less, more preferably 600 nucleotides or less, such as 550 nucleotides or less, 500 nucleotides or less, 450 nucleotides or less, 400 nucleotides or less, 350 nucleotides or less, or 300 nucleotides or less (i.e. the nucleic acid regulatory element has a maximal length of 1500 nucleotides, 1000 nucleotides, 900 nucleotides, 800 nucleotides, 700 nucleotides, preferably 600 nucleotides, such as 550 nucleotides, 500 nucleotides, 450 nucleotides, 400 nucleotides, 350 nucleotides, or 300 nucleotides).

However, it is to be understood that the disclosed nucleic acid regulatory elements retain regulatory activity (i.e. with regard to specificity and/or activity of transcription) and thus they particularly have a minimum length of 20 nucleotides, 25 nucleotides, 30 nucleotides, 35 nucleotides, 40 nucleotides, 45 nucleotides, 50 nucleotides, 100 nucleotides, 150 nucleotides, 200 nucleotides, 250 nucleotides, 300 nucleotides, 350 nucleotides or 400 nucleotides.

In certain embodiments, the invention provides for a nucleic acid regulatory element of 1000 nucleotides or less, preferably 600 nucleotides or less, such as 550 nucleotides or less, 500 nucleotides or less, 450 nucleotides or less, 400 nucleotides or less, 350 nucleotides or less, or 300 nucleotides or less, for enhancing muscle-specific gene expression comprising a sequence selected from the group consisting of: SEQ ID NO:1, SEQ ID NO: 2, SEQ ID NO:3, SEQ ID NO:4, SEQ ID NO:5, SEQ ID NO:6, SEQ ID NO: 7, SEQ ID NO: 8, SEQ ID NO: 9, SEQ ID NO: 10, SEQ ID NO: 11, SEQ ID NO: 12, SEQ ID NO: 13, a sequence having at least 80%, preferably at least 85%, more preferably at least 90%, even more preferably at least 95%, such as 95%, 96%, 97%, 98%, or 99%, identity to any of these sequences, or a functional fragment thereof.

The nucleic acid regulatory elements disclosed herein may be used in a nucleic acid expression cassette. Accordingly, in an aspect the invention provides for the use of the nucleic acid regulatory elements as described herein in a nucleic acid expression cassette.

In an aspect the invention provides a nucleic acid expression cassette comprising a nucleic acid regulatory element as described herein, operably linked to a promoter. In embodiments, the nucleic acid expression cassette does not contain a transgene. Such nucleic acid expression cassette may be used to drive expression of an endogenous gene. In preferred embodiments, the nucleic acid expression cassette comprises a nucleic acid regulatory element as described herein, operably linked to a promoter and a transgene.

As used herein, the term 'nucleic acid expression cassette' refers to nucleic acid molecules that include one or more transcriptional control elements (such as, but not limited to promoters, enhancers and/or regulatory elements, polyadenylation sequences, and introns) that direct (trans)gene expression in one or more desired cell types, tissues or organs. Typically, they will also contain a transgene, although it is also envisaged that a nucleic acid expression cassette directs expression of an endogenous gene in a cell into which the nucleic acid cassette is inserted.

The term 'operably linked' as used herein refers to the arrangement of various nucleic acid molecule elements relative to each such that the elements are functionally connected and are able to interact with each other. Such elements may include, without limitation, a promoter, an enhancer and/or a regulatory element, a polyadenylation sequence, one or more introns and/or exons, and a coding sequence of a gene of interest to be expressed (i.e., the transgene). The nucleic acid sequence elements, when properly oriented or operably linked, act together to modulate the activity of one another, and ultimately may affect the level of expression of the transgene. By modulate is meant increasing, decreasing, or maintaining the level of activity of a particular element. The position of each element relative to other elements may be expressed in terms of the 5' terminus and the 3' terminus of each element, and the distance between any particular elements may be referenced by the number of intervening nucleotides, or base pairs, between the elements. As understood by the skilled person, operably linked implies functional activity, and is not necessarily related to a natural positional link. Indeed, when used in nucleic acid expression cassettes, the regulatory elements will typically be located immediately upstream of the promoter (although this is generally the case, it should definitely not be interpreted as a limitation or exclusion of positions within the nucleic acid expression cassette), but this needs not be the case in vivo. E.g., a regulatory element sequence naturally occurring downstream of a gene whose transcription it affects is able to function in the same way when located upstream of the promoter. Hence, according to a specific embodiment, the regulatory or enhancing effect of the regulatory element is position-independent.

In particular embodiments, the nucleic acid expression cassette comprises one nucleic acid regulatory element as described herein. In alternative embodiments, the nucleic acid expression cassette comprises two or more, such as, e.g., 2, 3, 4, 5, 6, 7, 8, 9, or 10, nucleic acid regulatory elements as described herein, i.e. they are combined modularly to enhance their regulatory (and/or enhancing) effect. In further embodiments, at least two of the two or more nucleic acid regulatory elements are identical or substantially identical. In yet further embodiments, all of the two or more regulatory elements are identical or substantially identical. The copies of the identical or substantially identical nucleic acid regulatory elements may be provided as tandem repeats in the nucleic acid expression cassette. In alternative further embodiments, at least two of the two or more nucleic acid regulatory elements are different from each other. The nucleic acid expression cassette may also comprise a combination of identical and substantially identical nucleic acid regulatory elements and non-identical nucleic acid regulatory elements.

For example, the nucleic acid expression cassette may comprise a nucleic acid regulatory element comprising SEQ ID NO:1, and a nucleic acid regulatory element comprising SEQ ID NO:5; or the nucleic acid expression cassette may comprise a nucleic acid regulatory element comprising SEQ ID NO:1 and a nucleic acid regulatory element comprising SEQ ID NO:10; or the nucleic acid expression cassette may comprise a nucleic acid regulatory element comprising SEQ ID NO:1, a nucleic acid regulatory element comprising SEQ ID NO:5, and a nucleic acid regulatory element comprising SEQ ID NO:1; or the nucleic acid regulatory element may comprise 2, 3, 4, or 5 nucleic acid regulatory elements comprising SEQ ID NO:1; or the nucleic acid regulatory element may comprise 2, 3, 4, or 5 nucleic acid regulatory elements comprising SEQ ID NO:5; or the nucleic acid regulatory element may comprise 2, 3, 4, or 5 nucleic acid regulatory elements comprising SEQ ID NO:10.

As used in the application, the term 'promoter' refers to nucleic acid sequences that regulate, either directly or indirectly, the transcription of corresponding nucleic acid coding sequences to which they are operably linked (e.g. a transgene or endogenous gene). A promoter may function alone to regulate transcription or may act in concert with one or more other regulatory sequences (e.g. enhancers or silencers, or regulatory elements). In the context of the present application, a promoter is typically operably linked to a regulatory element as disclosed herein to regulate transcription of a (trans)gene. When a regulatory element as described herein is operably linked to both a promoter and a transgene, the regulatory element can (1) confer a significant degree of muscle-specific, in particular cardiac and skeletal muscle-specific or skeletal muscle-specific, expression in vivo (and/or in myoblasts, myocytes, or muscle-derived cell lines, in particular cardiac and skeletal or skeletal myoblasts, cardiac and skeletal or skeletal myocytes, or cardiac and skeletal muscle or skeletal muscle-derived cell lines in vitro) of the transgene, and/or (2) can increase the level of expression of the transgene in muscle, in particular cardiac and skeletal muscle or skeletal muscle (and/or in myoblasts, myocytes, or muscle-derived cell lines, in particular cardiac and skeletal or skeletal myoblasts, cardiac and skeletal or skeletal myocytes, or cardiac and skeletal muscle or skeletal muscle-derived cell lines in vitro).

The promoter may be homologous (i.e. from the same species as the animal, in particular mammal, to be transfected with the nucleic acid expression cassette) or heterologous (i.e. from a source other than the species of the animal, in particular mammal, to be transfected with the expression cassette). As such, the source of the promoter may be any virus, any unicellular prokaryotic or eukaryotic organism, any vertebrate or invertebrate organism, or any plant, or may even be a synthetic promoter (i.e. having a non-naturally occurring sequence), provided that the promoter is functional in combination with the regulatory elements described herein. In preferred embodiments, the promoter is a mammalian promoter, in particular a murine or human promoter.

The promoter may be an inducible or constitutive promoter.

The enrichment in muscle-specific TFBS in the nucleic acid regulatory elements disclosed herein in principle allows the regulatory elements to direct muscle-specific expression even from a promoter that itself is not muscle-specific. Hence, the regulatory elements disclosed herein can be used in nucleic acid expression cassettes in conjunction with their natural promoter, as well as with another promoter. Preferably, the nucleic acid expression cassettes disclosed herein comprise a muscle-specific promoter. This to increase muscle-specificity and/or avoid leakage of expression in other tissues. Non-limiting examples of muscle-specific promoters, include the desmin (DES) promoter, the alpha 2 actinin (ACTN2) promoter, the filamin-C (FLNC) promoter, the sarcoplasmic/endoplasmic reticulum calcium ATPase 1 (ATP2A1) promoter, the troponin I type 1 (TNNI1) promoter, the myosin-1 (MYH1) promoter, the phosphorylatable, fast skeletal muscle myosin light chain (MYLPF) promoter, the alpha-3 chain tropomyosin (TPM3) promoter, the ankyrin repeat domain-containing protein 2 (ANKRD2) promoter the myosin heavy-chain (MHC) promoter, the myosin light-chain (MLC) promoter, the muscle creatine kinase (MCK) promoter, synthetic muscle promoters as described in Li et al. (1999. Nat Biotechnol. 17:241-245), such as the SPc5-12 promoter, the muscle creatine kinase (MCK) promoter, the dMCK promoter and the tMCK promoter consisting of respectively, a double or triple tandem of the MCK enhancer to the MCK basal promoter as described in Wang et al. (2008. Gene Ther. 15:1489-1499).

In particularly preferred embodiments, the promoter is a mammalian muscle-specific promoter, in particular a murine or human muscle-specific promoter.

In preferred embodiments, the promoter is from the desmin gene, in particular the murine or human desmin gene, such as the promoter as defined in SEQ ID NO: 16. For example, the murine desmin promoter is commercially available as pDRIVE-mDesmin (Invivogen). The desmin promoter is expressed in both cardiac muscle and skeletal muscle.

In embodiments, the promoter is a skeletal muscle-specific promoter, in particular a muscle creatine kinase (MCK) promoter, more particularly the double MCK promoter or triple MCK promoter consisting of a double or triple tandem of MCK enhancer and MCK basal promoter as described in Wang et al. (2008. Gene Ther. 15:1489-1499).

Furthermore, the promoter does not need to be the promoter of the transgene in the nucleic acid expression cassette, although it is possible that the transgene is transcribed from its own promoter.

To minimize the length of the nucleic acid expression cassette, the regulatory elements may be linked to minimal promoters, or shortened versions of the promoters described herein. A 'minimal promoter' (also referred to as basal promoter or core promoter) as used herein is part of a full-size promoter still capable of driving expression, but lacking at least part of the sequence that contributes to regulating (e.g. tissue-specific) expression. This definition covers both promoters from which (tissue-specific) regulatory elements have been deleted—that are capable of driving expression of a gene but have lost their ability to express that gene in a tissue-specific fashion and promoters from which (tissue-specific) regulatory elements have been deleted that are capable of driving (possibly decreased) expression of a gene but have not necessarily lost their ability to express that gene in a tissue-specific fashion. Preferably, the promoter contained in the nucleic acid expression cassette disclosed herein is 1000 nucleotides or less in length, 900 nucleotides or less, 800 nucleotides or less, 700 nucleotides or less, 600 nucleotides or less, 500 nucleotides or less, 400 nucleotides or less, 300 nucleotides or less, or 250 nucleotides or less.

The term 'transgene' as used herein refers to particular nucleic acid sequences encoding a polypeptide or a portion of a polypeptide to be expressed in a cell into which the nucleic acid sequence is introduced. However, it is also possible that transgenes are expressed as RNA, typically to control (e.g. lower) the amount of a particular polypeptide in a cell into which the nucleic acid sequence is inserted. These RNA molecules include but are not limited to molecules that exert their function through RNA interference (shRNA, RNAi), micro-RNA regulation (miR) (which can be used to control expression of specific genes), catalytic RNA, antisense RNA, RNA aptamers, etc. How the nucleic acid sequence is introduced into a cell is not essential to the invention, it may for instance be through integration in the genome or as an episomal plasmid. Of note, expression of the transgene may be restricted to a subset of the cells into which the nucleic acid sequence is introduced. The term 'transgene' is meant to include (1) a nucleic acid sequence that is not naturally found in the cell (i.e., a heterologous nucleic acid sequence); (2) a nucleic acid sequence that is a mutant form of a nucleic acid sequence naturally found in the cell into which it has been introduced; (3) a nucleic acid sequence that serves to add additional copies of the same (i.e., homologous) or a similar nucleic acid sequence naturally occurring in the cell into which it has been introduced; or (4) a silent naturally occurring or homologous nucleic acid sequence whose expression is induced in the cell into which it has been introduced.

The transgene may be homologous or heterologous to the promoter (and/or to the animal, in particular mammal, in which it is introduced, e.g. in cases where the nucleic acid expression cassette is used for gene therapy).

The transgene may be a full length cDNA or genomic DNA sequence, or any fragment, subunit or mutant thereof that has at least some biological activity. In particular, the transgene may be a minigene, i.e. a gene sequence lacking part, most or all of its intronic sequences. The transgene thus optionally may contain intron sequences. Optionally, the transgene may be a hybrid nucleic acid sequence, i.e., one constructed from homologous and/or heterologous cDNA and/or genomic DNA fragments. By 'mutant form' is meant a nucleic acid sequence that contains one or more nucleotides that are different from the wild-type or naturally occurring sequence, i.e., the mutant nucleic acid sequence contains one or more nucleotide substitutions, deletions, and/or insertions. The nucleotide substitution, deletion, and/or insertion can give rise to a gene product (i.e. e., protein or nucleic acid) that is different in its amino acid/nucleic acid sequence from the wild type amino acid/nucleic acid sequence. Preparation of such mutants is well known in the art. In some cases, the transgene may also include a sequence encoding a leader peptide or signal sequence such that the transgene product will be secreted from the cell.

The transgene that may be contained in the nucleic acid expression cassettes described herein typically encodes a gene product such as RNA or a polypeptide (protein).

In embodiments, the transgene encodes a therapeutic protein. The therapeutic protein may be a secretable protein. Non-limiting examples of secretable proteins, in particular secretable therapeutic proteins, include clotting factors, such as factor VIII or factor IX, insulin, erythropoietin, lipoprotein lipase, antibodies or nanobodies, growth factors, cytokines, chemokines, plasma factors, etc. The therapeutic protein may also be a structural protein. Non-limiting examples of structural proteins, in particular structural therapeutic proteins, include dystrophin and sarcoglycans. In embodiments, the transgene comprises microdystrophin 1 (MD1) gene or follistatin (FST) gene.

In embodiments, the transgene encodes an immunogenic protein. Non-limiting examples of immunogenic proteins include epitopes and antigens derived from a pathogen.

As used herein, the term "immunogenic" refers to a substance or composition capable of eliciting an immune response.

Other sequences may be incorporated in the nucleic acid expression cassette disclosed herein as well, typically to further increase or stabilize the expression of the transgene product (e.g. introns and/or polyadenylation sequences).

Any intron can be utilized in the expression cassettes described herein. The term "intron" encompasses any portion of a whole intron that is large enough to be recognized and spliced by the nuclear splicing apparatus. Typically, short, functional, intron sequences are preferred in order to keep the size of the expression cassette as small as possible which facilitates the construction and manipulation of the expression cassette. In some embodiments, the intron is obtained from a gene that encodes the protein that is encoded by the coding sequence within the expression cassette. The intron can be located 5' to the coding sequence, 3' to the coding sequence, or within the coding sequence. An advantage of locating the intron 5' to the coding sequence is to minimize the chance of the intron interfering with the function of the polyadenylation signal. In embodiments, the nucleic acid expression cassette disclosed herein further comprises an intron. Non-limiting examples of suitable introns are Minute Virus of Mice (MVM) intron, beta-globin intron (betaIVS-II), factor IX (FIX) intron A, Simian virus 40 (SV40) small-t intron, and beta-actin intron.

Preferably, the intron is MVM intron.

Any polyadenylation signal that directs the synthesis of a polyA tail is useful in the expression cassettes described herein, examples of those are well known to one of skill in the art. Exemplary polyadenylation signals include, but are not limited to, polyA sequences derived from the Simian virus 40 (SV40) late gene, the bovine growth hormone (BGH) polyadenylation signal, the minimal rabbit β-globin (mRBG) gene, and the synthetic polyA s(SPA) site as described in Levitt et al. (1989, Genes Dev 3:1019-1025) (SEQ ID NO:46).

Preferably, the polyadenylation signal is derived from SV40 (i.e. SV40 pA).

In particular embodiments, the invention provides a nucleic acid expression cassette comprising a nucleic acid regulatory element consisting of SEQ ID NO:10 or a sequence having 95% identity to said sequence, operably linked to a promoter, preferably a promoter selected from the group consisting of the promoter from the desmin gene or the SPc5-12 promoter, and a transgene, preferably a transgene encoding a luciferase. In further embodiments, the nucleic acid expression cassette further comprises an MVM intron. In yet further embodiments the nucleic acid expression cassette further comprises a polyadenylation signal, preferably a polyadenylation signal derived from SV40.

In particular embodiments, the invention provides a nucleic acid expression cassette comprising a nucleic acid regulatory element consisting of SEQ ID NO:10 or a sequence having 95% identity to said sequence, operably linked to a promoter, preferably the promoter from the desmin gene, and a transgene, preferably a transgene encoding microdystrophin 1 or follistatin. In further embodiments, the nucleic acid expression cassette further comprises an MVM intron. In yet further embodiments, the nucleic acid expression cassette further comprises a polyadenylation signal, preferably wherein the polyadenylation signal has SEQ ID NO:46.

The nucleic acid regulatory element and the nucleic acid expression cassette disclosed herein may be used as such, or typically, they may be part of a nucleic acid vector. Accordingly, a further aspect relates to the use of a nucleic acid regulatory element as described herein or a nucleic acid expression cassette as described herein in a vector, in particular a nucleic acid vector.

In an aspect, the invention also provides a vector comprising a nucleic acid regulatory element as disclosed herein. In further embodiments, the vector comprises a nucleic acid expression cassette as disclosed herein.

The term 'vector' as used in the application refers to nucleic acid molecules, e.g. double-stranded DNA, which may have inserted into it another nucleic acid molecule (the insert nucleic acid molecule) such as, but not limited to, a cDNA molecule. The vector is used to transport the insert nucleic acid molecule into a suitable host cell. A vector may contain the necessary elements that permit transcribing the insert nucleic acid molecule, and, optionally, translating the transcript into a polypeptide. The insert nucleic acid molecule may be derived from the host cell, or may be derived from a different cell or organism. Once in the host cell, the vector can replicate independently of, or coincidental with, the host chromosomal DNA, and several copies of the vector and its inserted nucleic acid molecule may be generated. The vectors can be episomal vectors (i.e., that do not integrate into the genome of a host cell), or can be vectors that integrate into the host cell genome. The term 'vector' may thus also be defined as a gene delivery vehicle that facilitates gene transfer into a target cell. This definition includes both non-viral and viral vectors. Non-viral vectors include but are not limited to cationic lipids, liposomes, nanoparticles, PEG, PEI, plasmid vectors (e.g. pUC vectors, bluescript vectors (pBS) and pBR322 or derivatives thereof that are devoid of bacterial sequences (minicircles)) transposons-based vectors (e.g. PiggyBac (PB) vectors or Sleeping Beauty (SB) vectors), etc. Viral vectors are derived from viruses and include but are not limited to retroviral, lentiviral, adeno-associated viral, adenoviral, herpes viral, hepatitis viral vectors or the like. Typically, but not necessarily, viral vectors are replication-deficient as they have lost the ability to propagate in a given cell since viral genes essential for replication have been eliminated from the viral vector. However, some viral vectors can also be adapted to replicate specifically in a given cell, such as e.g. a cancer cell, and are typically used to trigger the (cancer) cell-specific (onco)lysis. Virosomes are a non-limiting example of a vector that comprises both viral and non-viral elements, in particular they combine liposomes with an inactivated HIV or influenza virus (Yamada et al., 2003). Another example encompasses viral vectors mixed with cationic lipids.

In preferred embodiments, the vector is a viral vector, such as a retroviral, lentiviral, adenoviral, or adeno-associated viral (AAV) vector, more preferably an AAV vector. AAV vectors are preferably used as self-complementary, double-stranded AAV vectors (scAAV) in order to overcome one of the limiting steps in AAV transduction (i.e. single-stranded to double-stranded AAV conversion) (McCarty, 2001, 2003; Nathwani et al, 2002, 2006, 2011; Wu et al., 2008), although the use of single-stranded AAV vectors (ssAAV) are also encompassed herein.

AAV serotype 9 (AAV9) is ideally suited to achieve efficient transduction in heart and skeletal muscle. Accordingly, in particularly preferred embodiments, the vector is an AAV9 vector, more particularly a self-complementary AAV9 vector (scAAV9).

In other embodiments, the vector is a non-viral vector, preferably a plasmid, a minicircle, or a transposon-based vector, such as a Sleeping Beauty(SB)-based vector or piggyBac(PB)-based vector.

In yet other embodiments, the vector comprises viral and non-viral elements.

In particular embodiments, the invention provides a vector comprising a nucleic acid expression cassette comprising a nucleic acid regulatory element element consisting of SEQ ID NO:10, a promoter, preferably the promoter from the desmin gene, an MVM intron, a transgene, preferably a transgene encoding microdystrophin 1, and a polyadenylation signal, preferably the polyadenylation signal having SEQ ID NO:46. In particular embodiments, said vector has SEQ ID NO: 44.

In particular embodiments, the invention provides a vector comprising a nucleic acid expression cassette comprising a nucleic acid regulatory element consisting of SEQ ID NO:10, a promoter, preferably the promoter from the desmin gene, an MVM intron, a transgene, preferably a transgene encoding follistatin, and a polyadenylation signal, preferably the polyadenylation signal having SEQ ID NO:46. In particular embodiments, said vector has SEQ ID NO: 45.

The nucleic acid expression cassettes and vectors disclosed herein may be used, for example, to express proteins that are normally expressed and utilized in muscle (i.e. structural proteins), or to express proteins that are expressed in muscle and that are then exported to the blood stream for transport to other portions of the body (i.e. secretable proteins). For example, the expression cassettes and vectors disclosed herein may be used to express a therapeutic amount of a gene product (such as a polypeptide, in particular a therapeutic protein, or RNA) for therapeutic purposes, in particular for gene therapy. Typically, the gene product is encoded by the transgene within the expression cassette or vector, although in principle it is also possible to increase expression of an endogenous gene for therapeutic purposes. In an alternative example, the expression cassettes and vectors disclosed herein may be used to express an immunological amount of a gene product (such as a polypeptide, in particular an immunogenic protein, or RNA) for vaccination purposes.

The nucleic acid expression cassettes and vectors as taught herein may be formulated in a pharmaceutical composition with a pharmaceutically acceptable excipient, i.e., one or more pharmaceutically acceptable carrier substances and/or additives, e.g., buffers, carriers, excipients, stabilisers, etc. The pharmaceutical composition may be provided in the form of a kit.

The term "pharmaceutically acceptable" as used herein is consistent with the art and means compatible with the other ingredients of the pharmaceutical composition and not deleterious to the recipient thereof.

Accordingly, a further aspect of the invention relates to a pharmaceutical composition comprising a nucleic acid expression cassette or a vector described herein.

The use of nucleic acid regulatory elements described herein for the manufacture of these pharmaceutical compositions is also disclosed herein.

In embodiments, the pharmaceutical composition may be a vaccine. The vaccine may further comprise one or more adjuvants for enhancing the immune response. Suitable adjuvants include, for example, but without limitation, saponin, mineral gels such as aluminium hydroxide, surface active substances such as lysolecithin, pluronic polyols, polyanions, peptides, oil or hydrocarbon emulsions, bacilli Calmette-Guerin (BCG), *Corynebacterium parvum*, and the synthetic adjuvant QS-21. Optionally, the vaccine may further comprise one or more immunostimulatory molecules. Non-limiting examples of immunostimulatory molecules include various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc.

In a further aspect, the invention relates to the nucleic acid regulatory elements, the nucleic acid expression cassettes, the vectors, or the pharmaceutical compositions described herein for use in medicine.

As used herein, the terms “treat” or “treatment” refer to both therapeutic treatment and prophylactic or preventative measures. Beneficial or desired clinical results include, but are not limited to, prevention of an undesired clinical state or disorder, reducing the incidence of a disorder, alleviation of symptoms associated with a disorder, diminishment of extent of a disorder, stabilized (i.e., not worsening) state of a disorder, delay or slowing of progression of a disorder, amelioration or palliation of the state of a disorder, remission (whether partial or total), whether detectable or undetectable, or combinations thereof. “Treatment” can also mean prolonging survival as compared to expected survival if not receiving treatment.

As used herein, the terms “therapeutic treatment” or “therapy” and the like, refer to treatments wherein the object is to bring a subjects body or an element thereof from an undesired physiological change or disorder to a desired state, such as a less severe or unpleasant state (e.g., amelioration or palliation), or back to its normal, healthy state (e.g., restoring the health, the physical integrity and the physical well-being of a subject), to keep it at said undesired physiological change or disorder (e.g., stabilization, or not worsening), or to prevent or slow down progression to a more severe or worse state compared to said undesired physiological change or disorder.

As used herein the terms “prevention”, “preventive treatment” or “prophylactic treatment” and the like encompass preventing the onset of a disease or disorder, including reducing the severity of a disease or disorder or symptoms associated therewith prior to affliction with said disease or disorder. Such prevention or reduction prior to affliction refers to administration of the nucleic acid regulatory elements, the nucleic acid expression cassettes, the vectors, or the pharmaceutical compositions described herein to a patient that is not at the time of administration afflicted with clear symptoms of the disease or disorder. “Preventing” also encompasses preventing the recurrence or relapse-prevention of a disease or disorder for instance after a period of improvement. In embodiments, the nucleic acid regulatory elements, the nucleic acid expression cassettes, the vectors, or the pharmaceutical compositions described herein may be for use in gene therapy, in particular muscle-directed gene therapy, more particularly heart and skeletal muscle-directed gene therapy or skeletal muscle-directed gene therapy.

Also disclosed herein is the use of the nucleic acid regulatory elements, the nucleic acid expression cassettes, the vectors, or the pharmaceutical compositions described herein for the manufacture of a medicament for gene therapy, in particular muscle-directed gene therapy, more particularly heart and skeletal muscle-directed gene therapy or skeletal muscle-directed gene therapy.

Also disclosed herein is a method for gene therapy, in particular muscle-directed gene therapy, more particularly heart and skeletal muscle-directed gene therapy or skeletal muscle-directed gene therapy, in a subject in need of said gene therapy comprising:

introducing in the subject, in particular in muscle of the subject, more particularly in heart muscle or skeletal muscle of the subject, a nucleic acid expression cassette, a vector or a pharmaceutical composition described herein, wherein the nucleic acid expression cassette, the vector or the pharmaceutical composition comprises a nucleic acid regulatory element described herein operably linked to a promoter and a transgene; and expressing a therapeutically effective amount of the transgene product in the subject, in particular in muscle of the subject, more particularly in heart and skeletal muscle or in skeletal muscle of the subject.

The transgene product may be a polypeptide, in particular a structural protein such as, e.g., dystrophin or a sarcoglycan, or a secretable protein such as, e.g., a clotting factor, e.g., factor IX or factor VIII, a cytokine, a growth factor, an antibody or nanobody, a chemokine, a plasma factor, insulin, erythropoietin, lipoprotein lipase. In particular embodiments, the transgene product is follistatin or microdystrophin, in particular microdystrophin 1. Alternatively, the transgene product may be RNA, such as siRNA.

Exemplary diseases and disorders that may benefit from gene therapy using the nucleic acid regulatory elements, the nucleic acid expression cassettes, the vectors, or the pharmaceutical compositions described herein include muscular dystrophy (e.g. Duchenne muscular dystrophy (DMD)/Becker muscular dystrophy (BMD)), myotonic dystrophy, neuromuscular disease, motor neuron diseases (MND), such as e.g. Charcot-Marie-Tooth disease (CMT), spinal muscular atrophy (SMA), and amyotrophic lateral sclerosis (ALS), Emery-Dreifuss muscular dystrophy, facioscapulohumeral muscular dystrophy (FSHD), congenital muscular dystrophies, congenital myopathies, limb girdle muscular dystrophy, metabolic myopathies, muscle inflammatory diseases, myasthenia, mitochondrial myopathies, anomalies of ionic channels, nuclear envelop diseases, cardiomyopathies, cardiac hypertrophy, heart failure, distal myopathies, cardiovascular diseases, hemophilia, including hemophilia A and B, and diabetes.

Gene therapy protocols have been extensively described in the art. These include, but are not limited to, intramuscular injection of plasmid (naked or in liposomes), hydrodynamic gene delivery in various tissues, including muscle, interstitial injection, instillation in airways, application to endothelium, intra-hepatic parenchyme, and intravenous or intra-arterial administration. Various devices have been developed for enhancing the availability of DNA to the target cell. A simple approach is to contact the target cell physically with catheters or implantable materials containing DNA. Another approach is to utilize needle-free, jet injection devices which project a column of liquid directly into the target tissue under high pressure. These delivery paradigms can also be used to deliver vectors. Another approach to targeted gene delivery is the use of molecular conjugates, which consist of protein or synthetic ligands to which a nucleic acid-or DNA-binding agent has been attached for the specific targeting of nucleic acids to cells (Cristiano et al., 1993). In embodiments, the nucleic acid regulatory elements, the nucleic acid expression cassettes, the vectors, or the pharmaceutical compositions described herein may be for use as a vaccine, more particularly for use as a prophylactic vaccine.

Also disclosed herein is the use of the nucleic acid regulatory elements, the nucleic acid expression cassettes, the vectors, or the pharmaceutical compositions described herein for the manufacture of a vaccine, in particular for the manufacture of a prophylactic vaccine.

Also disclosed herein is a method of vaccination, in particular prophylactic vaccination, of a subject in need of said vaccination comprising:

introducing in the subject, in particular in muscle of the subject, more particularly in heart muscle or skeletal muscle of the subject, a nucleic acid expression cassette, a vector or a pharmaceutical composition described herein, wherein the nucleic acid expression cassette, the vector or the pharmaceutical composition comprises a nucleic acid regulatory element described herein operably linked to a promoter and a transgene; and expressing an immunologically effective amount of the transgene product in the subject, in particular in muscle of the subject, more particularly in heart and skeletal muscle or in skeletal muscle of the subject.

As used herein, a phrase such as "a subject in need of treatment" includes subjects that would benefit from treatment of a recited disease or disorder. Such subjects may include, without limitation, those that have been diagnosed with said disease or disorder, those prone to contract or develop said disease or disorder and/or those in whom said disease or disorder is to be prevented.

The terms "subject" and "patient" are used interchangeably herein and refer to animals, preferably vertebrates, more preferably mammals, and specifically include human patients and non-human mammals. "Mammalian" subjects include, but are not limited to, humans, domestic animals, commercial animals, farm animals, zoo animals, sport animals, pet and experimental animals such as dogs, cats, guinea pigs, rabbits, rats, mice, horses, cattle, cows; primates such as apes, monkeys, orang-utans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. Preferred patients or subjects are human subjects.

A 'therapeutic amount' or 'therapeutically effective amount' as used herein refers to the amount of gene product effective to treat a disease or disorder in a subject, i.e., to obtain a desired local or systemic effect. The term thus refers to the quantity of gene product that elicits the biological or medicinal response in a tissue, system, animal, or human that is being sought by a researcher, veterinarian, medical doctor or other clinician. Such amount will typically depend on the gene product and the severity of the disease, but can be decided by the skilled person, possibly through routine experimentation.

An "immunologically effective amount" as used herein refers to the amount of (trans)gene product effective to enhance the immune response of a subject against a subsequent exposure to the immunogen encoded by the (trans) gene. Levels of induced immunity can be determined, e.g. by measuring amounts of neutralizing secretory and/or serum antibodies, e.g., by plaque neutralization, complement fixation, enzyme-linked immunosorbent, or microneutralization assay.

Typically, the amount of (trans)gene product expressed when using an expression cassette or vector as described herein (i.e., with at least one muscle-specific nucleic acid regulatory element) are higher than when an identical expression cassette or vector is used but without a nucleic acid regulatory element therein. More particularly, the expression is at least double as high, at least five times as high, at least ten times as high, at least 20 times as high, at least 30 times as high, at least 40 times as high, at least 50 times as high, or even at least 60 times as high as when compared to the same nucleic acid expression cassette or vector without nucleic acid regulatory element. Moreover, the higher expression remains specific to muscle, in particular both heart and skeletal muscle or skeletal muscle alone. Furthermore, the expression cassettes and vectors described herein direct the expression of a therapeutic amount of the gene product for an extended period. Typically, therapeutic expression is envisaged to last at least 20 days, at least 50 days, at least 100 days, at least 200 days, and in some instances 300 days or more. Expression of the gene product (e.g. polypeptide) can be measured by any art-recognized means, such as by antibody-based assays, e.g. a Western Blot or an ELISA assay, for instance to evaluate whether therapeutic expression of the gene product is achieved. Expression of the gene product may also be measured in a bioassay that detects an enzymatic or biological activity of the gene product. Also disclosed herein is the use of the nucleic acid regulatory elements, the nucleic acid expression cassettes, or the vectors disclosed herein for transfecting or transducing muscle cells, preferably heart muscle cells and/ or skeletal muscle cells.

Further disclosed herein is the use of the nucleic acid expression cassettes or the vectors disclosed herein for expressing a transgene product in muscle cells, preferably heart muscle cells and/or skeletal muscle cells, wherein the nucleic acid expression cassette or the vector comprises a nucleic acid regulatory element disclosed herein operably linked to a promoter and a transgene.

Further disclosed herein is a method for expressing a transgene product in muscle cells, preferably heart muscle cells and/or skeletal muscle cells, comprising:

transfecting or transducing the muscle cells with a nucleic acid expression cassette or a vector disclosed herein, wherein the nucleic acid expression cassette or the vector comprises a nucleic acid regulatory element disclosed herein operably linked to a promoter and a transgene; and expressing the transgene product in the muscle cells.

Non-viral transfection or viral vector-mediated transduction of muscle cells may be performed by in vitro, ex vivo or in vivo procedures. The in vitro approach requires the in vitro transfection or transduction of muscle cells, e.g. muscle cells previously harvested from a subject, muscle cell lines or muscle cells differentiated from e.g. induced pluripotent stem cells or embryonic cells. The ex vivo approach requires harvesting of the muscle cells from a subject, in vitro transfection or transduction, and optionally re-introduction of the transfected muscle cells into the subject. The in vivo approach requires the administration of the nucleic acid expression cassette or the vector disclosed herein into a subject. In preferred embodiments, the transfection of the muscle cells is performed in vitro or ex vivo.

It is understood by the skilled person that the use of the nucleic acid regulatory elements, the nucleic acid expression cassettes and vectors disclosed herein has implications beyond gene therapy, e.g. coaxed differentiation of stem cells into myogenic cells, transgenic models for over-expression of proteins in muscle, etc.

The invention is further explained by the following non-limiting examples

EXAMPLES

Example 1

Identification of Cardiac and Skeletal Muscle-Specific Regulatory Elements

Experimental Procedures

Genes highly expressed both in heart and muscle, but showing only minimal expression in other tissues, were identified using the Specificity Measure (SPM) method described in Xiao et al. (2010. Bioinformatics 26:1273-1275). As data set we used the U133A/GNF1H Gene Atlas (GSE1133) of the human protein-encoding transcriptomes (Su et al. 2004. Proc. Natl. Acad. Sci. USA 101:6062-6067). This resulted in a short list of 5 genes: filamin-c gene (FLNC), actinin, alpha 2 gene (ACTN2), myosin regulatory light chain 2, ventricular/cardiac muscle isoform gene (MYL2), desmin gene (DES) and telethonin gene (TCAP). Next, the genomic context of these genes was searched for cross-species conserved regions enriched for transcription factor binding sites (TFBS) associated with high expression in muscle and heart. Additional filtering was done by selecting the putative nucleic acid regulatory elements that either overlapped or contained regions bearing reproducible biochemical features associated with transcription regulation and/or a open chromatin structure as defined in the ENCODE project (The ENCODE Project Consortium. 2012. Nature 489:57-74).

For the heart-specific regulatory elements we used a high-density gene expression database of 18,927 unique genes based on microarrays that were derived from 158 normal human samples from 19 different organs of 30 different individuals (Son, S. et al. 2005. Database of mRNA gene expression profiles of multiple human organs. Genome Res. 15:443-450). This was used to identify a set of most highly expressed (i.e. 'over-expressed') genes in the heart compared to any of the other tissues. A two-tailed t-test was used for each pairwise comparison. Conversely, a set of 'under-expressed' genes was identified, corresponding to those genes that exhibited the lowest expression in these respective organs compared to any of the other tissues. This analysis resulted in a set of 43 over-expressed genes and a collection of 37 under-expressed heart-specific genes. Next, the Reference Sequence (RefSeq) identifiers (IDs) lists of these 'over-expressed' and 'under-expressed' heart-specific genes were used to extract the corresponding promoter sequences upstream the reported transcription start sites (TSSs) by 1000 bases (NCBI36/hg18 genome assembly), using the transcription start location data stored in the refGene table of the UCSC Genome Browser (http://genome.ucsc.edu) database.

This resulted in two sets of heart-specific promoter sequences corresponding to promoters of 'over-expressed' or 'under-expressed' genes. In order to make a non-redundant set of representative promoter sequences, the promoter sequences were filtered using 'uclust' (http://www.drive5.com/usearch/).

The two sets of non-redundant tissue-specific promoter sequences corresponding to promoters of 'over-expressed' or 'under-expressed' genes were used as input for the DDM/MDS method, described in detail in De Bleser et al. (2007. Genome Biol 8:R83), which is specifically incorporated by reference herein. The observed differential behaviour might be explained by the presence of one or more TFBS elements characteristic of the promoters of the up-regulated or down-regulated group of genes. These 'differential' TFBS elements could be found using following procedure. First, a library of TFBS positional weight matrices (PWMs) (TRANSFAC® 2010.3) was used to predict TFBS on every promoter sequence. For the muscle-specific promoters we used the Find Individual Motif Occurences (fimo) application with a P-value cut-off of $10^{-3}$. The number of predicted TFBS elements per PWM per promoter was collected in the form of a matrix in which each row corresponds to a promoter sequence, while the columns corresponded to the used PWM. Two TFBS were considered correlated if their corresponding columns in the matrix were similar what could be measured using a distance function. With this approach, distance matrices summarizing all TFBS associations were constructed for the TFBS in both sets of promoters. Finally, by calculating the distance difference matrix (DDM) and performing multidimensional scaling on this DDM to visualize its content in two dimensions, TFBS could be distinguished that did not contribute to the observed differential gene expression as they were mapped near the origin of the DDM-MDS plot from 'deviating' TFBS that are likely responsible for the observed differential gene expression. As the MDS procedure plots TFBS that are strongly associated closer together than less associated ones, it was able to highlight interactions between TFBS in the promoter datasets. This procedure resulted in a list of TFBS associated with high tissue-specific expression for heart-specific promoters.

For the muscle-specific regulatory elements, a list of muscle-specific genes was extracted from the Tissue-specific Gene Expression and Regulation (TiGER) database. This was used to identify a set of the most highly expressed (i.e. 'over-expressed') genes in muscle tissue. Conversely, a set of 'under-expressed' genes was identified, corresponding to those genes that exhibited the lowest expression in muscle. Next, the Reference Sequence (RefSeq) identifiers (IDs) lists of these 'over-expressed' and 'under-expressed' muscle-specific genes were used to extract the corresponding promoter sequences upstream the reported transcription start sites (TSSs) by 1000 bases (NCBI36/hg18 genome assembly), using the transcription start location data stored in the refGene table of the UCSC Genome Browser (http://genome.ucsc.edu) database. This resulted in two sets of muscle-specific promoter sequences corresponding to promoters of 'over-expressed' or 'under-expressed' genes. In order to make a non-redundant set of representative promoter sequences, the promoter sequences were filtered using 'uclust' (http://www.drive5.com/usearch/).

The two sets of non-redundant tissue-specific promoter sequences corresponding to promoters of 'over-expressed' or 'under-expressed' genes were used as input for the DDM/MDS method, described in detail in De Bleser et al. (2007. Genome Biol 8:R83), which is specifically incorporated by reference herein. The observed differential behaviour might be explained by the presence of one or more TFBS elements characteristic of the promoters of the up-regulated or down-regulated group of genes. These 'differential' TFBS elements could be found using following procedure. First, a library of TFBS positional weight matrices (PWMs) (TRANSFAC® 2010.3) was used to predict TFBS on every promoter sequence. For the muscle-specific promoters we used the Find Individual Motif Occurences (fimo) application with a P-value cut-off of $10^{-3}$. The number of predicted TFBS elements per PWM per promoter was collected in the form of a matrix in which each row corresponds to a promoter sequence, while the columns corresponded to the used PWM. Two TFBS were considered correlated if their corresponding columns in the matrix were similar what could be measured using a distance function. With this approach, distance matrices summarizing all TFBS associations were constructed for the TFBS in both sets of promoters. Finally, by calculating the distance difference matrix (DDM) and performing multidimensional scaling on this DDM to visualize its content in two dimensions, TFBS could be distinguished that did not contribute to the observed differential gene expression as they were mapped near the origin of the DDM-MDS plot from 'deviating' TFBS that are likely responsible for the observed differential gene expression. As the MDS procedure plots TFBS that are strongly associated closer together than less associated ones, it was able to highlight interactions between TFBS in the promoter datasets. This procedure resulted in a list of TFBS associated with high tissue-specific expression for muscle-specific promoters.

Results

This computational approach led to the identification of 6 cardiac and skeletal muscle-specific regulatory sequences, summarized in Table 1.

TABLE 1

Cardiac and skeletal muscle-specific regulatory elements.

| Sequence | Name | Gene regulated by sequence | Size (bp) | Conserved TFBS present |
|---|---|---|---|---|
| SEQ ID NO: 1 | CSk-SH1 | Des | 381 | E2A, HNH1, NF1, CEBP, LRF, MyoD, SREBP |
| SEQ ID NO: 2 | CSk-SH2 | Des | 435 | E2A, NF1, p53, CEBP, LRF, SREBP |
| SEQ ID NO: 3 | CSk-SH3 | ACTN2 | 551 | E2A, HNH1, HNF3a, HNF3b, NF1, CEBP, LRF, MyoD, SREBP |
| SEQ ID NO: 4 | CSk-SH4 | ACTN2 | 430 | E2A, HNF3a, NF1, CEBP, LRF, MyoD, SREBP |
| SEQ ID NO: 5 | CSk-SH5 | FLNC | 454 | HNF4, NF1, RSRFC4, CEBP, LRF, MyoD |
| SEQ ID NO: 6 | CSk-SH6 | FLNC | 453 | NF1, PPAR, p53, CEBP, LRF, MyoD |

Bp: base pairs.

Example 2

In Vivo Validation of Cardiac and Skeletal Muscle-Specific Regulatory Elements Via AAV Vectors Experimental Procedures Generation of the AAV Plasmid Constructs (pAAV-CSk-SH-Des-Luc2)

Figure 3:
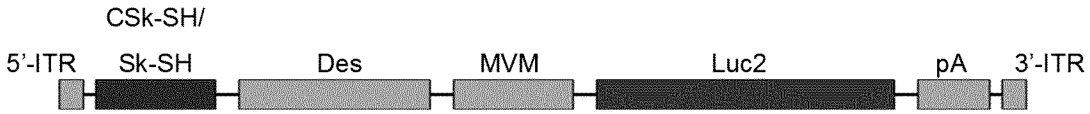
FIG. 3 shows a schematic representation of the AAV9sc-CSk-SH/Sk-SH-Des-Luc2 vectors disclosed herein. The expression cassette was packaged in a self-complementary (sc) adeno-associated virus, serotype 9 (AAV9). The cardiac and skeletal muscle-specific desmin (Des) promoter regulates transcription of the luciferase (Luc2) transgene. The identified cardiac and skeletal muscle-specific (CSk-SH) or muscle-specific (Sk-SH) nucleic acid regulatory elements were cloned upstream of the Des promoter. The expression cassette further comprises the Minute Virus of Mouse (MVM) intron and a Simian virus 40 (SV40) polyadenylation signal (pA). The expression cassette is flanked by inverted terminal repeats (ITR) from adeno-associated virus, serotype 2 (AAV2).

The cardiac and skeletal muscle-specific regulatory elements (CSk-SH1 to CSk-SH6) were synthesized by conventional oligonucleotide synthesis and flanked with Acc651 and MluI restriction sites. The different CSk-SHs were cloned upstream of the Desmin (Des) promoter that drives expression of a Firefly Luciferase (Luc2) reporter gene in the context of an adeno-associated viral vector (AAV) backbone (designated as pAAV-Des-Luc2), schematically represented in FIG. 3. The corresponding AAV plasmid constructs were designated as pAAV-CSk-SH-Des-Luc2. The plasmids also contained a Minute Virus of Mouse (MVM) intron and a Simian Virus 40 (SV40) polyadenylation site (pA).

AAV Vector Production (AAV9sc.CSk-SH1-6.Des.Luc2) and Purification

AAV9 vectors were produced by calcium phosphate (Invitrogen Corp, Carlsbad, Calif.) co-transfection of 293T human embryonic kidney cells with the pAAV plasmid of interest, an adenoviral helper plasmid and a chimeric packaging construct that delivers the AAV2 rep gene together with the AAV9 cap gene, as described in Vandendriessche et al. (2007. J Thromb Haemost 5:16-24), which is specifically incorporated by reference herein.

Briefly, two days post transfection, cells were harvested and vector particles were purified using isopycnic centrifugation methods. Harvested cells were lysed by successive freeze/thaw cycles and sonication, treated with benzonase (Novagen, Madison, Wis.) and deoxycholic acid (Sigma-Aldrich, St. Louis, Mo.) and subsequently subjected to 3 successive rounds of cesium chloride (Invitrogen Corp, Carlsbad, Calif.) density gradient ultracentrifugation. Fractions containing the AAV vector were collected, concentrated in 1 mM $MgCl_2$ in Dulbecco's phosphate buffered saline (PBS) (Gibco, BRL) and stored at −80° C.

Vector titers (in viral genomes (vg)/ml) were determined by quantitative real-time PCR using SYBR Green mix (which included SYBR Green dye, Taqman polymerase, ROX and dNTP's all in one) and luciferase specific primers on an ABI 7500 Real-Time PCR System (Applied Biosystem, Foster city, CA, USA). The forward and reverse primers used were 5'-CCCACCGTCGTATTCGTGAG-3' (SEQ ID NO: 14) and 5'-TCAGGGCGATGGTTTTGTCCC-3' (SEQ ID NO: 15), respectively.

Typically, for all vectors titers in the range of $1.5\text{-}6.1\times10^{11}$ vg/ml were achieved from a small production batch of 20 petri dishes of producer cells. If higher number of petri dishes such as 60 dishes of producer cells were used, a higher titer typically in the range of $10^{12}\text{-}10^{13}$ gc/ml of AAV particles were achieved. Known copy numbers ($10^2\text{-}10^7$) of the respective vector plasmids used to generate the corresponding AAV vectors, carrying the appropriate cDNAs were used to generate the standard curves.

Animal Studies

All animal procedures were approved by the institutional animal ethics committee of the Free University of Brussels (VUB) (Brussels, Belgium). All mice were housed under specific pathogen-free conditions; food and water were provided ad libitum.

Two-days old CB.17/IcrTac/Prkdcscid mice were intravenously injected into the periorbital vein with 50 μl of concentrated vectors ($5\times10^9$ vg/mouse) containing the different CSk-SH (i.e. CSk-SH1 to CSk-SH6) regulatory elements or AAV9-Des-Luc2 control vector ($5\times10^9$ vg/mouse) as summarized in Table 2.

TABLE 2

| Experimental design for the injection of cardiac and skeletal muscle-specific regulatory elements. Vector | Mouse number (n) | Dose | Titre (gc/ml) | Volume vector (μl) | Volume PBS (μl) | Total volume (μl) |
|---|---|---|---|---|---|---|
| AAV9sc.Des.Luc2 | 3 | $5\times10^9$ | $5.7\times10^{11}$ | 8.7 | 41.3 | 50 |
| AAV9sc.CSk-SH1.Des.Luc2 | 4 | $5\times10^9$ | $6.1\times10^{11}$ | 8.2 | 41.8 | 50 |
| AAV9sc.CSk-SH2.Des.Luc2 | 2 | $5\times10^9$ | $6.0\times10^{11}$ | 8.3 | 41.7 | 50 |
| AAV9sc.CSk-SH3.Des.Luc2 | 5 | $5\times10^9$ | $1.5\times10^{11}$ | 33.3 | 16.7 | 50 |
| AAV9sc.CSk-SH4.Des.Luc2 | 3 | $5\times10^9$ | $5.2\times10^{11}$ | 9.6 | 40.4 | 50 |

TABLE 2-continued

| Experimental design for the injection of cardiac and skeletal muscle-specific regulatory elements. Vector | Mouse number (n) | Dose | Titre (gc/ml) | Volume vector (μl) | Volume PBS (μl) | Total volume (μl) |
|---|---|---|---|---|---|---|
| AAV9sc.CSk-SH5.Des.Luc2 | 4 | $5 \times 10^9$ | $1.7 \times 10^{11}$ | 39.4 | 20.6 | 50 |
| AAV9sc.CSk-SH6.Des.Luc2 | 4 | $5 \times 10^9$ | $3.1 \times 10^{11}$ | 16.1 | 33.9 | 50 |

Mice were imaged between 5 and 8 weeks post-injection once per week using a biospace In Vivo photo Imaging System (IVIS). The CCD was cooled to −120° C. and the field of view (FOV) set at 25 cm height of the sample shelf. The charged coupled device (CCD) camera operates by converting photons that strike the CCD pixel into electrons at wavelengths between 400-100 nm, allowing detection of visible imaged infrared light through by anesthetizing with 2% isofluorane and oxygen. D-luciferin substrate was injected intravenously, at a dose of 150 μg/g of body weight. Mice were euthanized 9 weeks post injection and intact organs were harvested and imaged using a biospace In Vivo photo Imaging System (IVIS).

mRNA Analysis

Total RNA was extracted from different organs of the mice by a silica-membrane based purification kit according to the manufacturer's instructions (Invitrogen Corp, Carlsbad, Calif., USA). Subsequently, 50 ng of total RNA from each sample was subjected to reverse transcription (RT) using a cDNA synthesis kit (Invitrogen Corp, Carlsbad, Calif., USA). Next, a cDNA amount corresponding to 10 ng of total RNA was amplified by quantitative(q) PCR on an ABI 7700 (Applied Biosystems, Foster City, Calif., USA), using 5'-CCCACCGTCGTATTCGTGAG-3' (SEQ ID NO: 14) as a forward primer and 5'-TCAGGGC-GATGGTTTTGTCCC-3' (SEQ ID NO: 15) as reverse primer (amplicon 217 bp). The qPCR standards consisted of serially diluted AAV9-CSk-SH-Des-Luc2 plasmids of known quantity. The Luc2 mRNA levels were normalized to mRNA levels of the endogenous murine glyceraldehyde-3-phosphate dehydrogenase (mGAPDH) gene, using 5'-TGTGTCCGTCGTGGATCTGA-3' (SEQ ID NO:31) as forward primer and 5'-GCCTGCTTCACCACCTTCTTGA-3' (SEQ ID NO:32) as the reverse primer (amplicon 82 bp). RNA samples were amplified with and without reverse transcriptase to exclude DNA amplification. The size of the amplified PCR fragments was verified on a 1.8% agarose gel.

Transduction Efficiency and Vector Biodistribution

Transduction efficiency of the viral vectors and biodistribution were evaluated by quantifying Luc2 transgene copy numbers in the different organs and tissues as described previously (Pacak, C. A., et al. 2008. Genet Vaccines Ther 6: 13). Briefly, genomic DNA was extracted from 30 mg of each tissue according to DNeasy Blood & Tissue Kit protocol (Qiagen, Chatsworth, Calif., USA) and 100 ng of genomic DNA from each sample was subjected to qPCR, using the Luc2-specific forward primer 5'-CC-CACCGTCGTATTCGTGAG-3' (SEQ ID NO: 14) and reverse primer 5'-TCAGGGCGATGGTTTTGTCCC-3' (SEQ ID NO: 15) (amplicon 217 bp). Known copy numbers ($10^2$-$10^7$) of the corresponding plasmid pAAV-CSk-SH-Des-Luc2 were used to generate the standard curve. The results were expressed as mean AAV copy number/100 ng of genomic DNA.

Results

To assess the effect of the in silico identified cardiac and skeletal muscle-specific regulatory elements (CSk-SH) in vivo, adeno-associated vectors were generated that expressed the luciferase gene luc2 from a chimeric promoter. This promoter was composed of the muscle-specific desmin (Des) promoter linked to the cardiac and skeletal muscle-specific regulatory elements CSk-SH1-6. The vectors were intravenously injected in mice and whole body images were taken from the mice at 5 and 6 weeks post-injection to examine luciferase expression level.

All mice injected with a vector comprising a cardiac and skeletal muscle-specific regulatory element (CSk-SH1-6) showed increased luciferase activity compared to control mice that were injected with a corresponding AAV9 vector without a regulatory element, indicating that all of the regulatory elements tested increased luciferase expression (data not shown). We observed very robust and enhanced luciferase activity in mice that were injected with AAV9 vector comprising the regulatory element CSk-SH1, CSk-SH3 or CSk-SH5 at 5 and 6 weeks post-injection as compared to luciferase activity of the control mice.

Figure 4A:
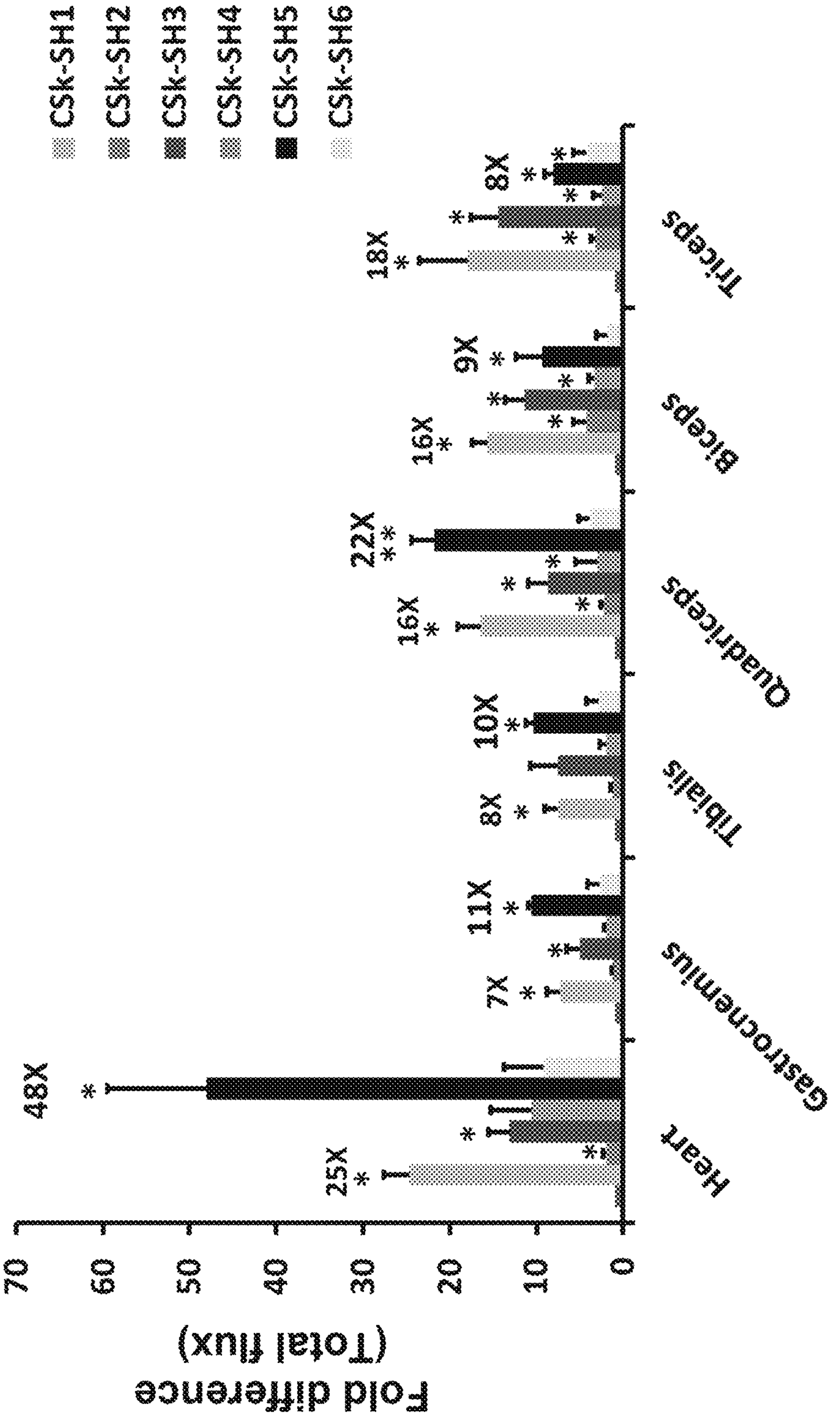
FIG. 4: Difference in luciferase expression (A) and Luc mRNA level (B) in heart and muscle tissue of mice that were intravenously injected with, from left to right, AAV9sc-CSk-SH1-Des-Luc2 (CSk-SH1), AAV9sc-CSk-SH2-Des-Luc2 (CSk-SH2), AAV9sc-CSk-SH3-Des-Luc2 (CSk-SH3), AAV9sc-CSk-SH4-Des-Luc2 (CSk-SH4), AAV9sc-CSk-SH5-Des-Luc2 (CSk-SH5), or AAV9sc-CSk-SH6-Des-Luc2 (CSk-SH6) vector compared to mice that were injected with the control vector AAV9sc-Des-Luc2 without nucleic acid regulatory element (control, no Csk-SH). Luciferase expression was measured as total flux, expressed in photons per second per centimetre squared per steradian (photons/sec/$cm^2$/sr), released by luciferase activity in the selected tissues at 9 weeks post-injection. Results were presented as mean±standard error of the mean, *$p<0.05$; **$p<0.001$. Luc mRNA levels were measured by a quantitative RT-PCR method (qRT-PCR) at the end of the experiment from total RNA extracted from biopsies from the indicated tissues. Results were presented as mean±standard error of the mean, *$p<0.05$; **$p<0.001$.
Figure 4B:
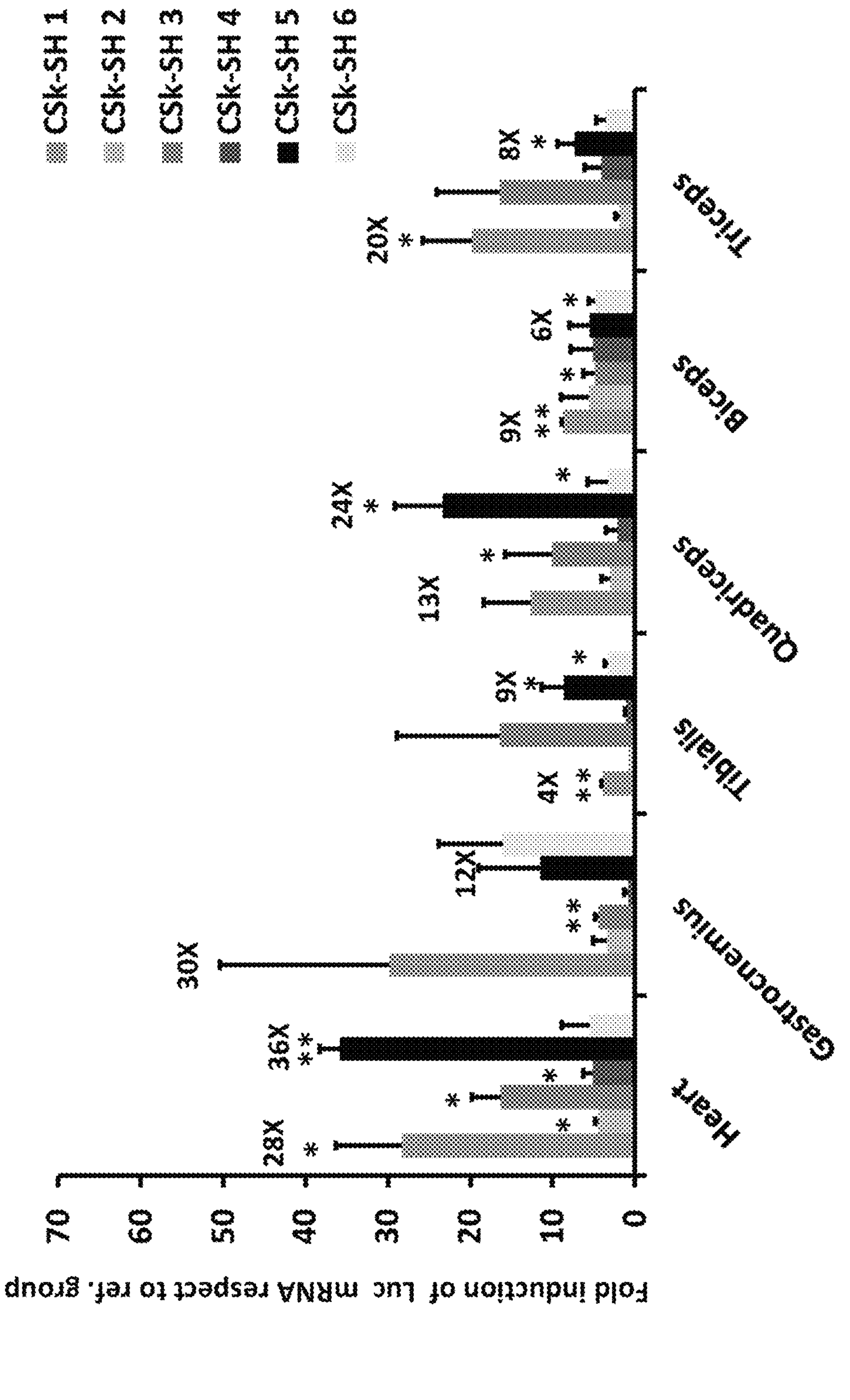
Figure 5A:
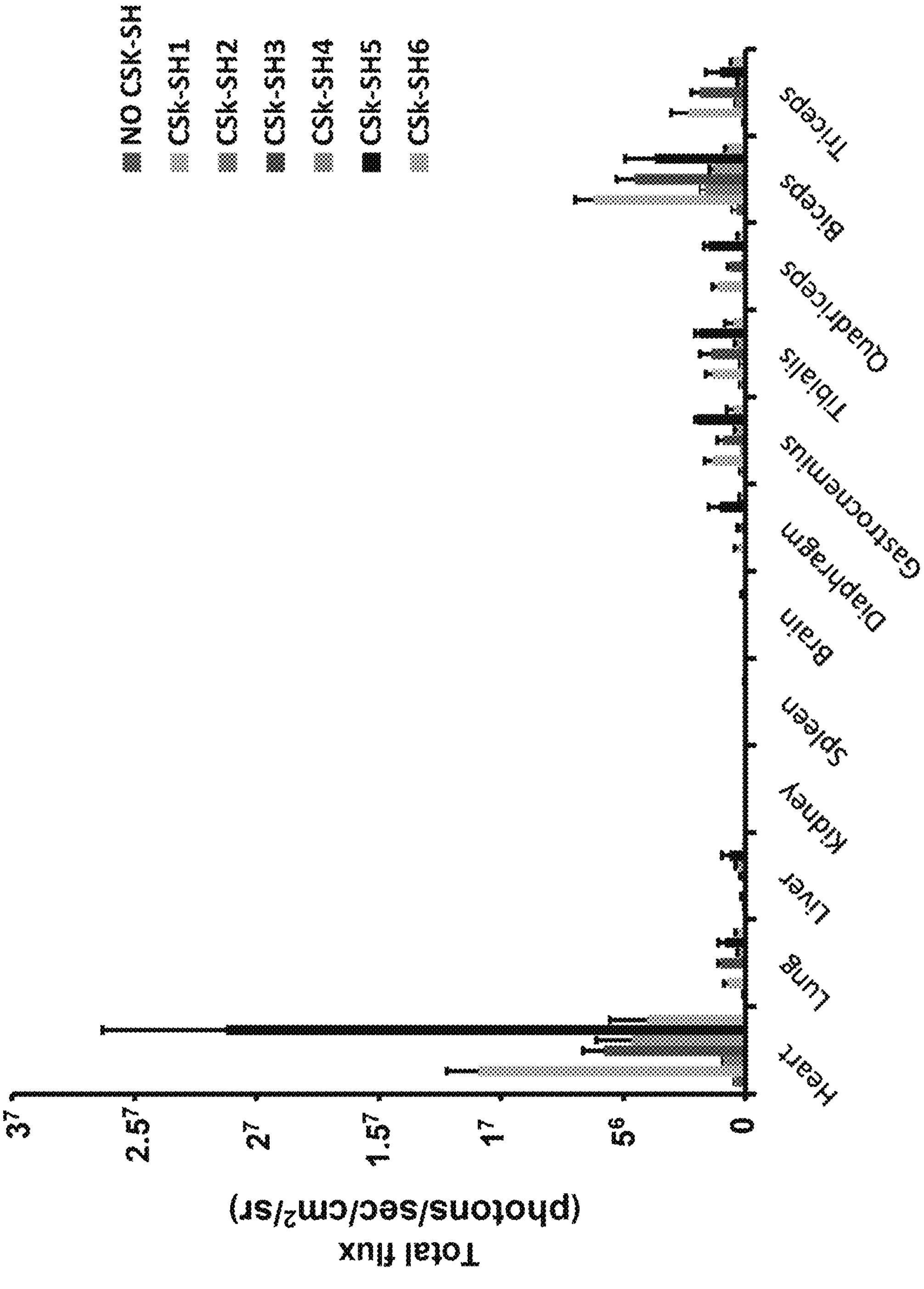
FIG. 5: (A) Luciferase expression in selected tissues of mice that were intravenously injected with, from left to right, AAV9sc-Des-Luc2 (control, no CSk-SH), AAV9sc-CSk-SH1-Des-Luc2 (CSk-SH1), AAV9sc-CSk-SH2-Des-Luc2 (CSk-SH2), AAV9sc-CSk-SH3-Des-Luc2 (CSk-SH3), AAV9sc-CSk-SH4-Des-Luc2 (CSk-SH4), AAV9sc-CSk-SH5-Des-Luc2 (CSk-SH5), or AAV9sc-CSk-SH6-Des-Luc2 (CSk-SH6) vector. Luciferase expression was measured as total flux, expressed in photons per second per centimetre squared per steradian (photons/sec/$cm^2$/sr), released by luciferase activity in the selected tissue at 9 weeks post-injection. Results were presented as mean±standard error of the mean. (B) Luc mRNA level in selected tissues of mice that were intravenously injected with, from left to right, AAV9sc-CSk-SH1-Des-Luc2 (CSk-SH1), AAV9sc-CSk-SH2-Des-Luc2 (CSk-SH2), AAV9sc-CSk-SH3-Des-Luc2 (CSk-SH3), AAV9sc-CSk-SH4-Des-Luc2 (CSk-SH4), AAV9sc-CSk-SH5-Des-Luc2 (CSk-SH5), or AAV9sc-CSk-SH6-Des-Luc2 (CSk-SH6) vector compared to mice that were injected with the control vector AAV9sc-Des-Luc2 (control, no Csk-SH). Luc mRNA levels were measured by a quantitative RT-PCR method (qRT-PCR) at the end of the experiment from total RNA extracted from biopsies from the indicated tissues. Results were presented as mean±standard error of the mean.
Figure 5B:
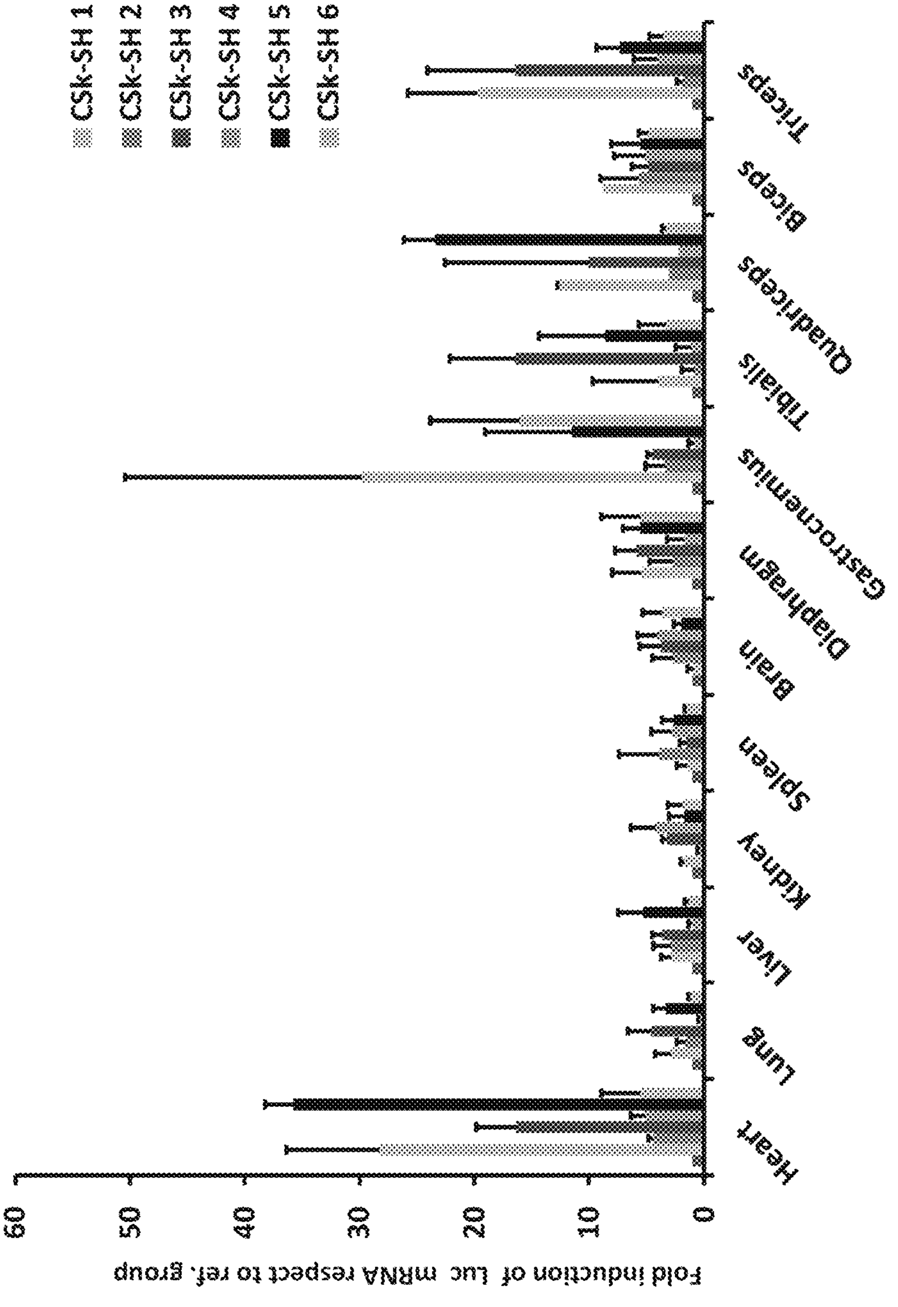

We also determined luciferase activity in the individual organs. Nine weeks post injection, the mice were euthanized and individual organs were analyzed to evaluate luciferase expression and the biodistribution pattern. We observed significantly increased levels of luciferase activity in the heart, the biceps, the triceps, the quadriceps, the tibialis interior, and the gastrocnemius muscle of mice injected with AAV vector comprising a regulatory element CSk-SH1-6 as compared to control mice. Up to 48-fold augmentation of luciferase activity was measured in the heart of mice injected with AAV vector comprising the CSk-SH5 regulatory element as compared to control mice (FIG. 4A). This regulatory element was also the most robust in muscle, in particular gastrocnemius muscle, tibialis interior, quadriceps, biceps and triceps. Hence, the most potent regulatory element was CSk-SH5. The second most robust regulatory element was CSk-SH1. A 25-fold augmentation of luciferase activity was measured in the heart of mice injected with AAV vector comprising CSK-SH1 when compared to control mice. Robust luciferase activity was also measured in other muscle of mice injected with CSk-SH1. The third robust regulatory element was CSk-SH3, followed by CSk-SH6, CSk-SH4 and CSk-SH2. Furthermore the expression was specific for cardiac and skeletal muscle as luciferase expression was absent or limited in all other organs (FIG. 5A), despite transduction of the vector into the other organs (FIG. 6A-B). The level of luciferase activity measured in the organs was consistent with the luciferase mRNA levels measured in the respective organs (FIG. 4B, 5B). These in vivo data show that the nucleic acid regulatory elements CSk-SH, in particular CSk-SH1, CSk-SH3 and CSk-SH5, more particularly CSk-SH1 and Csk-SH5, can enhance heart and skeletal muscle-specific luciferase expression.

Example 3

Identification of Skeletal Muscle-Specific Regulatory Elements

Experimental Procedures

First, a list of muscle-specific genes was extracted from the Tissue-specific Gene Expression and Regulation (Ti- GER) database. This was used to identify a set of the most highly expressed (i.e. 'over-expressed') genes in muscle tissue. Conversely, a set of 'under-expressed' genes was identified, corresponding to those genes that exhibited the lowest expression in muscle. Next, the Reference Sequence (RefSeq) identifiers (IDs) lists of these 'over-expressed' and 'under-expressed' muscle-specific genes were used to extract the corresponding promoter sequences upstream the reported transcription start sites (TSSs) by 1000 bases (NCBI36/hg18 genome assembly), using the transcription start location data stored in the refGene table of the UCSC Genome Browser (http://genome.ucsc.edu) database. This resulted in two sets of muscle-specific promoter sequences corresponding to promoters of 'over-expressed' or 'under-expressed' genes. In order to make a non-redundant set of representative promoter sequences, the promoter sequences were filtered using 'uclust' (http://www.drive5.com/usearch/).

The two sets of non-redundant tissue-specific promoter sequences corresponding to promoters of 'over-expressed' or 'under-expressed' genes were used as input for the DDM/MDS method, described in detail in De Bleser et al. (2007. Genome Biol 8:R83), which is specifically incorporated by reference herein. The observed differential behaviour might be explained by the presence of one or more TFBS elements characteristic of the promoters of the up-regulated or down-regulated group of genes. These 'differential' TFBS elements could be found using following procedure. First, a library of TFBS positional weight matrices (PWMs) (TRANSFAC® 2010.3) was used to predict TFBS on every promoter sequence. For the muscle-specific promoters we used the Find Individual Motif Occurences (fimo) application with a P-value cut-off of $10^{-3}$. The number of predicted TFBS elements per PWM per promoter was collected in the form of a matrix in which each row corresponds to a promoter sequence, while the columns corresponded to the used PWM. Two TFBS were considered correlated if their corresponding columns in the matrix were similar what could be measured using a distance function. With this approach, distance matrices summarizing all TFBS associations were constructed for the TFBS in both sets of promoters. Finally, by calculating the distance difference matrix (DDM) and performing multidimensional scaling on this DDM to visualize its content in two dimensions, TFBS could be distinguished that did not contribute to the observed differential gene expression as they were mapped near the origin of the DDM-MDS plot from 'deviating' TFBS that are likely responsible for the observed differential gene expression. As the MDS procedure plots TFBS that are strongly associated closer together than less associated ones, it was able to highlight interactions between TFBS in the promoter datasets. This procedure resulted in a list of TFBS associated with high tissue-specific expression for muscle-specific promoters.

Next, the genomic context of the tissue-specific over-expressed genes was searched for cross-species conserved regions for the TFBS associated with high tissue-specific gene expression. For that purpose, the sequences of all conserved sequence elements in the NCBI36/hg18 genome assembly were downloaded based on the information stored in the phastConsElements44way table of the UCSC Genome Browser (http://genome.ucsc.edu) database. The predicted conserved sequence elements are assigned a log-odds score equal to its log probability under the conserved model minus its log probability under the non-conserved model. This allows to restrict the search for putative regulatory elements that coincide with the most conserved sequence elements. The conserved sequence elements were scanned for TFBS associated with high tissue-specific expression using the fimo application, as described above. Using internally developed Perl scripts, this led to the identification of highly conserved sequence elements containing clusters of TFBS associated with high tissue-specific expression (i.e. nucleic acid regulatory elements). Additional filtering was done by selecting the putative nucleic acid regulatory elements that either overlapped or contained regions bearing reproducible biochemical features associated with transcription regulation and/or a open chromatin structure as defined in the ENCODE project (The ENCODE Project Consortum. 2012. Nature 489:57-74).

Results

This computational approach led to the identification of 6 muscle-specific regulatory sequences, summarized in Table 3.

TABLE 3

Muscle-specific regulatory elements.

| Sequence | Name | Gene regulated by sequence | Size (bp) | Conserved TFBS present |
|---|---|---|---|---|
| SEQ ID NO: 7 | Sk-SH1 | ATP2A1 | 495 | E2A, NF1, SRFC, p53, CEBP, LRF, MyoD |
| SEQ ID NO: 8 | Sk-SH2 | TNNI1 | 344 | E2A, NF1, CEBP, LRF, MyoD, SREBP |
| SEQ ID NO: 9 | Sk-SH3 | TNNI1 | 430 | E2A, HNF3a, CEBP, LRF, MyoD, SREBP, Tal1_b |
| SEQ ID NO: 10 | Sk-SH4 | MYLPF | 435 | E2A, SRF, p53, CEBP, LRF, MyoD, SREBP |
| SEQ ID NO: 11 | Sk-SH5 | MYH1 | 474 | HNF4, NF1, RSRFC4, CEBP, LRF, SREBP |
| SEQ ID NO: 12 | Sk-SH6 | TPM3 | 519 | E2A, HNF3a, HNF3b, NF1, SRF, CEBP, LRF, MyoD, SREBP |
| SEQ ID NO: 13 | Sk-SH7 | ANKRD2 | 372 | E2A, CEBP, MyoD |

Bp: base pairs.

Example 4

In Vivo Validation of Skeletal Muscle-Specific Regulatory Elements Via AAV Vectors Comprising a Desmin Promoter Experimental Procedures AAV plasmid constructs comprising a skeletal muscle-specific regulatory element (pAAV-Sk-SH-Des-Luc2) were generated according to the protocol described in Example 2. Briefly, the skeletal muscle-specific regulatory elements were synthesized by conventional oligonucleotide synthesis and flanked with Acc651 and MluI restriction sites (Sk-SH1, 2, 3, 4, 5 and 7) or BsiWI and MluI restriction sites (Sk-SH6). The different Sk-SHs were cloned upstream of the Desmin (Des) promoter that drives expression of a Firefly Luciferase (Luc2) reporter gene in the context of the AAV vector backbone pAAV-Des-Luc2. The plasmids also contained a Minute Virus of Mouse (MVM) intron and a Simian Virus 40 (SV40) polyadenylation site (pA).

AAV vector production and purification and animal studies were carried out as described in Example 2. The experimental design is summarized in Table 4.

TABLE 4

Experimental design for the injection of skeletal muscle-specific regulatory elements.

| Vector | Mouse number (n) | Dose | Titre (gc/ml) | Volume vector (μl) | Volume PBS (μl) | Total volume (μl) |
|---|---|---|---|---|---|---|
| AAV9sc. Des.Luc2 | 5 | $5 \times 10^9$ | $5.7 \times 10^{11}$ | 8.7 | 41.3 | 50 |
| AAV9sc. Sk-SH1.Des.Luc2 | 4 | $5 \times 10^9$ | $1.7 \times 10^{11}$ | 29.4 | 20.6 | 50 |
| AAV9sc. Sk-5H2.Des.Luc2 | 4 | $5 \times 10^9$ | $1.8 \times 10^{11}$ | 27.7 | 22.3 | 50 |
| AAV9sc. Sk-5H3.Des.Luc2 | 4 | $5 \times 10^9$ | $1.9 \times 10^{11}$ | 26.3 | 23.7 | 50 |
| AAV9sc. Sk-5H4.Des.Luc2 | 4 | $5 \times 10^9$ | $1.6 \times 10^{11}$ | 31.3 | 18.7 | 50 |
| AAV9sc. Sk-5H5.Des.Luc2 | 1 | $5 \times 10^9$ | $8.1 \times 10^{11}$ | 62 | 3 | 65 |
| AAV9sc. Sk-5H6.Des.Luc2 | 3 | $5 \times 10^9$ | $1.410^{11}$ | 35.7 | 14.3 | 50 |
| AAV9sc. Sk-5H7.Des.Luc2 | 4 | $5 \times 10^9$ | $1.8 \times 10^{11}$ | 27.7 | 22.3 | 50 |

mRNA analysis and transduction efficiency and vector biodistribution were assessed as described in Example 2.

Results

Adeno-associated vectors were generated that expressed the luciferase gene luc2 from a chimeric promoter composed of the desmin (Des) promoter linked to the skeletal muscle-specific regulatory elements Sk-SH1-7. The vectors were intravenously injected in mice and whole body images were taken from the mice at 5 and 6 weeks post-injection to examine luciferase expression level.

All mice injected with a vector comprising a skeletal muscle-specific regulatory element (Sk-SH1-7) showed increased luciferase activity compared to control mice that were injected with a corresponding AAV9 vector without a regulatory element, indicating that all of the regulatory elements tested increased luciferase expression from the desmin promoter (data not shown). We observed very robust and enhanced luciferase activity in mice that were injected with AAV9 vector comprising the regulatory element Sk-SH1 or Sk-SH4 at 5 and 6 weeks post-injection as compared to luciferase activity of the control mice.

Figure 8:
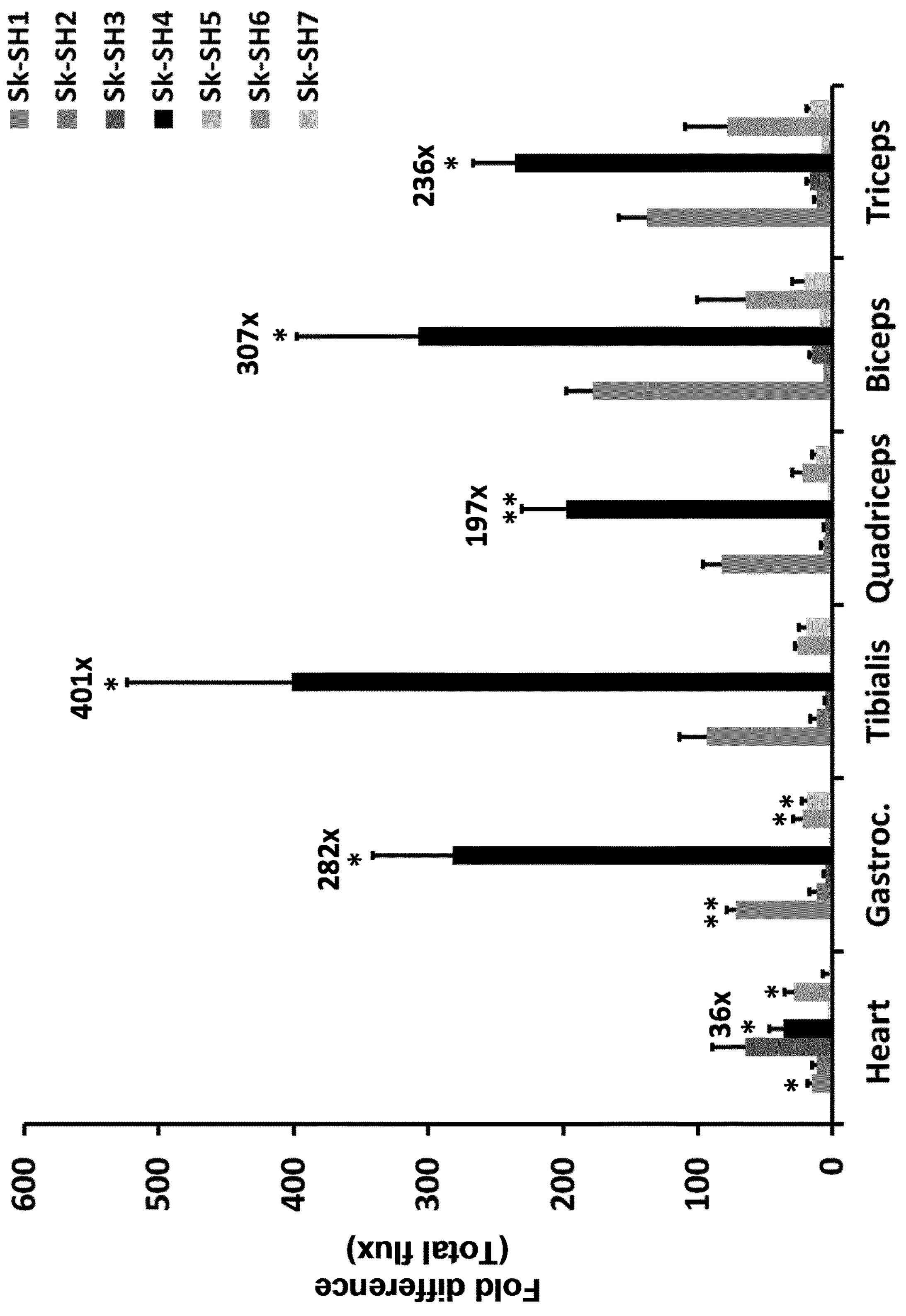
FIG. 8 shows difference in luciferase expression in heart and muscle tissue of mice that were intravenously injected with, from left to right, AAV9sc-Sk-SH1-Des-Luc2 (Sk-SH1, n=4), AAV9sc-Sk-SH2-Des-Luc2 (Sk-SH2, n=4), AAV9sc-Sk-SH3-Des-Luc2 (Sk-SH3, n=4), AAV9sc-Sk-SH4-Des-Luc2 (Sk-SH4, n=4), AAV9sc-Sk-SH5-Des-Luc2 (Sk-SH5, n=1), AAV9sc-Sk-SH6-Des-Luc2 (Sk-SH5, n=3) or AAV9sc-Sk-SH7-Des-Luc2 (Sk-SH6, n=4) vector compared to mice that were injected with the control vector AAV9sc-Des-Luc2 without nucleic acid regulatory element (control, no Sk-SH, n=5). Luciferase expression was measured as total flux, expressed in photons per second per centimetre squared per steradian (photons/sec/$cm^2$/sr), released by luciferase activity in the selected tissues at 7 weeks post-injection. Results were presented as mean±standard error of the mean, *$p<0.05$; **$p<0.001$.
Figure 9:
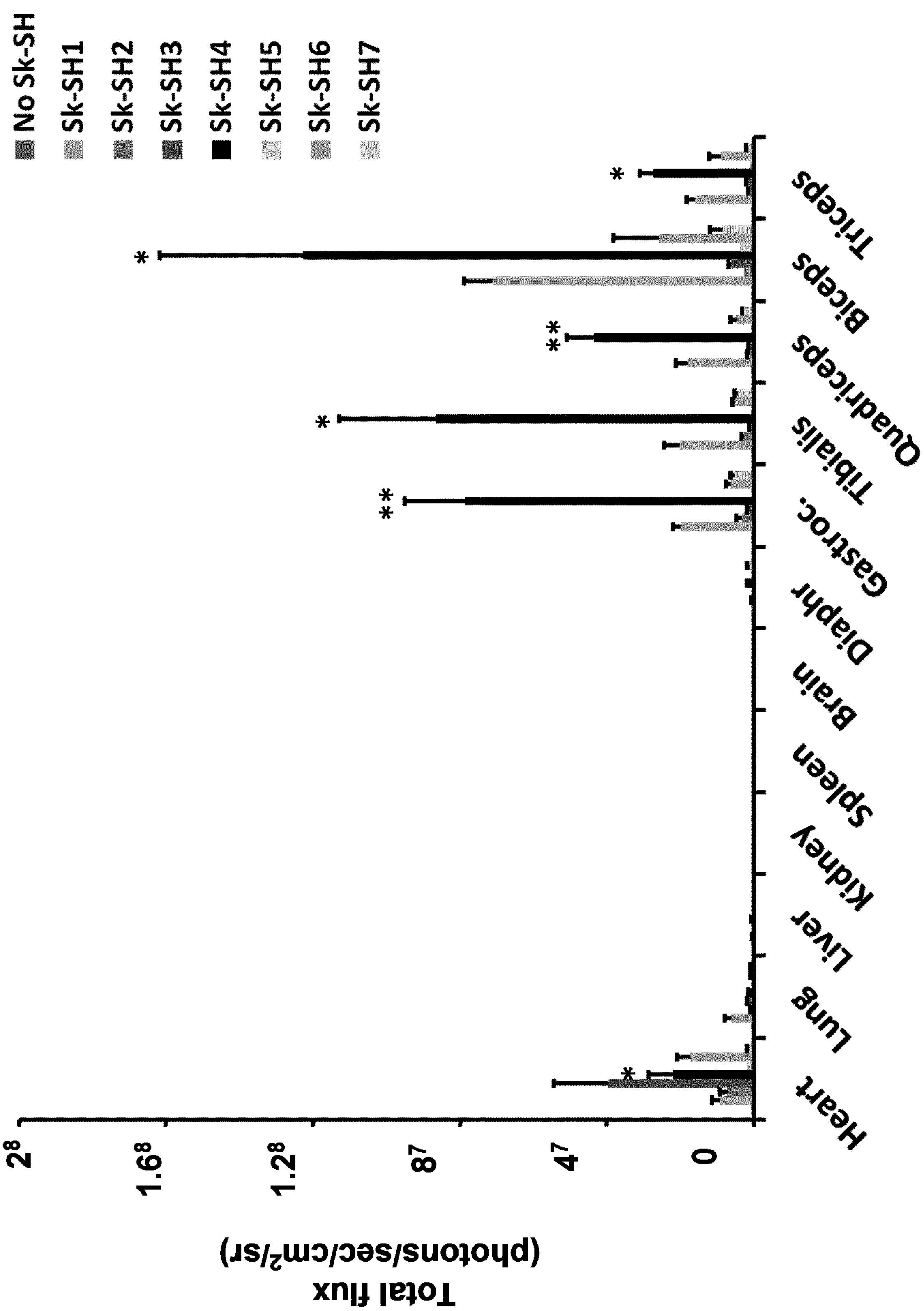
FIG. 9 shows luciferase expression in selected tissues of mice that were intravenously injected with, from left to right, AAV9sc-Des-Luc2 (control, no Sk-SH, n=5), AAV9sc-Sk-SH1-Des-Luc2 (Sk-SH1, n=4), AAV9sc-Sk-SH2-Des-Luc2 (Sk-SH2, n=4), AAV9sc-Sk-SH3-Des-Luc2 (Sk-SH3, n=4), AAV9sc-Sk-SH4-Des-Luc2 (Sk-SH4, n=4), AAV9sc-Sk-SH5-Des-Luc2 (Sk-SH5, n=1), AAV9sc-Sk-SH6-Des-Luc2 (Sk-SH5, n=3), or AAV9sc-Sk-SH7-Des-Luc2 (Sk-SH6, n=4) vector. Luciferase expression was measured as total flux, expressed in photons per second per centimetre squared per steradian (photons/sec/$cm^2$/sr), released by luciferase activity in the selected tissue at 7 weeks post-injection. Results were presented as mean±standard error of the mean, *$p<0.05$; **$p<0.001$.

7 weeks post injection, the mice were euthanized and individual organs were analyzed to evaluate luciferase expression and the biodistribution pattern (FIGS. 8 and 9). Up to 200 to 400-fold augmentation of luciferase activity was measured in skeletal muscle, in particular gastrocnemius muscle, tibialis interior, quadriceps, biceps and triceps, of mice injected with AAV vector comprising the Sk-SH4 regulatory element as compared to control mice (FIG. 8). There was still a 36-fold augmentation of luciferase activity measured in the heart of said mice (FIG. 8), due to the use of the desmin promoter, which is specific for both, heart and skeletal muscle. Luciferase expression was absent or limited in all other organs than cardiac and skeletal muscle tissue (FIG. 9). The second most robust regulatory element was Sk-SH1, which also specifically increased luciferase expression from the desmin promoter in skeletal muscle, and to a lesser extent in heart muscle.

Figure 12:
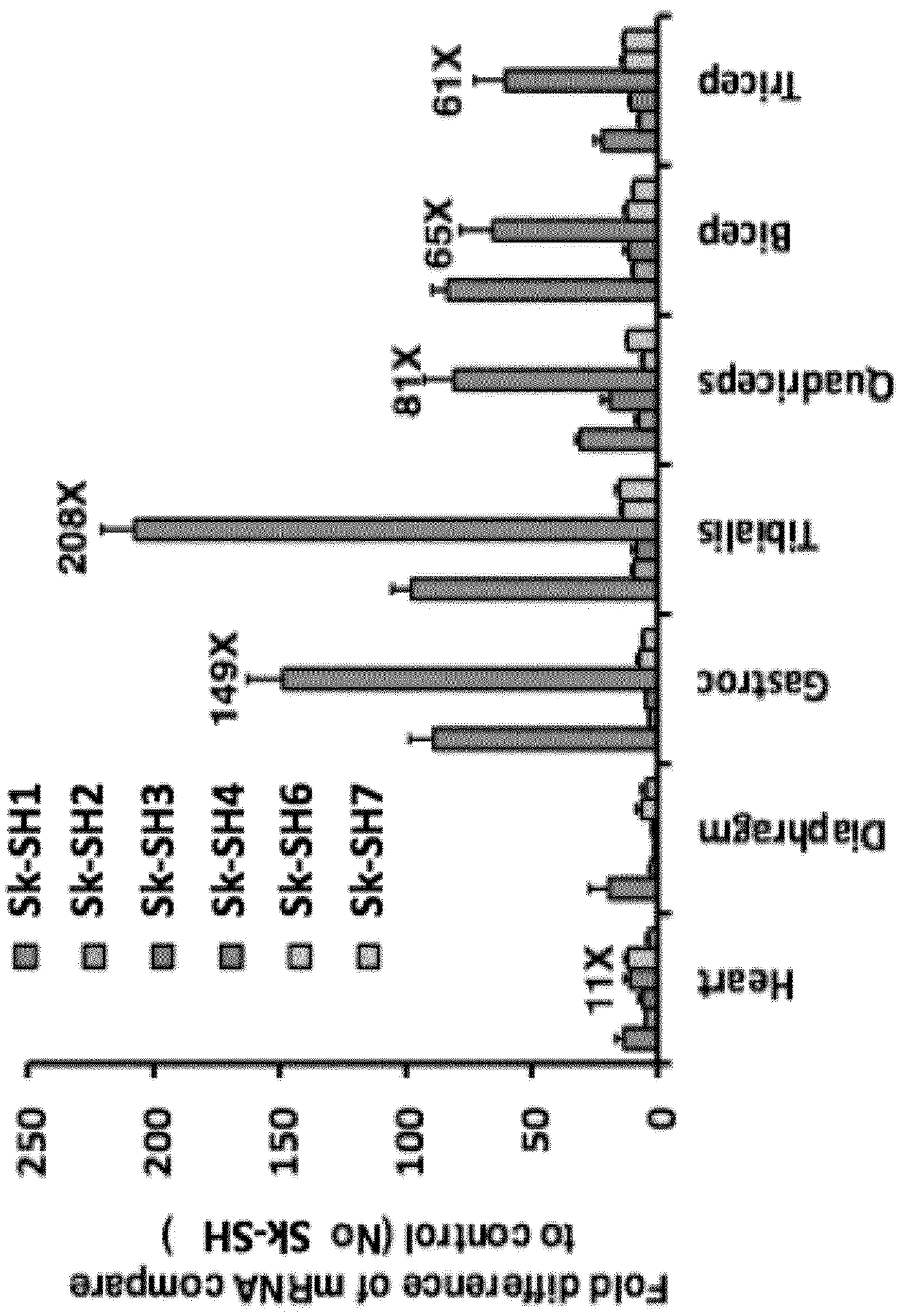
FIG. 12: Difference in Luc mRNA level in heart and muscle tissue of mice that were intravenously injected with, from left to right, AAV9sc-Sk-SH1-Des-Luc2 (Sk-SH1), AAV9sc-Sk-SH2-Des-Luc2 (Sk-SH2), AAV9sc-Sk-SH3-Des-Luc2 (Sk-SH3), AAV9sc-Sk-SH4-Des-Luc2 (Sk-SH4), AAV9sc-Sk-SH6-Des-Luc2 (Sk-SH6), or AAV9sc-Sk-SH7-Des-Luc2 (Sk-SH7) vector compared to mice that were injected with the control vector AAV9sc-Des-Luc2 without nucleic acid regulatory element (control, no Sk-SH). Luc mRNA levels were measured by a quantitative RT-PCR method (qRT-PCR) from total RNA extracted from biopsies from the indicated tissues. Results were presented as mean±standard error of the mean, $*p<0.05$; $**p<0.001$.

The level of luciferase activity measured in the heart and different skeletal muscles was consistent with the luciferase mRNA levels measured in the respective organs (FIG. 12). Notwithstanding the transduction of the vector into different organs as shown in FIG. 13, luciferase expression was absent or limited in all other organs than cardiac and skeletal muscle tissue (FIG. 9).

These in vivo data show that the nucleic acid regulatory elements Sk-SH, in particular Sk-SH1 and Sk-SH4, can enhance heart and skeletal muscle-specific luciferase expression.

The nucleic acid regulatory element Sk-SH4 is by far the most robust element that led to the highest level of luciferase expression in the heart and skeletal muscle as compared to the other 5 regulatory elements that were identified. The highest activity that we measured was a 400-fold upregulation of luciferase activity in the tibialis.

Example 5

In Vivo Comparison of Muscle-Specific Regulatory Elements and CMV Promoter

Experimental Procedures

AAV plasmid constructs comprising a muscle-specific regulatory element (pAAV-Sk-SH4-Des-Luc2, pAAV-CSk-SH1-Des-Luc2, pAAV-CSk-SH5-Des-Luc2) were generated according to the protocol described in Example 2. Briefly, the muscle-specific regulatory elements were synthesized by conventional oligonucleotide synthesis and cloned upstream of the Desmin (Des) promoter that drives expression of a Firefly Luciferase (Luc2) reporter gene in the context of the AAV vector backbone pAAV-Des-Luc2. The plasmids also contained a Minute Virus of Mouse (MVM) intron and a Simian Virus 40 (SV40) polyadenylation site (pA).

Figure 10A:
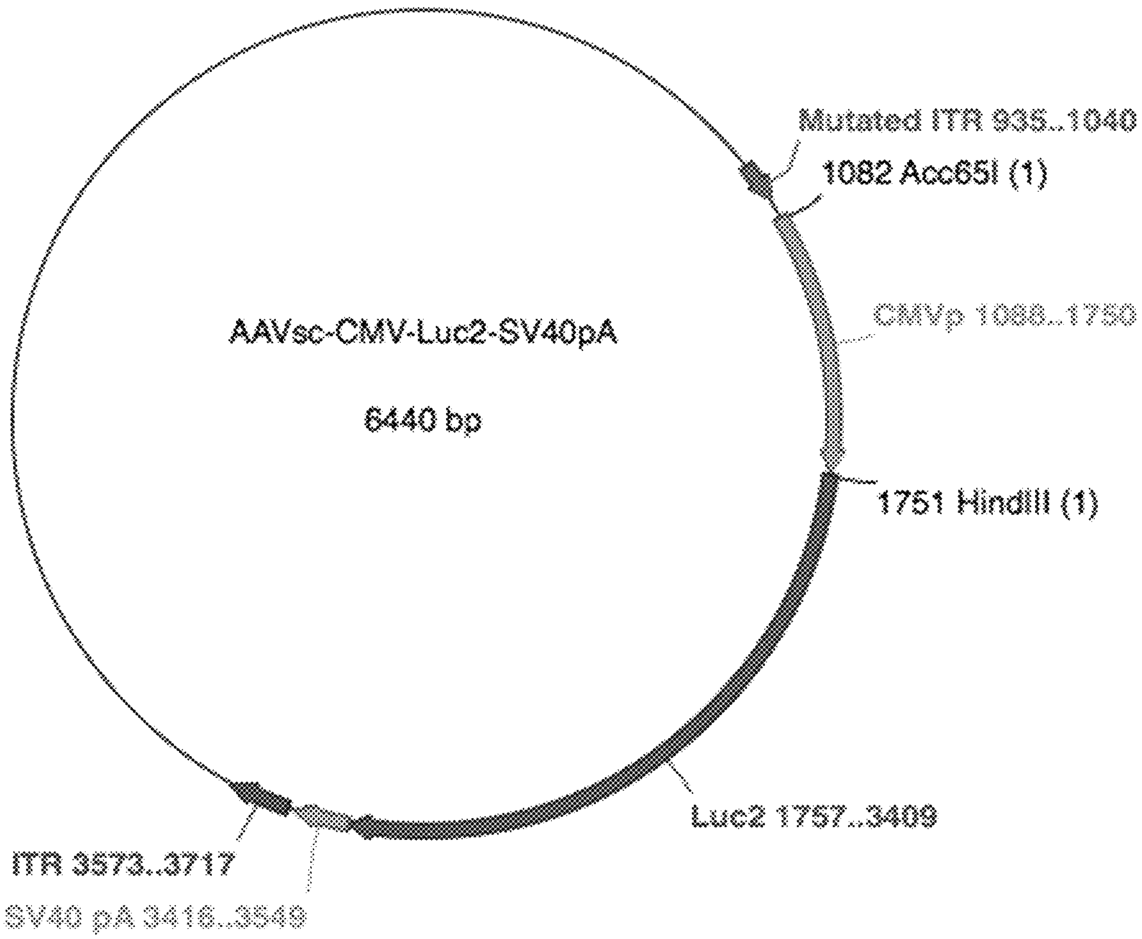
FIG. 10: (A) Schematic diagram of the AAVsc-CMV-Luc2-SV40 pA plasmid construct with indication where the Cytomegalovirus promoter (CMVp) is cloned upstream of the Firefly Luciferase gene (Luc2). Abbreviations used are: ITR: viral inverted terminal repeat; SV40 pA: Simian Virus 40 polyadenylation site. (B) Luciferase expression in selected tissues of mice that were intravenously injected with, from left to right, AAV9sc-CMV-Luc2 (CMV, n=4), AAV9sc-Sk-SH4-Des-Luc2 (Sk-SH4, n=2), AAV9sc-CSk-SH1-Des-Luc2 (CSk-SH1, n=4), or AAV9sc-CSk-SH5-Des-Luc2 (CSk-SH5, n=4) vector. Luciferase expression was measured as total flux, expressed in photons per second per centimetre squared per steradian (photons/sec/$cm^2$/sr), released by luciferase activity in the selected tissue. Results were presented as mean±standard error of the mean. (C) Difference in luciferase expression in heart and muscle tissue of mice that were intravenously injected with, from left to right, AAV9sc-Sk-SH4-Des-Luc2 (Sk-SH4, n=2), AAV9sc-CSk-SH1-Des-Luc2 (CSk-SH1, n=4), or AAV9sc-CSk-SH5-Des-Luc2 (CSk-SH5, n=4) vector compared to mice that were injected with vector AAV9sc-CMV-Luc2 (CMV, n=4). Luciferase expression was measured as total flux, expressed in photons per second per centimetre squared per steradian (photons/sec/$cm^2$/sr), released by luciferase activity in the selected tissues at 7 weeks post-injection. Results were presented as mean±standard error of the mean.

A pAAVsc-CMV-Luc2-SV40 pA plasmid construct was generated, wherein the Cytomegalovirus (CMV) promoter (SEQ ID NO: 30) is cloned upstream the Firefly Luciferase (Luc2) reporter gene instead of the desmin promoter in the context of the AAV vector backbone pAAV-Des-Luc2. The plasmid also contained a Simian Virus 40 (SV40) polyadenylation site (pA). A schematic representation of pAAVsc-CMV-Luc2-SV40 pA is shown in FIG. 10A. For the cloning of the AAVsc-CMV-Luc2-SV40 pA, the fragment 5'-Acc651-CMV-HindIII-3' was synthesised and cloned into an AAVsc-Luc2-SV40 pA vector which was restricted with the same pair of enzymes (i.e. Acc651 and HindIII).

AAV vector production and purification were carried out as described in Example 2.

6 weeks old male CB17 SC SCID mice having an average weight of 17.4±1.6 g were intravenously injected into the periorbital vein with $1\times10^{10}$ vg/mouse of concentrated vectors. Mice were imaged 4 weeks post-injection as described in Example 2. Mice were euthanized 5 weeks post-injection and intact organs were harvested and imaged as described in Example 2.

Results

Luciferase activity was compared in mice that were injected with a vector that expressed the luciferase gene luc2 from the desmin (Des) promoter operably linked to a muscle-specific regulatory element: SK-SH4, CSk-SH1 or CSk-SH5, versus mice that were injected with a vector that expressed the luciferase gene luc2 from the Cytomegalovirus (CMV) promoter. The CMV promoter is considered one of the most powerful promoters known to allow robust gene expression in the heart. No muscle-specific regulatory element was present in the latter vectors.

Figure 10B:
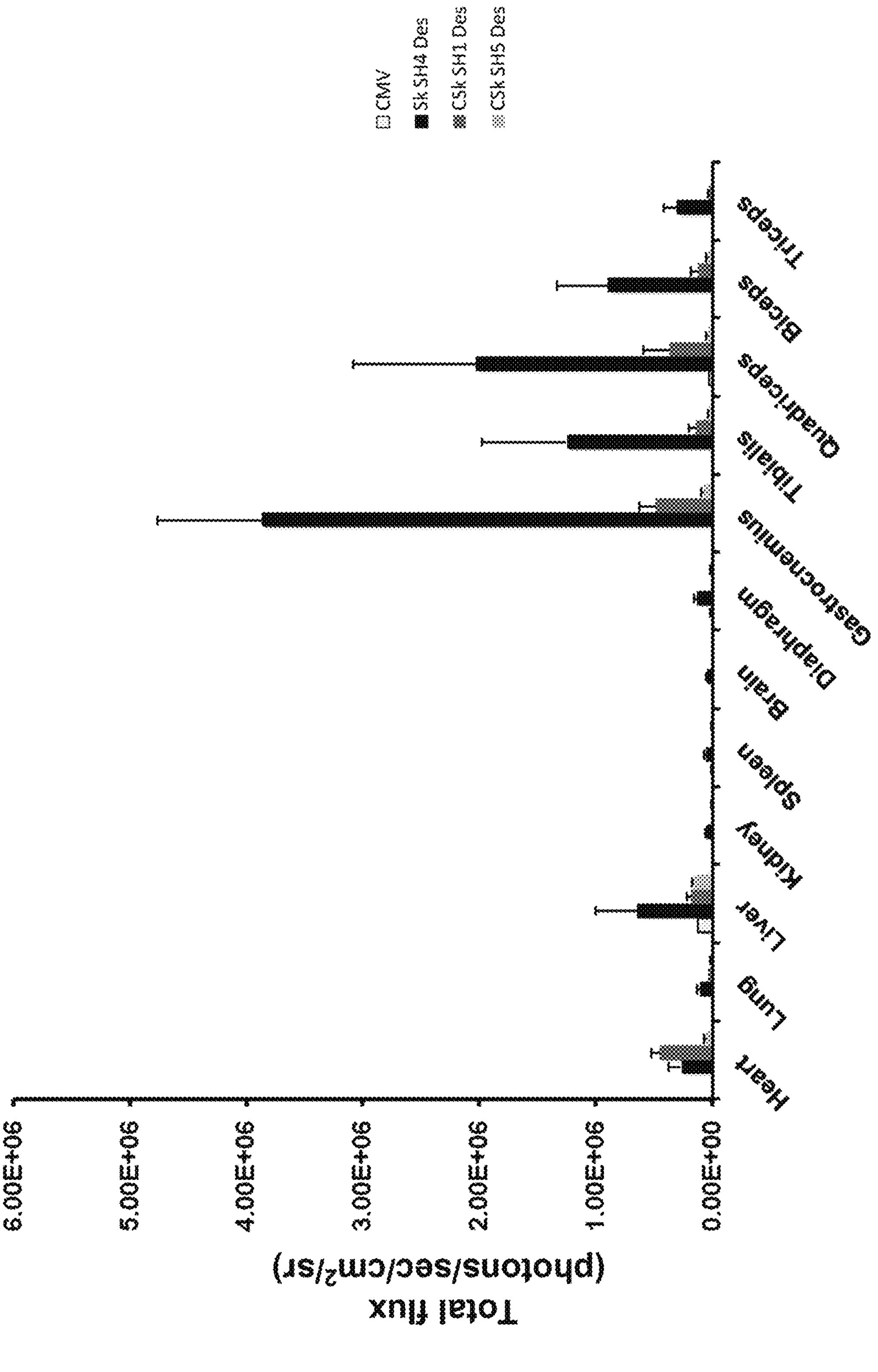
Figure 10C:
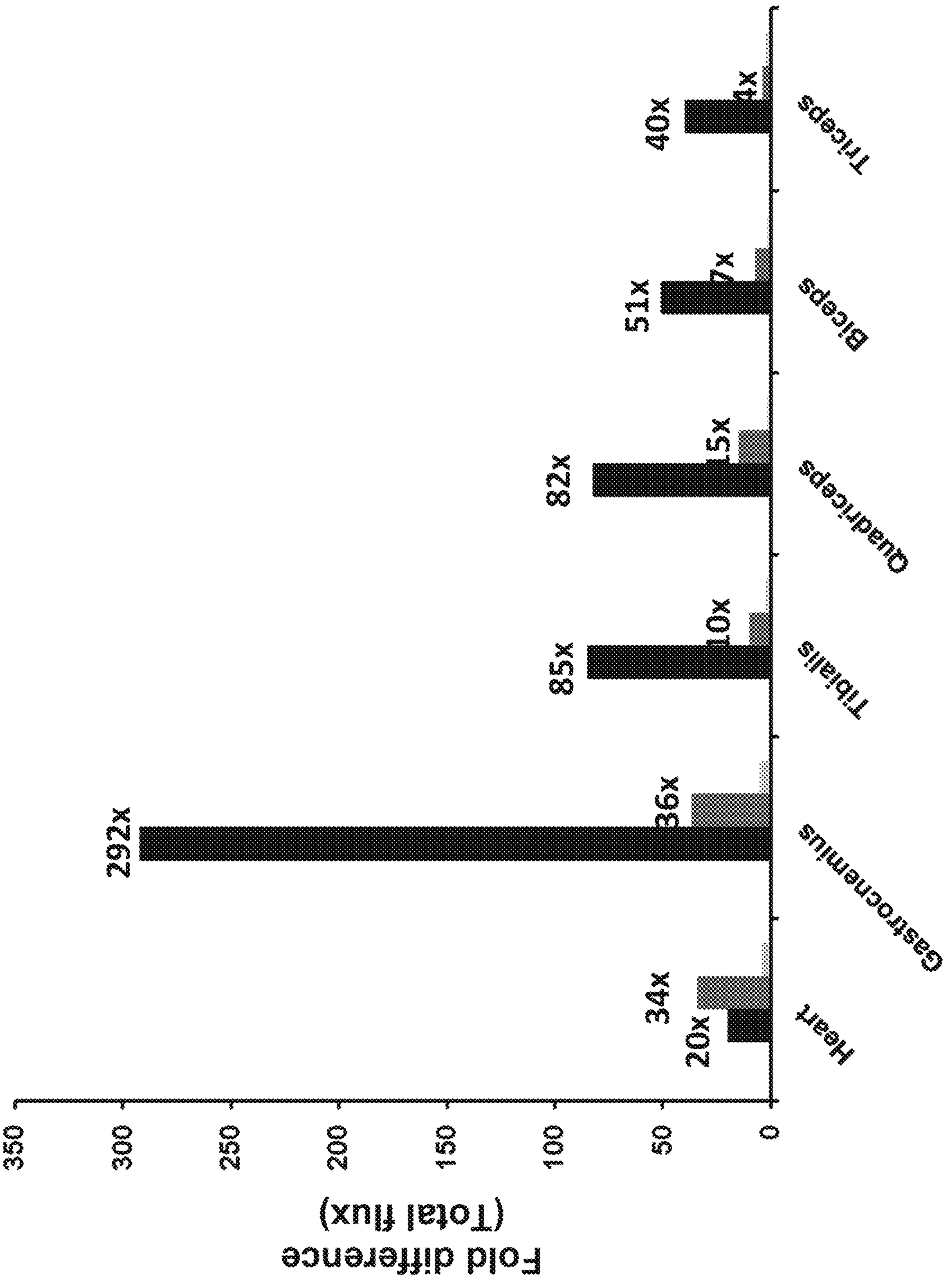

FIGS. 10A and 10B show that the vectors comprising a muscle-specific regulatory element of the invention operably linked to the desmin promoter allow for much better expression than the vector comprising the CMV promoter.

Example 6

In Vivo Validation of Skeletal Muscle-Specific Regulatory Elements Via AAV Vectors Comprising a Skeletal Muscle-Specific Promoter Experimental Procedures AAV plasmids are constructed as described in Example 4, wherein the desmin promoter is replaced by the muscle-specific promoter described in Wang et al. (2008. Gene Ther. 15:1489-1499).

AAV vector production and purification and animal studies are carried out as described in Example 2.

Results

When using a skeletal muscle-specific promoter instead of the desmin promoter, the increase in luciferase expression is confined to skeletal muscle only, showing that the nucleic acid regulatory elements Sk-SH1-7, in particular Sk-SH4 and Sk-SH1 enhance skeletal muscle-specific luciferase expression.

Example 7

Figure 11A:
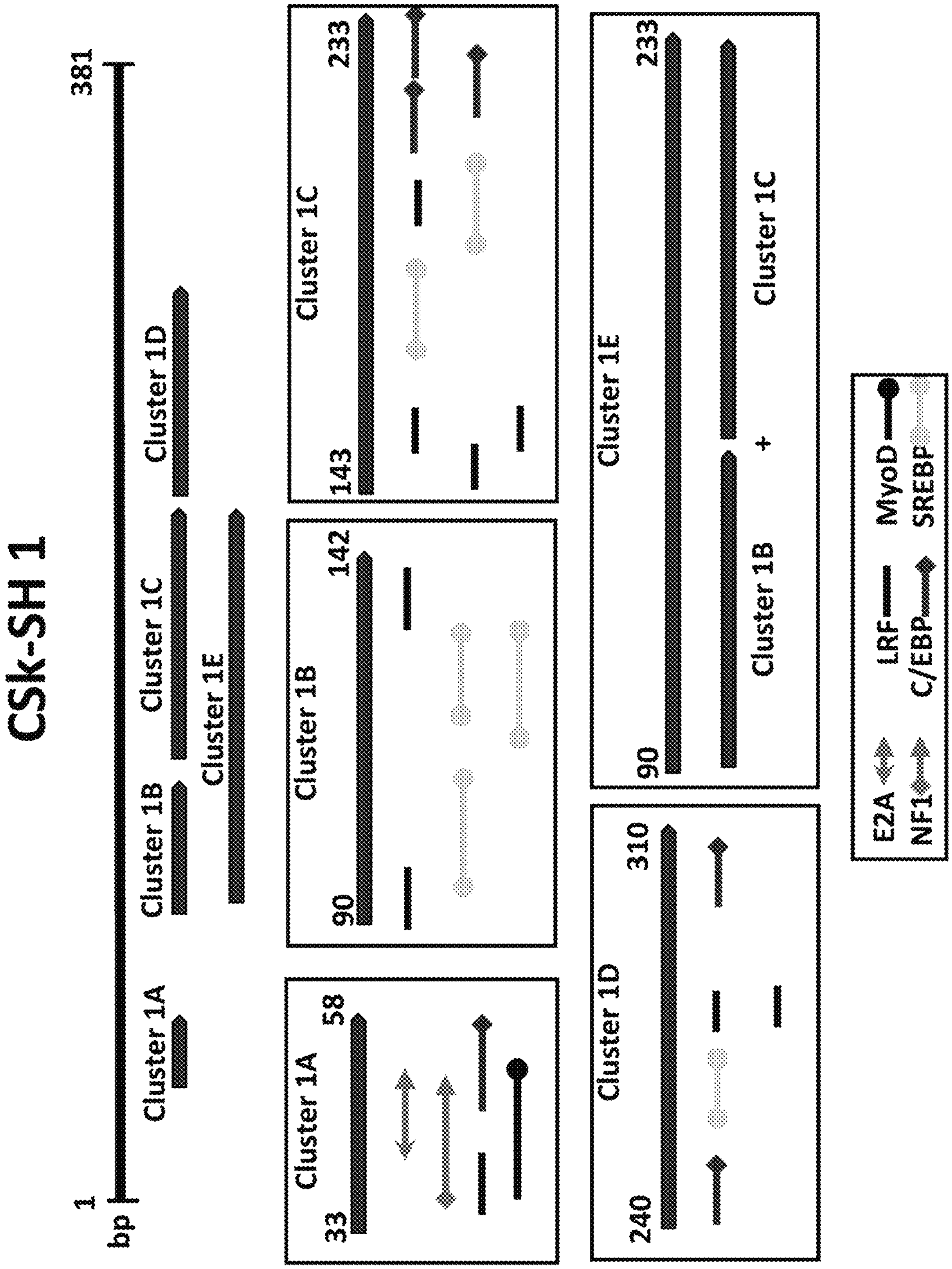
FIG. 11 shows functional fragments and the indicated transcription binding sites (TFBS) of CSk-SH1 (A), CSk-SH-5 (B), and Sk-SH4 (C) mapped on a schematic representation of respectively, SEQ ID NO:1 (A), SEQ ID NO:5 (B), and SEQ ID NO:10 (C).
Figure 11B:
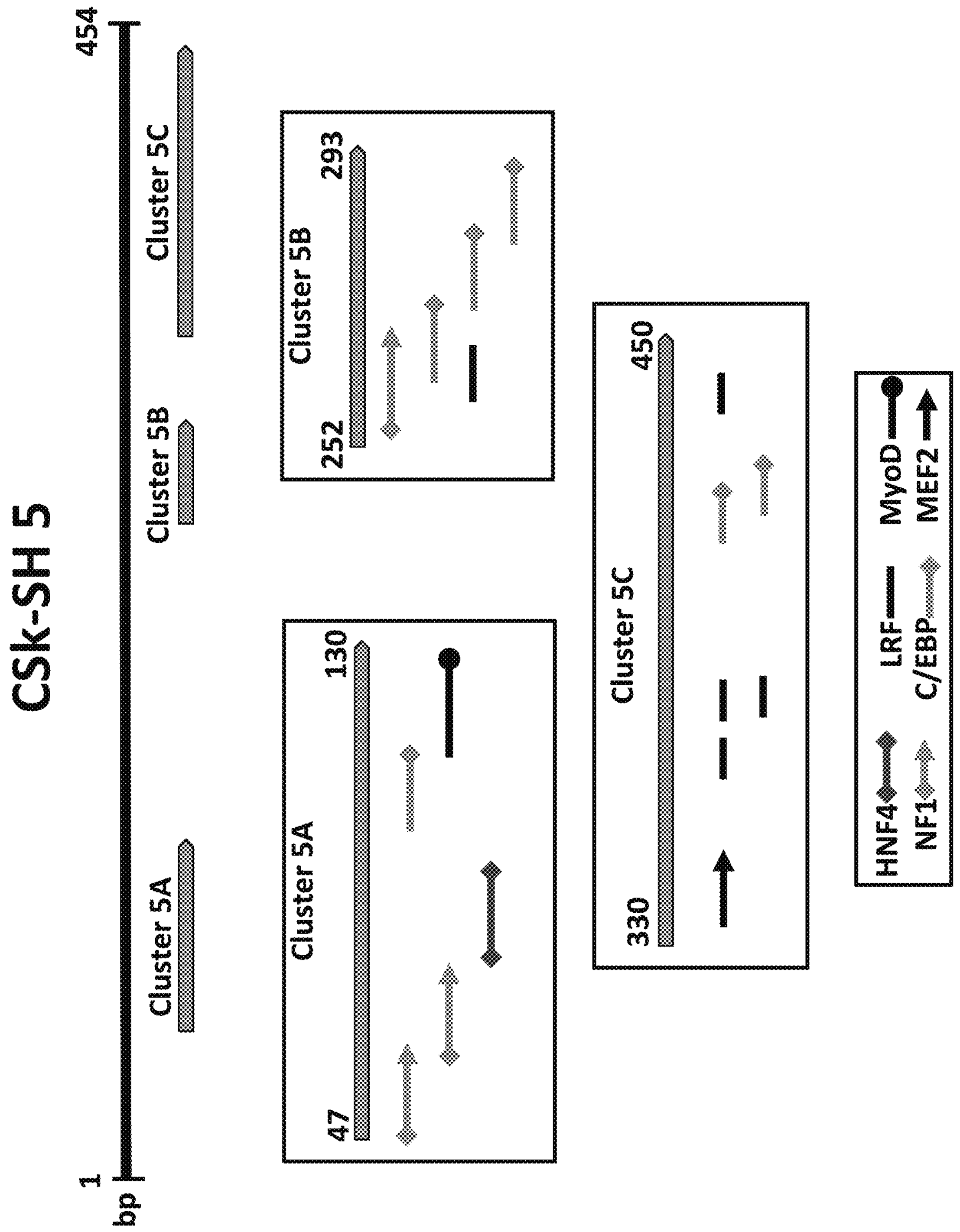
Figure 11C:
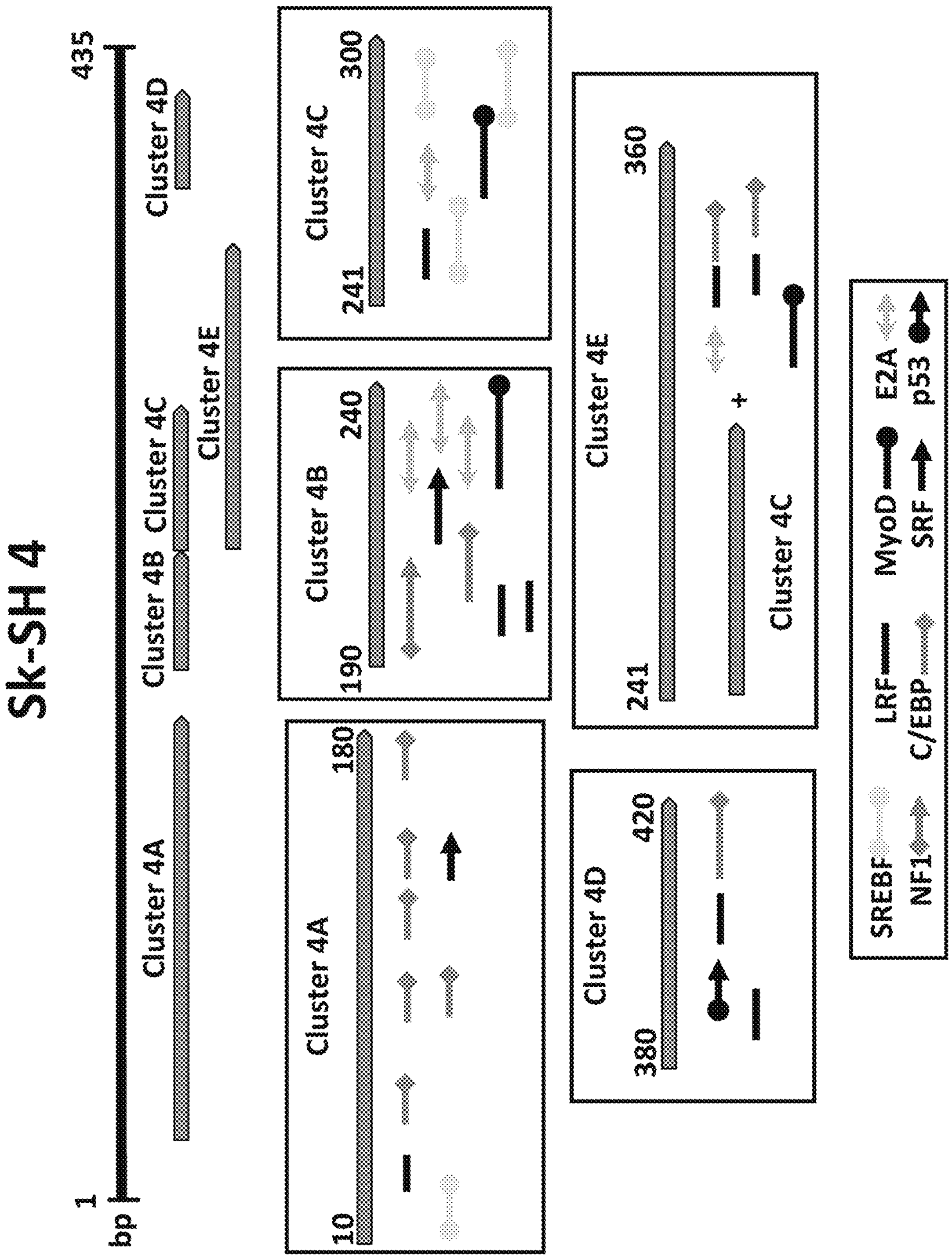

In Vivo Validation of Functional Fragments of the Identified Muscle-Specific Regulatory Elements Experimental Procedures The identified nucleic acid regulatory elements CSk-SH1 (SEQ ID NO: 1; 381 bp), CSk-SH5 (SEQ ID NO:5; 454 bp) and Sk-SH4 (SEQ ID NO:10; 435 bp) were split into smaller functional fragments. The transcription factor binding sites (TFBS) of the regulatory elements were mapped on the respective sequence (FIG. 11A-C), and functional fragments were generated by randomly clustering regions with TFBS. The following functional fragments were generated:

Functional Fragments of SEQ ID NO:1:

Cluster 1A: the nucleotide sequence from position 33 to 58 in SEQ ID NO:1

Cluster 1B: the nucleotide sequence from position 90 to 142 in SEQ ID NO:1

Cluster 1C: the nucleotide sequence from position 143 to 233 in SEQ ID NO:1

Cluster 1D: the nucleotide sequence from position 240 to 310 in SEQ ID NO:1

Cluster 1E: the nucleotide sequence from position 90 to 233 in SEQ ID NO:1

Functional Fragments of SEQ ID NO:5:

Cluster 5A: the nucleotide sequence from position 47 to 130 in SEQ ID NO:5

Cluster 5B: the nucleotide sequence from position 252 to 293 in SEQ ID NO:5

Cluster 5C: the nucleotide sequence from position 330 to 450 in SEQ ID NO:5

Functional Fragments of SEQ ID NO:10:

Cluster 4A: the nucleotide sequence from position 10 to 180 in SEQ ID NO:10 (SEQ ID NO: 37);

Cluster 4B: the nucleotide sequence from position 190 to 240 in SEQ ID NO:10 (SEQ ID NO: 38);

Cluster 4C: the nucleotide sequence from position 241 to 300 in SEQ ID NO:10 (SEQ ID NO: 39);

Cluster 4E: the nucleotide sequence from position 241 to 360 in SEQ ID NO:10 (SEQ ID NO:41)

Cluster 4D: the nucleotide sequence from position 380 to 420 in SEQ ID NO:10 (SEQ ID NO: 40)

The functional fragments of Sk-SH4 are summarized in Table 5.

TABLE 5

Functional fragments of the muscle-specific regulatory element Sk-SH4.

| Sequence | Name | Gene regulated by sequence | Size (bp) | Conserved TFBS present |
|---|---|---|---|---|
| SEQ ID NO: 37 | Sk-SH4[a] | MYLPF | 171 | CEBP, E2A, LRF, SRFb, SRFc |
| SEQ ID NO: 38 | Sk-SH4[b] | MYLPF | 51 | CEBP, E2A, LRF, SRFb |
| SEQ ID NO: 39 | Sk-SH4[c] | MYLPF | 60 | E2A, LRF, SRFb, MyoD |
| SEQ ID NO: 40 | Sk-SH4[d] | MYLPF | 41 | LRF, SRFb, p53, MyoD |
| SEQ ID NO: 41 | Sk-SH4[e] | MYLPF | 120 | CEBP, E2A, LRF, SRFb |

Bp: base pairs.

The functional fragments of Sk-SH4 were synthesized by conventional oligonucleotide synthesis and cloned into the pAAV9sc-Des-Luc2 vector as described in Example 2. AAV vector production and purification were carried out as described in Example 2. 6 weeks old CB17/IcrTac/Prkdc scid adult mice with an average weight of about 17-18 g per mouse were intravenously injected with the AAV vectors at a dose of $1\times10^{10}$vg per mouse. After 2 and 4 weeks post injection, the mice were subjected to imaging using the same biospace In Vivo photo Imaging System as described in Example 2.

Results

Figure 14:
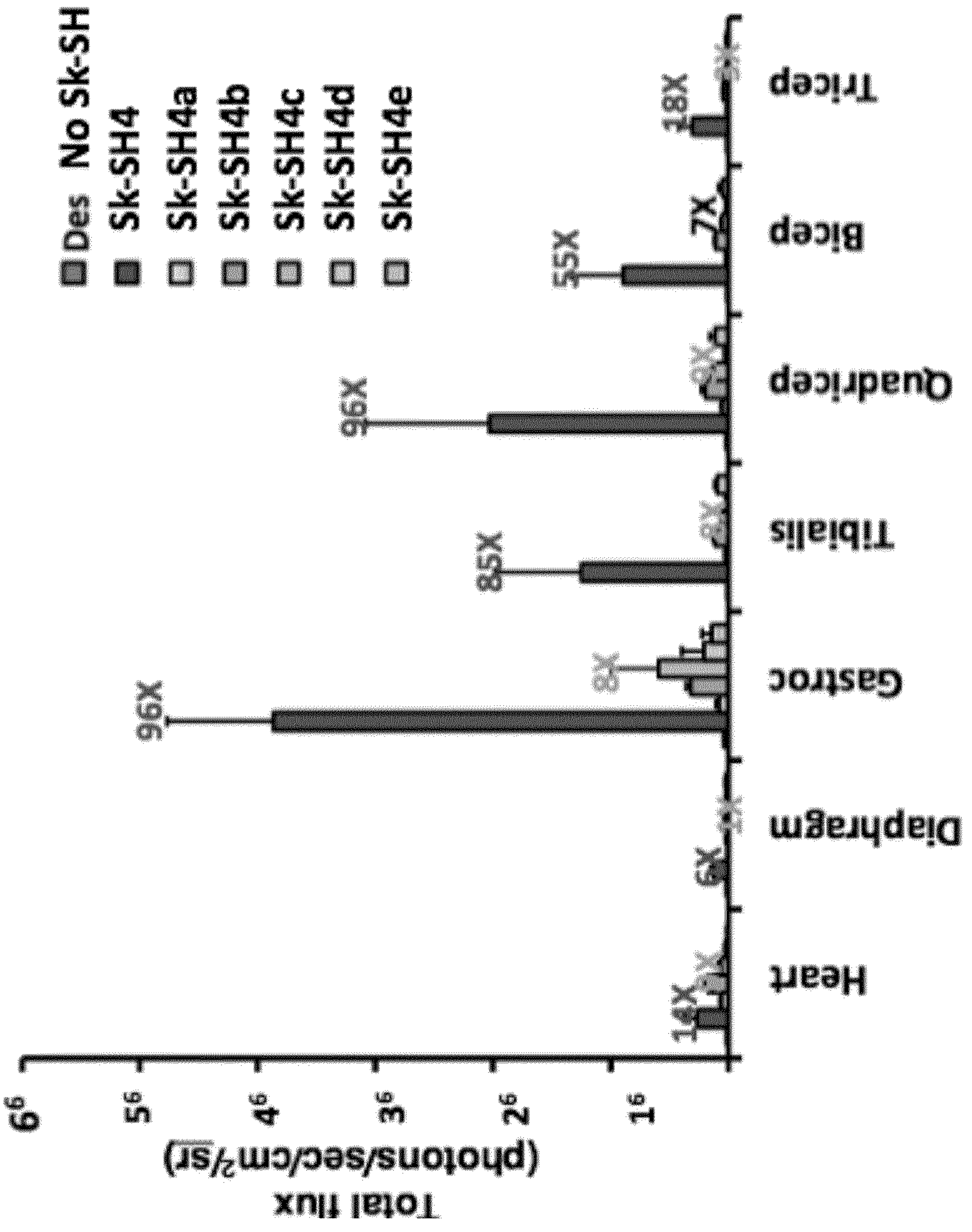
FIG. 14 shows luciferase expression in heart and muscle tissue of mice that were intravenously injected with, from left to right, AAV9sc-Des-Luc (control, no Sk-SH), AAV9sc-Sk-SH4-Des-Luc (Sk-SH4), AAV9sc-Sk-$SH4^a$-Des-Luc (Sk-$SH4^a$), AAV9sc-Sk-$SH4^b$-Des-Luc (Sk-$SH4^b$), AAV9sc-Sk-$SH4^c$-Des-Luc (Sk-$SH4^d$), AAV9sc-Sk-$SH4^d$-Des-Luc (Sk-$SH4^e$), or AAV9sc-Sk-$SH4^e$-Des-Luc (Sk-$SH4^e$) vector. Luciferase expression was measured as total flux, expressed in photons per second per centimetre squared per steradian (photons/sec/$cm^2$/sr), released by luciferase activity in the selected tissue 5 weeks post-injection. Results were presented as mean±standard error of the mean. The fold difference in luciferase expression in mice injected with Sk-SH4 and Sk-$SH4^b$ compared to mice that were injected with the control vector AAV9sc-Des-Luc2 without nucleic acid regulatory element is indicated.

The results shown in FIG. 14 show that all 5 fragments of the Sk-SH4 regulatory element were capable of augmenting the expression of the luciferase gene driven from the desmin promoter when compared to the reference construct without any regulatory element. The fragment Sk-SH4[b] showed the highest luciferase expression compared to the other fragments. However, none of the fragments could achieve higher or equal luciferase expression when compared to the expression induced by the full length Sk-SH4 fragment.

Example 8

In Vivo Validation of Modules of Muscle-Specific Regulatory Elements

The muscle-specific regulatory elements are further validated by making different combinations of the regulatory elements and/or by using several copies of the same regulatory element (e.g. CSk-SH1 combined with CSk-SH5; CSk-SH1 combined with Sk-SH4; CSk-SH1 combined with CSk-SH5 and SkSH4; CSk-SH1 repeated 3× or 4×; CSk-SH5 repeated 3× or 4×; Sk-SH4 repeated 3× or 4×). These constructs are incorporated upstream of the Des promoter in accordance with the protocol described in Example 2. AAV vector production and purification and animal studies are carried out as described in Example 2.

Further combinations are made with functional fragments of the identified muscle-specific regulatory elements as generated in Example 7.

Example 9

Binding of Transcription Factors to Muscle-Specific Regulatory Elements

Experimental Procedures 4 weeks old mice were intravenously injected in the periorbital vein with AVV vectors containing a Sk-SH4 and CSk-SH5 regulatory element, i.e. AAV9sc-Sk-SH4-Des-Luc and AAV9sc-CSk-SH5-Des-Luc, at a dose of $5\times10^9$ vg/per mouse.

Heart and muscle tissues harvested from the mice, were submersed in phosphate buffered saline (PBS) containing 1% formaldehyde, cut into small pieces and incubated at room temperature for 15 minutes. Fixation was stopped by the addition of 0.125 M glycine (final concentration). The tissue pieces were then treated with a Tissue-Tearer and finally spun down and washed twice in PBS. Chromatin was isolated by the addition of lysis buffer, followed by disruption with a Dounce homogenizer. Lysates were sonicated and the DNA sheared to an average length of 300-500 bp. Genomic DNA (Input) was prepared by treating aliquots of chromatin with RNase, proteinase K and heat for de-cross-linking, followed by ethanol precipitation. Pellets were re-suspended and the resulting DNA was quantified on a NanoDrop spectrophotometer. Extrapolation to the original chromatin volume allowed quantitation of the total chromatin yield. An aliquot of chromatin (30 μg) was pre-cleared with protein A agarose beads (Invitrogen, catalogue number 15918-014). Genomic DNA regions of interest were isolated using 4 μg of antibody against MEF2 (Santa Cruz, sc-313), SRF (Santa Cruz, sc-335) and CEBP (Santa Cruz, sc-150). Complexes were washed, eluted from the beads with SDS buffer, and subjected to RNase and proteinase K treatment. Crosslinks were reversed by incubation overnight at 65° C., and ChIP DNA was purified by phenol-chloroform extraction and ethanol precipitation. Quantitative PCR (QPCR) reactions were carried out in triplicate on specific genomic regions using SYBR Green Supermix (Bio-Rad). The resulting signals were normalized for primer efficiency by carrying out QPCR for each primer pair using Input DNA. Primer sequences for Sk-SH4 were: 5'-GTCCCTCACTCC-CAACTCAG-3' (SEQ ID NO: 33; forward) and 5'-GAG-GAGAAGGAGATCAGACACTG-3' (SEQ ID NO: 34; reverse); for CSk-SH5: 5'-TAGCTGGGCCTTTCCTTCTC-3' (SEQ ID NO: 35; forward) and 5'-CGTCTCCCTAGCAGCAACAG-3' (SEQ ID NO: 36; reverse). Negative control primers were purchased from Active Motif (Carlsbad, Calif., USA) (#71012) and are specific for non-transcribed gene sequences on chromosome 17.

Results

Figure 15A:
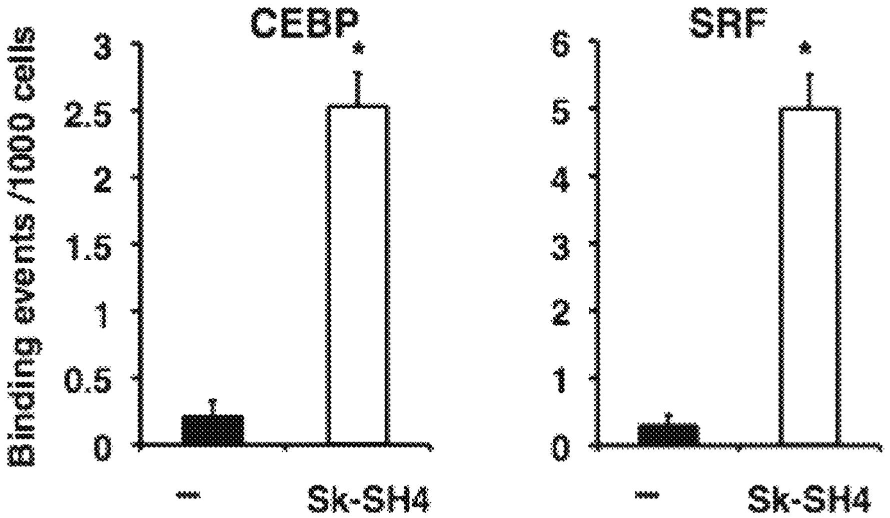
FIG. 15: Chromatin immunoprecipitation (CHIP) assay for heart (A, C) and muscle (B, D) tissue of mice injected with AAV9sc-Sk-SH4-Des-Luc (A, B) or AAV9sc-CSk-SH5-Des-Luc (C,D) ($5\times10^9$vg/mouse). Antibodies specific for the transcription factors CEBP, SRF and MEF2 were used. PCR primers were designed to amplify a region of Sk-SH4 that binds CEBP and SRF, or a region of CSk-SH5 that bind CEBP and MEF2, and as negative control (–) an un-transcribed region on chromosome 17 was used. Binding events for $10^3$ cells were determined for each of the corresponding primer pairs. Results are presented as mean±standard error of the mean. Significant difference compared to the negative control is indicated (t-test, * $P\leq0.05$).
Figure 15B:
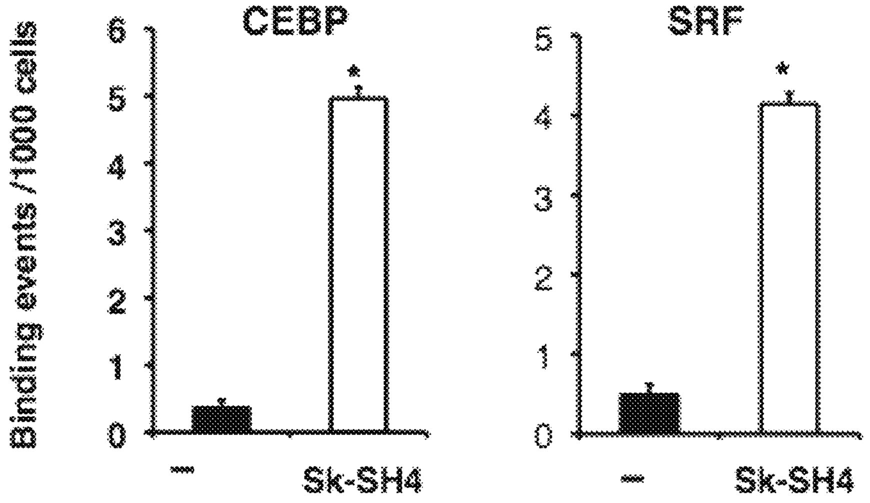
Figure 15C:
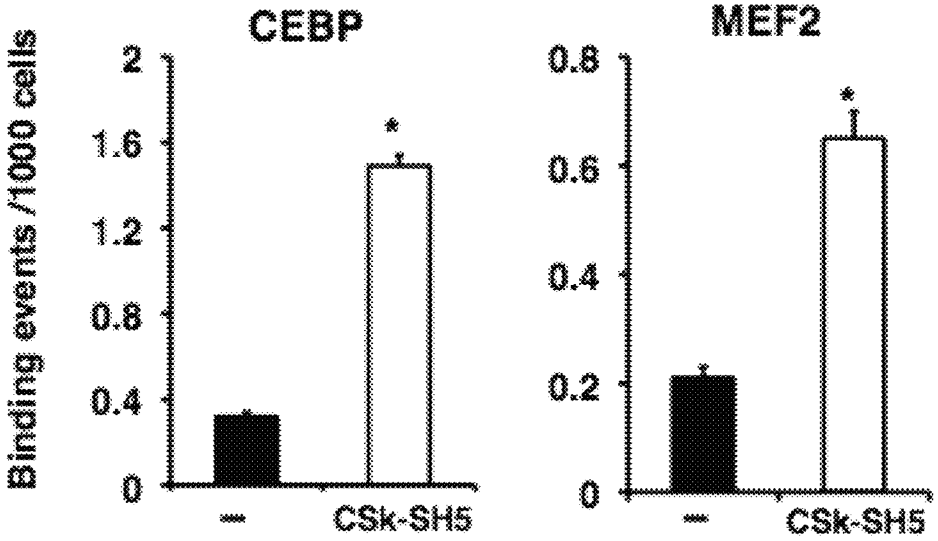
Figure 15D:
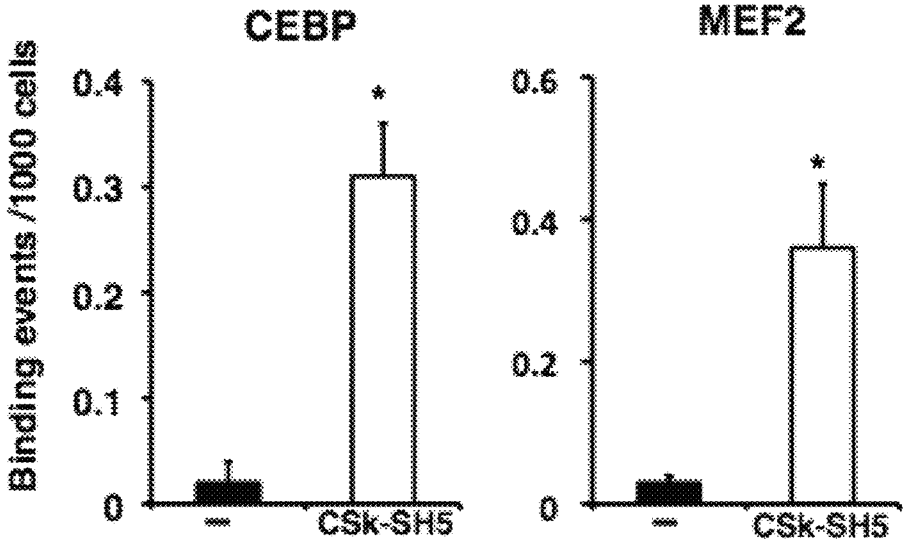

The muscle-specific regulatory element Sk-SH4 contains several putative transcription factor binding binding sites (TFBS), including E2A, SRF, p53, CEBP, LRF, MyoD and SREBP. Using a chromatin immuno-precipitation (CHIP) assay, binding of CEBP and SRF on the Sk-SH4 element was confirmed in the heart and skeletal muscle from mice that were injected with AAV9sc-Sk-SH4-Des-Luc vector (FIG. 15A,B). Similarly, binding of CEBP and MEF2 element on the CSk-SH5 regulatory element was shown in the heart and skeletal muscle from mice injected with AAV9sc-CSk-SH5-Des-Luc (FIG. 15C,D).

Example 10

Therapeutic Evaluation of Muscle-Specific Regulatory Elements Via AAV Vectors Comprising a Desmin Promoter The effect of the muscle-specific regulatory element Sk-SH4 on the expression and therapeutic efficacy of two therapeutic genes, in particular micro-dystrophin and follistatin, which have therapeutic potential for the treatment of muscle disease such as Duchenne muscular dystrophy (DMD) by gene therapy, was evaluated. MDX-SCID mice replicate the disease manifestations of Duchenne muscular dystrophy in patients and are therefore well suited to assess therapeutic efficacy of the AAVss-Sk-SH4-Des-MVM-MD1 and AAVss-Sk-SH4-Des-MVM-FST-2A-Luc vectors.

Experimental Procedures

Cloning Follistatin and MD1 Genes into AAV

Figure 16A:
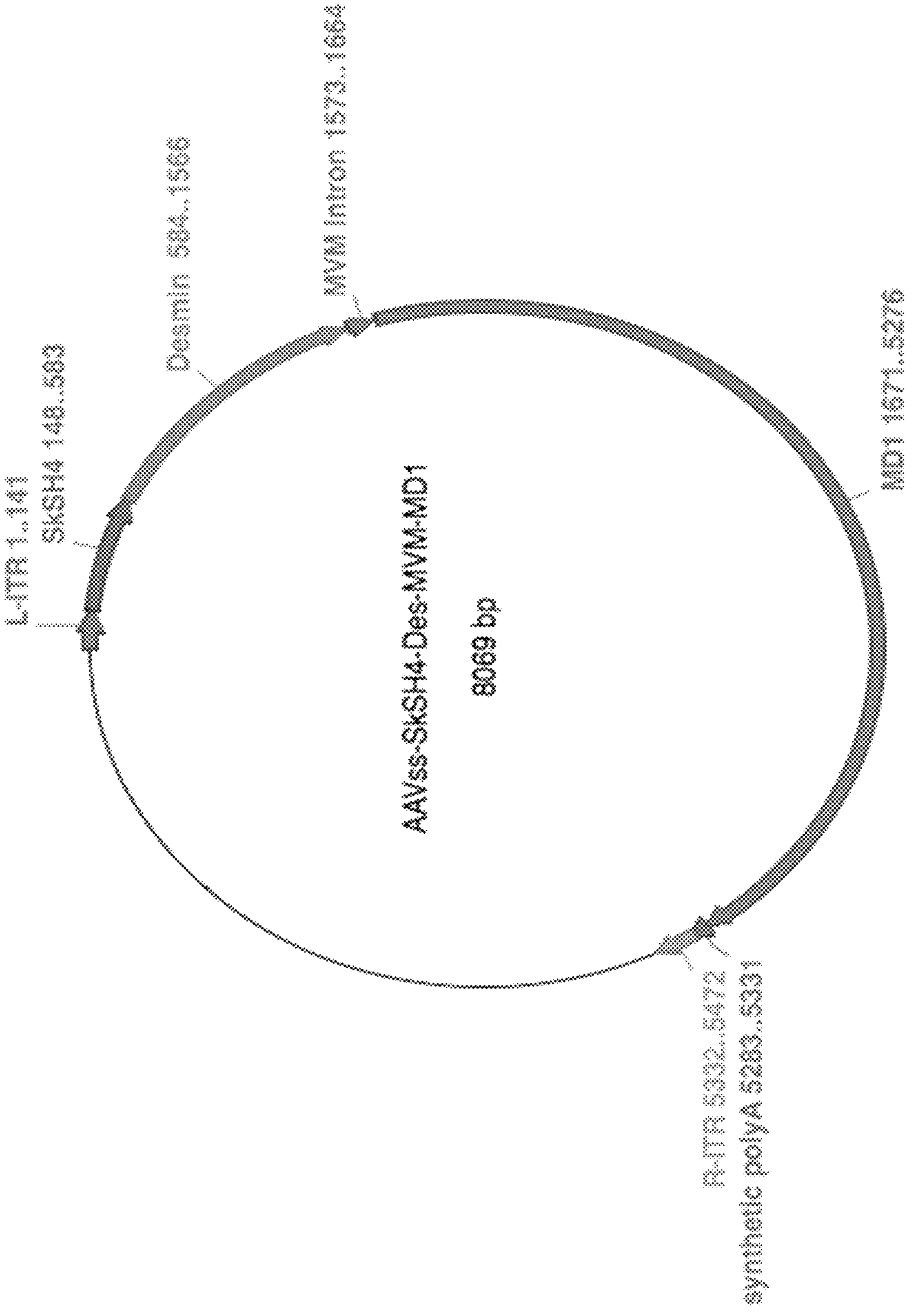
FIG. 16 shows schematic representations of single-stranded (ss) AAV plasmid constructs disclosed herein, which comprise the microdystrophin1 (MD1) (A, AAVss-SkSH4-Des-MVM-MD1) or follistatin (FST) (C, AAVssSkSH4-Des-MVM-FST-2A-Luc2) transgene regulated by the Desmin promoter operably linked to the muscle-specific nucleic acid regulatory element SkSH4 cloned upstream of the Desmin promoter. The follistatin gene was linked to the Luc2 reporter gene via a 2A peptide. The expression cassettes further comprise the Minute Virus of Mouse (MVM) intron and the 49 bp synthetic Proudfoot polyadenylation site (pA). The expression cassettes are flanked by inverted terminal repeats (ITR). (B) Nucleotide sequence of the AAVss-SkSH4-Des-MVM-MD1 plasmid construct (SEQ ID NO:44). (D) Nucleotide sequence of the AAVss-SkSH4-Des-MVM-FST-2A-Luc2 plasmid construct (SEQ ID NO:45).
Figure 16C:
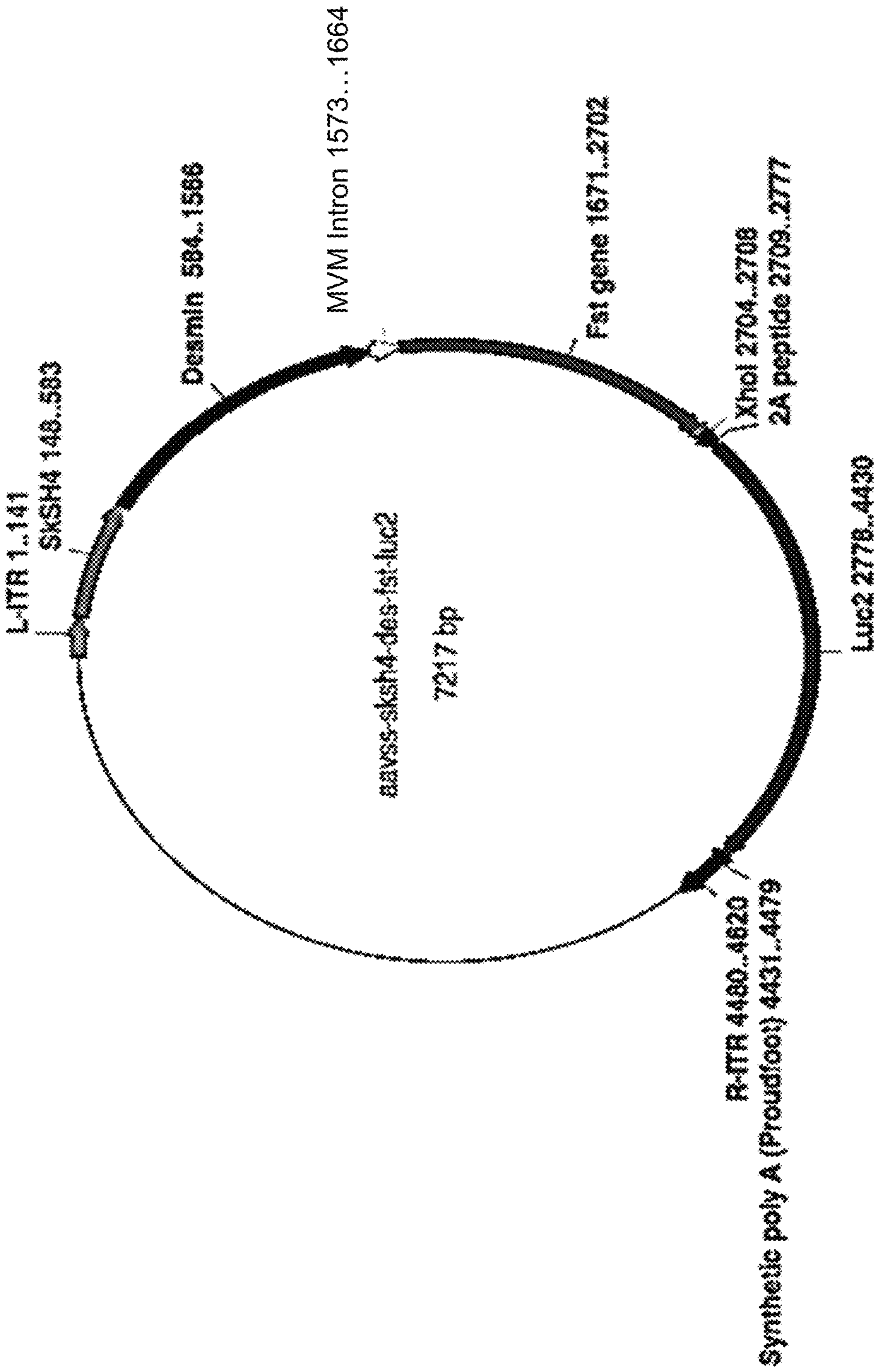

The microdystrophin 1 (MD1) (Koo et al., 2011) and follistatin (FST) (Kota et al., 2009) genes were cloned and driven from desmin promoter, which was operably linked to the muscle-specific regulatory element Sk-SH4. The MD1 gene was flanked by MluI and XhoI restriction sites at the 5' and 3' ends, while the FST gene was flanked by MluI and SalI restriction sites at the 5' and 3' ends, respectively and were synthesized by conventional oligonucleotide synthesis. The Sk-SH4 regulatory element, operably linked to the desmin promoter, was cloned upstream of the MVM intron in the context of a single stranded adeno-associated viral vector (AAVss) backbone. The vector also contained a 49 bp synthetic proudfoot polyadenylation site (Levitt N et al, 1989). The follistatin gene was linked to a luciferase reporter gene via a 2A polypeptide. The generated constructs were designated as pAAVss-Sk-SH4-Des-MVM-MD1 and pAAVss-Sk-CRM4-Des-MVM-FST-2A-Luc, respectively, and are schematically shown in FIG. 16.

AAV vector production and purification were carried out as described in Example 2.

Treadmill Test for Phenotypic Correction of MDX-SCID Mice 4 weeks old MDX-SCID mice (bred in house) were injected intravenously in a total volume of 100 μl with a dose of $2\times10^{10}$ vg per mouse of the AAVss-Sk-SH4-Des-MVM-MD1 and AAVss-Sk-SH4-Des-MVM-FST-2A-Luc vectors, individually or in combination. 8 weeks post-injection, the treated and control (injected with PBS) MDX-SCID mice were subjected to the treadmill test. The treadmill tests were performed using the Exer-3/6 open treadmill (Columbus instruments, USA). The inclination of the belt was adjusted to 10° uphill before performing the test. The initial speed was set at 10 m/min and thereafter the speed was increased by 1 m every minute. The test was terminated at a point when the mice sat for 5 seconds on the pulse grill. At that point the distance covered by the mice was recorded and the total distance covered by the mice during the course of the test was calculated by using the formula, $\text{distance}=((N+n)/2)*(N-n+1)$ where N is the time (in min) at the point of termination of the test and n is the time (in minutes) at the start of the test.

mRNA Analysis mRNA analysis was performed as described in Example 2. To quantify the mRNA of the microdystrophin and follistatin genes, a qPCR-based method was used using the primers 5'-GTGCCCTACTACATCAA-3' (SEQ ID NO:42) as forward primer and 5'-AGGTTGTGCTGGTCCA-3' (SEQ ID NO:43) as reverse primer (amplicon 206 bp) for the microdystrophin, and the Luc2-specific forward primer 5'-CCCACCGTCGTATTCGTGAG-3' (SEQ ID NO: 14) and reverse primer 5'-TCAGGGCGATGGTTTTGTCCC-3' (SEQ ID NO: 15) (amplicon 217 bp) for the follistatin gene.

Results

Figure 17:
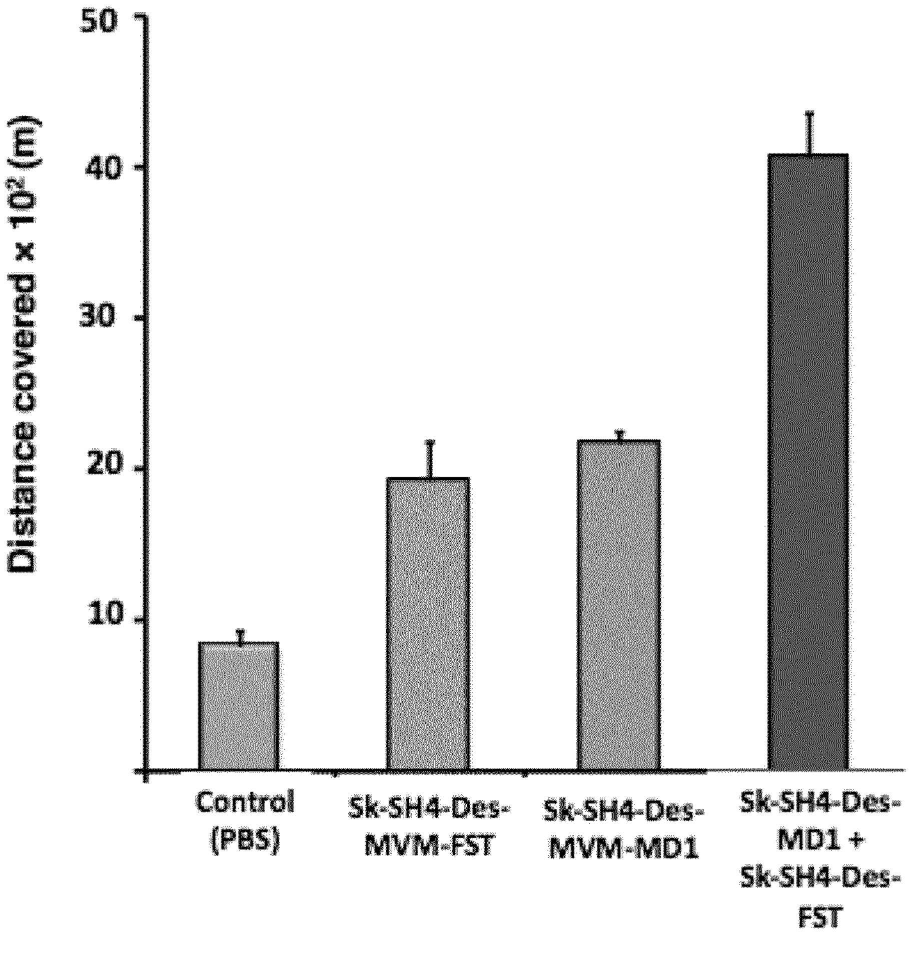
FIG. 17: Treadmill test for MDX-SCID mice injected with, from left to right, PBS (control), AAVss-Sk-SH4-Des-MVM-FST-2A-Luc, AAVss-Sk-SH4-Des-MVM-MD1, or the combination of AAVss-Sk-SH4-Des-MVM-FST-2A-Luc and AAVss-Sk-SH4-Des-MVM-MD1. Results are expressed as the calculated distance covered by each group of mice when run on a treadmill machine.

The results of the treadmill test clearly showed that the mice treated by gene therapy with either MD1 or FST or the combination of both, outperformed the untreated control MDX-SCID mice (FIG. 17). The MDX-SCID mice injected with either the AAVss-Sk-SH4-Des-MVM-MD1 or the AAVss-Sk-SH4-Des-MVM-FST-2A-Luc vector covered twice the distance covered by the control mice. When both vectors were co-injected into the MDX-SCID mice, a distance of 4 km was covered, which is 4 times more than the distance covered by the control MDX-SCID mice injected with PBS. These results clearly demonstrate that therapeutic efficacy can be achieved using these vectors.

Figure 18:
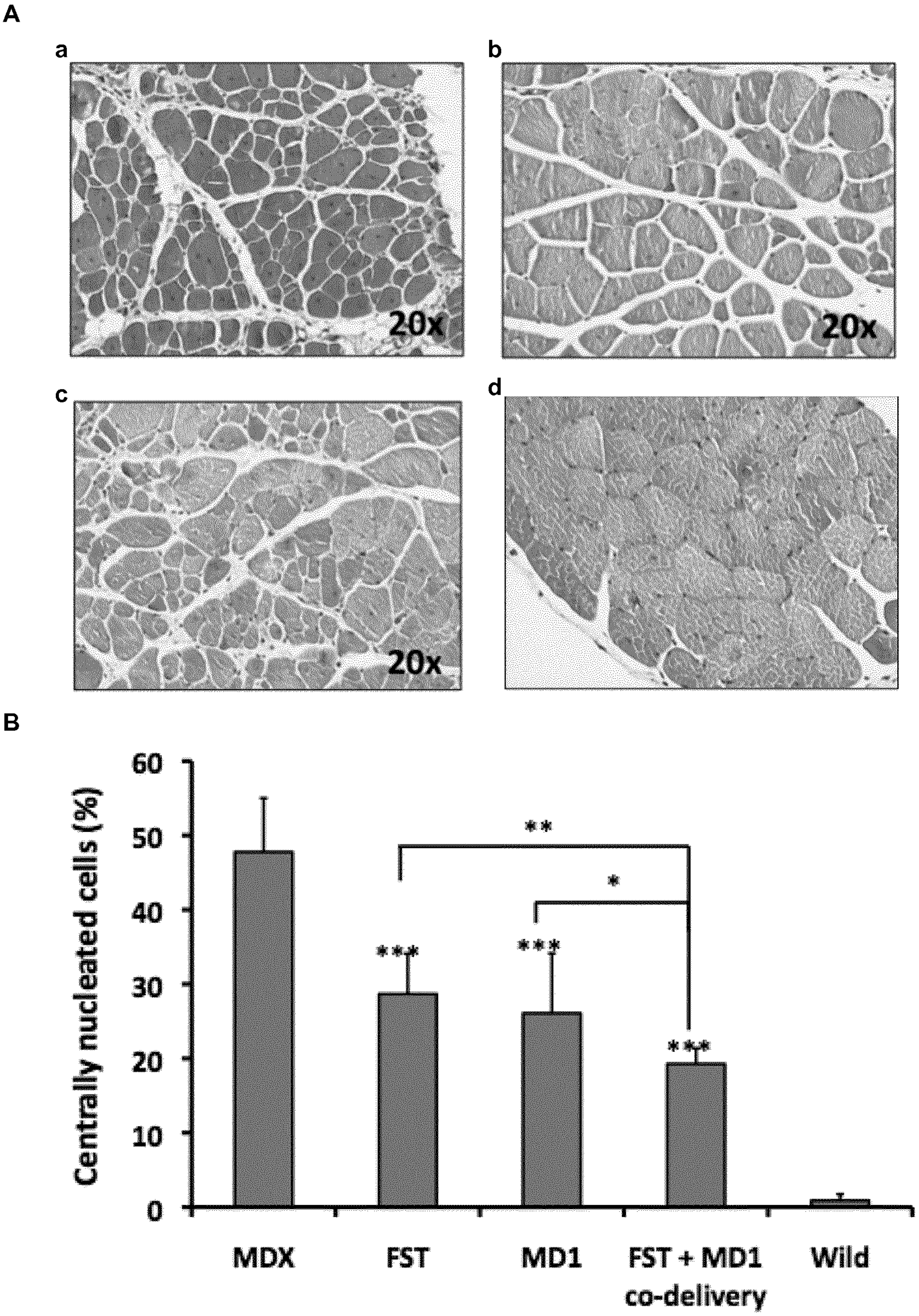
FIG. 18: (A) Hematoxylin/eosin staining of gastrocnemius muscle tissues of MDX/SCID mice injected with PBS (a, control), AAVss-Sk-SH4-Des-MVM-FST-2A-Luc (b), AAVss-Sk-SH4-Des-MVM-MD1 (c) or the combination of AAVss-Sk-SH4-Des-MVM-MD1 and AAVss-Sk-SH4-Des-MVM-FST-2A-Luc (d). (B) Quantification of centrally nucleated cells in wild-type C57BI/6 mice, untreated MDX/SCID mice (control), and MDX/SCID mice injected with AAVss-Sk-SH4-Des-MVM-MD1 (MD1), AAVss-Sk-SH4-Des-MVM-FST-2A-Luc (FST) or both (FST+MD1) therapeutic vectors. Statistical analysis was performed on H&E-stained transversally transected myofibers of gastronemius muscle embedded in paraffin. * ≤0.0001 ≤0.001 *≤0.05

The significant physiologic effect of the gene therapy using the AAVss-Sk-SH4-Des-MVM-MD1 or the AAVss-Sk-SH4-Des-MVM-FST-2A-Luc vector or their combined use was confirmed by histologic examination. Hematoxylin/eosin-stained muscle sections were scored for % centrally nucleated cells for the different experimental groups (FIG. 18). The muscle sections of C57B6 wild-type mice showed predominantly peripheral localization of the nucleus in the myofibers (data not shown) and a minimal percentage (<2%) of the nuclei was centrally located (FIG. 18B). In untreated, control, MDX/SCID mice, the nuclei were predominantly (about 50% of the nuclei) centrally located in the transversally transected myofibers (FIG. 18Aa, FIG. 18B). MDX/SCID mice injected with AAVss-Sk-SH4-Des-MVM-MD1 (AAV9-MD1) (FIG. 18Ac, FIG. 18B) or AAVss-Sk-SH4-Des-MVM-FST-2A-Luc (AAV9-FST) (FIG. 18Ab, FIG. 18B), all showed a decreased number of myofibers that are centrally nucleated. Co-administration of both, AAVss-Sk-SH4-Des-MVM-MD1 and AAVss-Sk-SH4-Des-MVM-FST-2A-Luc vectors, resulted in an even more profound shift in nuclear localization towards the periphery of the myofibers, and a further reduction in the percentage of centrally located nuclei (FIG. 18Ad, FIG. 18B). These results are indicative of a reduced regenerative stimulus and phenotypic correction after the gene therapy. Consequently, the shift of nuclear localization from a central to a more periheral location in the myofibers is consistent with the phenotypic correction as shown by the improved muscle strength and mobility in the treadmill assay.

Figure 19A:
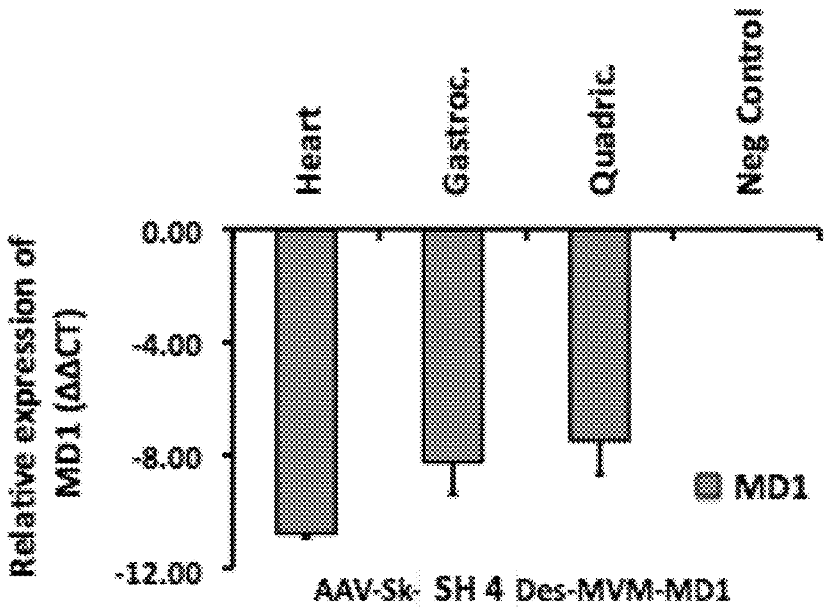
FIG. 19: Microdystrophin1 (MD1) (A,B) and follistatin (FST) (C) mRNA levels in heart and muscle (gastrocnemius and quadriceps) tissues from mice that were intravenously injected with the AAVss-Sk-SH4-Des-MVM-MD1 vector (A), the combination of AAVss-Sk-SH4-Des-MVM-MD1 and AAVss-Sk-SH4-Des-MVM-FST-2A-Luc (B), or AAVss-Sk-SH4-Des-MVM-FST (C) relative to expression of endogenous housekeeping gene (GAPDH: Glyceraldehyde-3-phosphate dehydrogenase). Results are presented as relative expression of MD1 or FST (ΔΔCT).
Figure 19B:
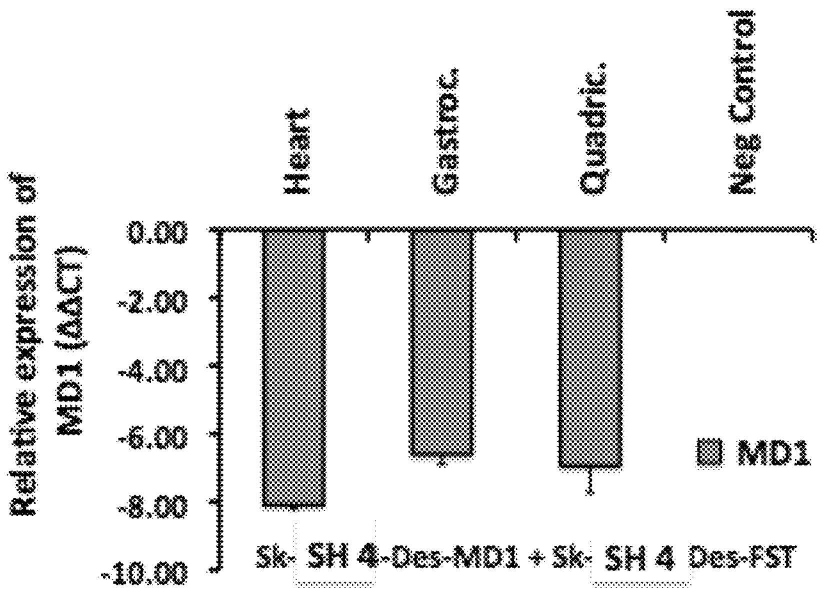
Figure 19C:
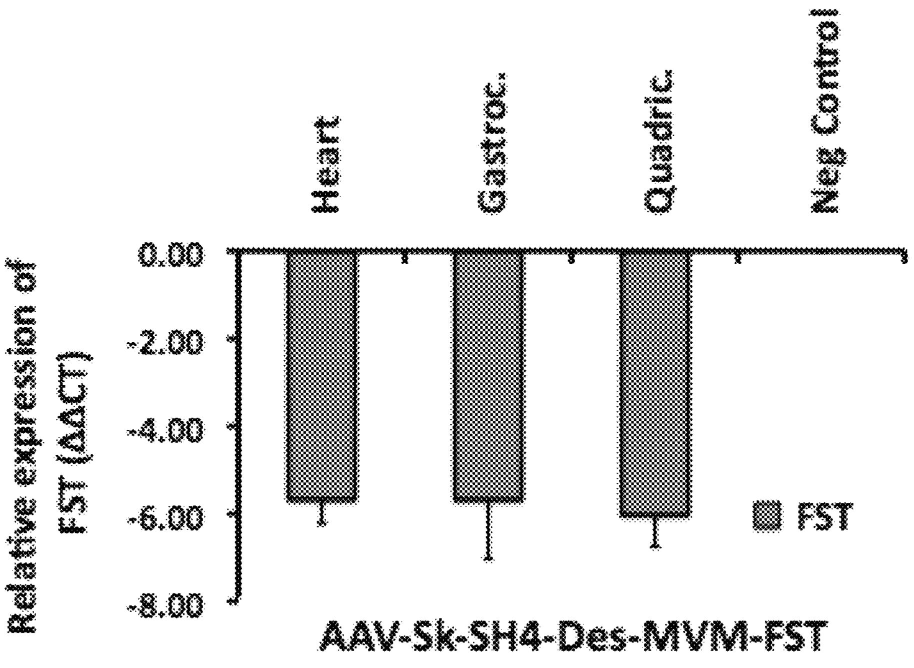

Using quantitative RT-PCR, the expression of the micro-dystrophin (MD1) and the follistatin (FST) genes in biopsies from heart and muscle tissues, in particular gastrocnemius and quadriceps, of the mice injected with the pAAVss-Sk-SH4-Des-MVM-MD1 construct, the pAAVss-Sk-SH4-Des-MVM-FST-2A-Luc construct or the combination of both constructs was assessed (FIG. 19).

Example 11

In Vivo Comparison of Muscle-Specific Regulatory Elements with CMV and SPc5-12 Promoters Experimental Procedures AAV vector production and purification were carried out as described in Example 2.

The AAVsc-Des-MVM-Luc vector is a self-complementary AAV vector containing a luciferase (Luc) transgene driven from the desmin promoter. The scAAV vector backbone also contained a Minute Virus of Mouse (MVM) intron and a Simian Virus 40 (SV40) polyadenylation site (pA).

The AAVsc-SPc5-12-MVM-Luc vector had the same configuration as the AAVsc-Des-MVM-Luc vector, but the desmin promoter was replaced by the SPc5-12 promoter.

AAV vectors comprising the muscle-specific regulatory element Sk-SH4 were generated according to the protocol described in Example 2. Briefly, the muscle-specific regulatory element Sk-SH4 was synthesized by conventional oligonucleotide synthesis and cloned upstream of the desmin or the SPc5-12 promoter in the context of the AAV vector backbone of AAVsc-Des-MVM-Luc or AAVsc-SPc5-12-MVM-Luc, respectively.

The AAVsc-CMV-Luc vector was generated by cloning the Cytomegalovirus (CMV) promoter (SEQ ID NO: 30) upstream the luciferase reporter gene instead of the desmin promoter in the context of the AAV vector backbone of AAVsc-Des-Luc, which also contained a polyadenylation site (pA).

Figure 20:
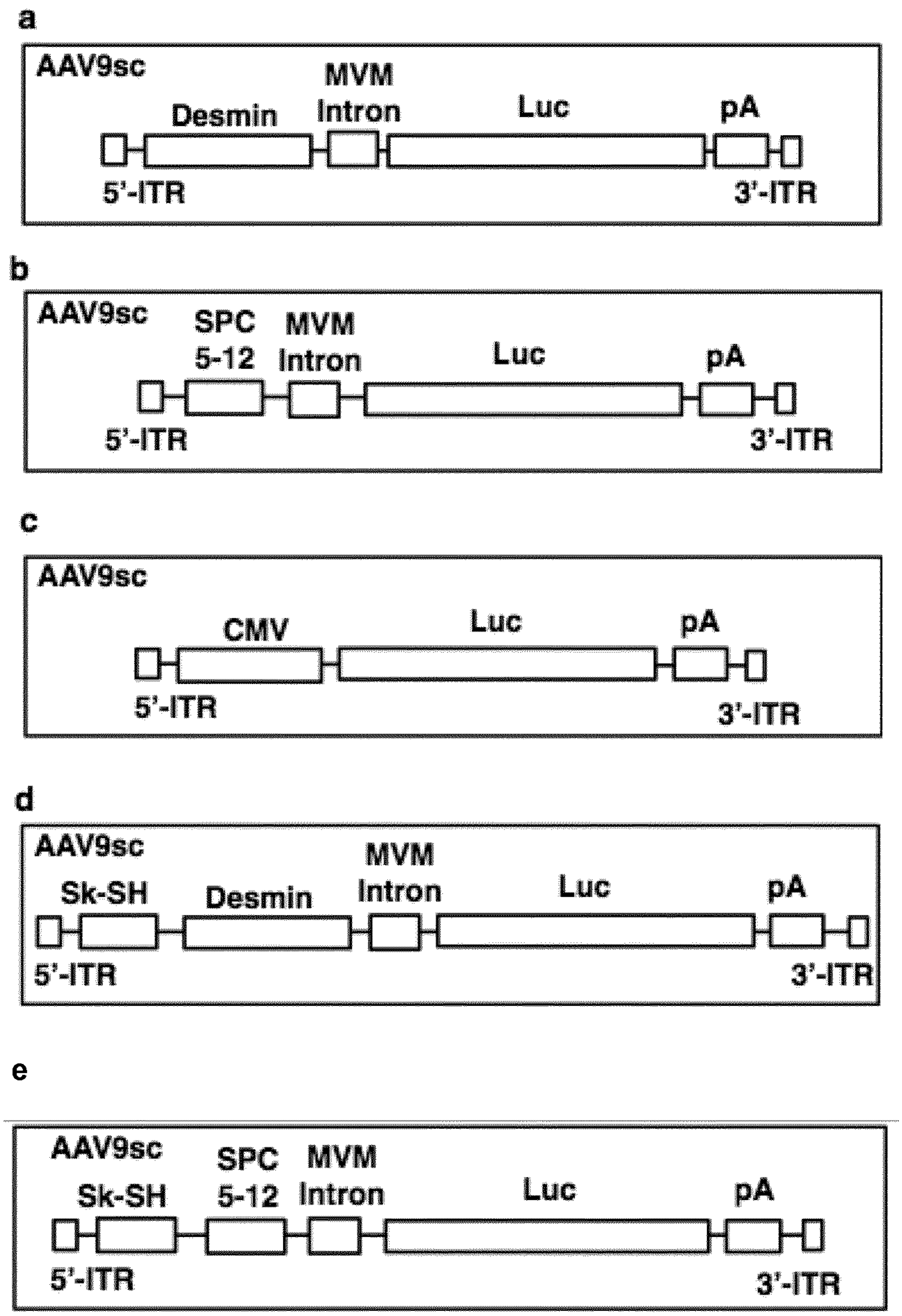
FIG. 20 shows schematic representations of self-complementary (sc) AAV constructs disclosed herein, which comprise the luciferase (Luc) transgene regulated by (a) the cardiac and skeletal muscle-specific desmin (Desmin) promoter, (b) the SPc5-12 promoter, (c) the cytomegalovirus (CMV) promoter, (d) the Desmin promoter operably linked to a muscle-specific (Sk-SH) nucleic acid regulatory element cloned upstream of the Desmin promoter, or (e) the SPc5-12 promoter operably linked to a muscle-specific (Sk-SH) nucleic acid regulatory element cloned upstream of the SPc5-12 promoter. Expression cassettes (a), (b), (d) and (e) further comprise the Minute Virus of Mouse (MVM) intron and a polyadenylation signal (pA). The expression cassettes are flanked by inverted terminal repeats (ITR).

A schematic representation of the different vectors is shown in FIG. 20.

Adult CB17/IcrTac/Prkdcscid mice were intravenously injected with the different vectors (n=3) at a dose of $1\times10^{10}$ vg/mouse.

mRNA analysis was performed as described in Example 3.

Results

Figure 21:
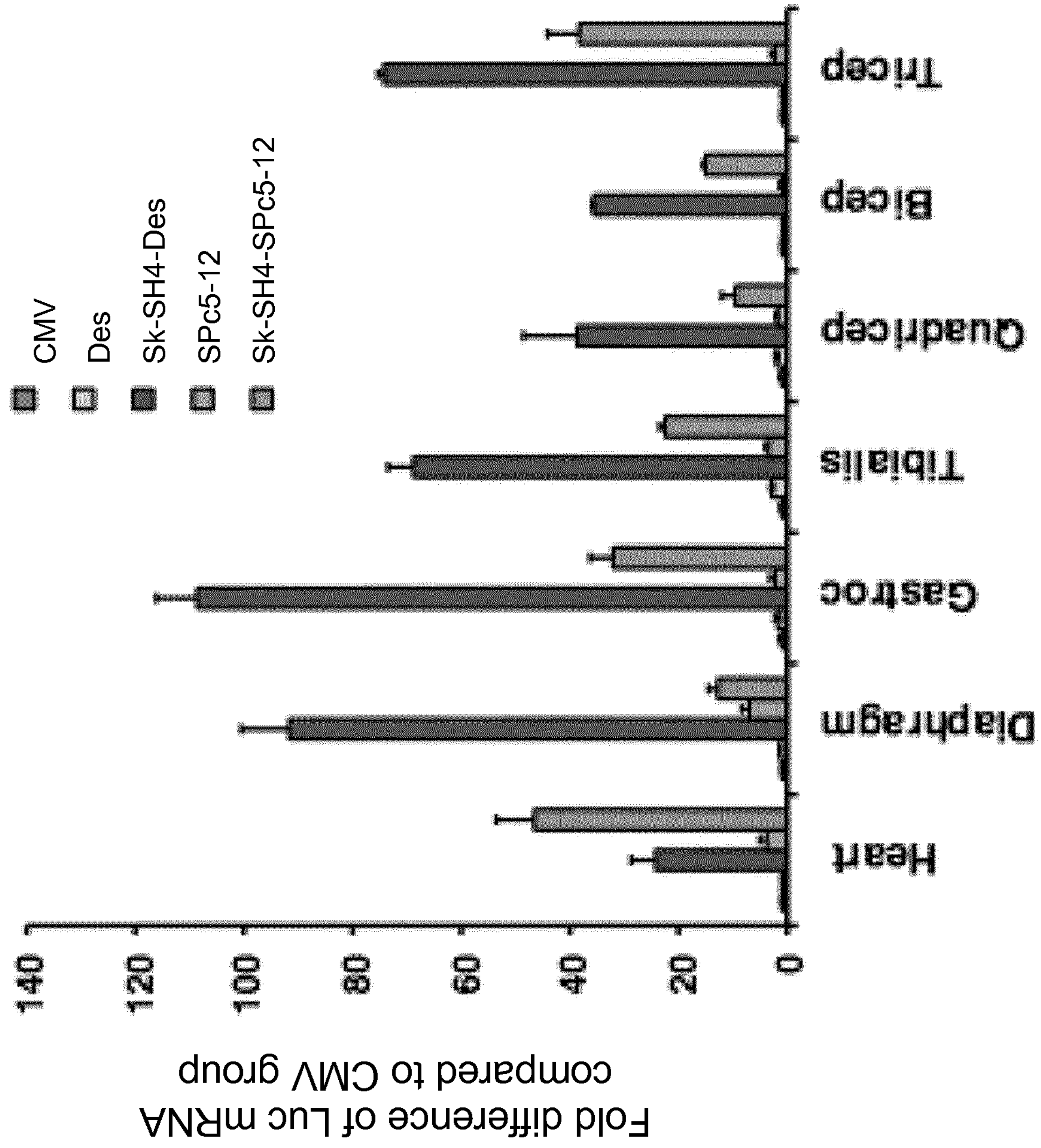
FIG. 21: Difference in Luc mRNA levels in selected tissues of CB17/IcrTac/Prkdcscid mice that were intravenously injected with, from left to right, AAVsc-CMV-Luc, AAVsc-Des-MVM-Luc, AAVsc-Sk-SH4-Des-MVM-Luc, AAVsc-SPc5-12-MVM-Luc or AAVsc-Sk-SH4-SPc5-12-MVM-Luc vector as schematically shown in FIG. 20, compared to mice that were injected with AAVsc-CMV-Luc vector. Luc mRNA levels were measured by qRT-PCR from total RNA extracted from biopsies of the indicated tissues. Results were presented as mean±standard error of the mean, $*p<0.05$; $**p<0.001$.

Luciferase mRNA levels in mice injected with a vector that expressed the luciferase gene from the desmin promoter operably linked to the muscle-specific regulatory element Sk-SH4 were compared versus mice that were injected with a vector that expressed the luciferase gene from the Cytomegalovirus (CMV) or the SPc5-12 promoters, which were not operably linked to a muscle-specific regulatory element. The CMV and SPc5-12 promoters are considered the most powerful promoters known to allow robust gene expression in the heart and skeletal muscles. FIG. 21 shows that the vector comprising the Sk-SH4 muscle-specific regulatory element of the invention operably linked to the desmin promoter allows for much better expression than the vectors comprising the CMV or the SPc 5-12 promoter without muscle-specific regulatory element.

Similarly, when the Sk-SH4 muscle-specific regulatory element was operably linked to the SPc5-12 promoter, increased luciferase mRNA levels were observed in the heart and all skeletal muscle types tested (FIG. 21). However, the mRNA level induced from this construct was lower than when the Sk-SH4 muscle-specific regulatory element of the invention is operably linked to the desmin promoter.

The invention claimed is:

1. A nucleic acid expression cassette comprising at least one nucleic acid regulatory element for enhancing muscle-specific gene expression, operably linked to a promoter and a heterologous transgene, wherein said nucleic acid regulatory element comprises the sequence set forth in SEQ ID NO:5.

2. The nucleic acid expression cassette according to claim 1, wherein the promoter is a muscle-specific promoter.

3. The nucleic acid expression cassette according to claim 2, wherein the muscle-specific promoter is from the desmin (DES) gene or the SPc5-12 promoter.

4. The nucleic acid expression cassette according to claim 1, wherein the transgene encodes a therapeutic protein, an immunogenic protein, or a structural protein.

5. The nucleic acid expression cassette according to claim 4, wherein the therapeutic protein, the immunogenic protein, or the structural protein, is dystrophin or a sarcoglycan.

6. The nucleic acid expression cassette according to claim 1, wherein the nucleic acid regulatory element enhances cardiac and skeletal muscle-specific gene expression.

7. The nucleic acid expression cassette according to claim 1, wherein the nucleic acid regulatory element has a maximal length of 600 nucleotides.

8. A vector comprising at least one nucleic acid regulatory element for enhancing muscle-specific gene expression, operably linked to a promoter and a heterologous transgene, wherein said nucleic acid regulatory element comprises the sequence set forth in SEQ ID NO:5.

9. The vector according to claim 8, which is a viral vector.

10. The vector according to claim 8, which is an adeno-associated viral vector.

11. The vector according to claim 8, wherein the nucleic acid regulatory element enhances cardiac and skeletal muscle-specific gene expression.

12. The vector according to claim 8, wherein the nucleic acid regulatory element has a maximal length of 600 nucleotides.

13. A pharmaceutical composition comprising the nucleic acid expression cassette according to claim 1, or a vector comprising the nucleic acid expression cassette, and a pharmaceutically acceptable carrier.

14. An in vitro or ex vivo method for expressing a transgene product in a muscle cell comprising:

a) introducing the nucleic acid expression cassette according to claim 1 or a vector comprising said nucleic acid expression cassette in a muscle cell; and b) expressing the transgene product in said muscle cell.

15. The method according to claim 14, wherein the promoter is a muscle-specific promoter.

16. A method for muscle-directed gene therapy for the treatment of Duchenne muscular dystrophy comprising administering to a subject an effective amount of a) an adeno-associated viral vector comprising the nucleic acid expression cassette of claim 1, wherein the promoter is the desmin promoter or the SPc5-12 promoter, and wherein the transgene encodes a microdystrophin or follistatin; or b) a pharmaceutical composition comprising said vector and a pharmaceutically acceptable carrier.

17. The method according to claim 16, wherein the vector is administered intravenously.

18. The method according to claim 16, wherein said transgene comprises microdystrophin 1 (MDI) gene or follistatin (FST) gene.

19. A method for muscle-directed gene therapy for the treatment of limb girdle muscular dystrophy comprising administering to a subject an effective amount of a) an adeno-associated viral vector comprising the nucleic acid expression cassette of claim 1, wherein the promoter is the desmin promoter of the Spc5-12 promotor, and wherein the transgene encodes a sarcoglycan; or b) a pharmaceutical composition comprising said vector and a pharmaceutically acceptable carrier.

* * * * *

UNITED STATES PATENT AND TRADEMARK OFFICE

CERTIFICATE OF CORRECTION

PATENT NO. : 11,072,801 B2
APPLICATION NO. : 15/112795
DATED : July 27, 2021
INVENTOR(S) : Thierry Vandendriessche et al.

It is certified that error appears in the above-identified patent and that said Letters Patent is hereby corrected as shown below:

In the Claims

Claim 18, Column 94, Line 17: please delete "(MDI)" and insert --(MD1)--.

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*